(12) United States Patent
Jacobs et al.

(10) Patent No.: US 7,510,566 B2
(45) Date of Patent: *Mar. 31, 2009

(54) MULTI-POINT TISSUE TENSION DISTRIBUTION DEVICE AND METHOD, A CHIN LIFT VARIATION

(75) Inventors: Daniel Jacobs, Palo Alto, CA (US); Robert J. Elson, Los Altos Hills, CA (US)

(73) Assignee: Coapt Systems, Inc., Palo Alto, CA (US)

( * ) Notice: Subject to any disclaimer, the term of this patent is extended or adjusted under 35 U.S.C. 154(b) by 779 days.

This patent is subject to a terminal disclaimer.

(21) Appl. No.: 10/418,541

(22) Filed: Apr. 17, 2003

(65) Prior Publication Data

US 2004/0010276 A1 Jan. 15, 2004

Related U.S. Application Data

(63) Continuation-in-part of application No. 10/299,119, filed on Nov. 18, 2002, now abandoned, which is a continuation of application No. 09/788,118, filed on Feb. 16, 2001, now Pat. No. 6,485,503, which is a continuation-in-part of application No. 09/574,603, filed on May 19, 2000, now Pat. No. 6,645,226.

(51) Int. Cl.
*A61B 17/08* (2006.01)
(52) U.S. Cl. .................................... 606/215
(58) Field of Classification Search ................ 606/215, 606/151, 157, 213, 216, 230, 214, 228, 219, 606/232, 233
See application file for complete search history.

(56) References Cited

U.S. PATENT DOCUMENTS

| 833,571 A | 10/1906 | Bailery |
| 2,421,193 A | 5/1947 | Gardner |
| 2,472,009 A | 5/1949 | Gardner |
| 2,631,327 A | 3/1953 | Roberts |

(Continued)

FOREIGN PATENT DOCUMENTS

FR 2 744 623 8/1997

(Continued)

OTHER PUBLICATIONS

PCT/US01/16346.

(Continued)

*Primary Examiner*—Kevin T Truong
(74) *Attorney, Agent, or Firm*—DLA Piper LLP (US)

(57) ABSTRACT

A tissue approximation device and processes for using the device are provided. The device is an implantable, biodegradable construct that has attachment points emanating from a supportive backing. The device improves the mechanical phase of wound healing and optimally distributes tension over the contact area between the device and tissue. Processes for using the device include soft tissue attachment and soft tissue to bone attachment. Several variations are particularly applicable to facilitating tissue approximation in surgical cosmetic applications, particularly chin lifts. Generally, tissue to be lifted may be set on a chin lift device via attachment points before or after the device is secured to a patient's bone. Variations of the device are described along with a method of installing the chin lift device. Also described is a tool particularly useful for installing a chin lift device.

17 Claims, 44 Drawing Sheets

U.S. PATENT DOCUMENTS

| | | | |
|---|---|---|---|
| 2,818,865 A | 1/1958 | Jacoby, Jr. | |
| 3,031,730 A | 5/1962 | Morin | |
| 3,471,903 A | 10/1969 | Northrup et al. | |
| 3,646,615 A | 3/1972 | Ness | |
| 3,914,144 A | 10/1975 | Ribich et al. | |
| 3,926,193 A | 12/1975 | Hasson | |
| 3,973,277 A | 8/1976 | Semple et al. | |
| 3,981,051 A | 9/1976 | Brumlik | |
| 4,259,959 A | 4/1981 | Walker | |
| 4,430,998 A | 2/1984 | Harvey et al. | |
| 4,501,029 A | 2/1985 | McMinn | |
| 4,535,772 A | 8/1985 | Sheehan | |
| 4,548,202 A | 10/1985 | Duncan | |
| 4,610,250 A | 9/1986 | Green | |
| 4,651,724 A | 3/1987 | Berentey et al. | |
| 4,820,305 A | 4/1989 | Harms et al. | |
| 4,865,026 A | 9/1989 | Barrett | |
| 4,950,284 A | 8/1990 | Green | |
| 4,960,420 A | 10/1990 | Goble et al. | |
| 4,979,956 A | 12/1990 | Silvestrini | |
| 4,998,319 A | 3/1991 | Ford | |
| 5,047,047 A | 9/1991 | Yoon | |
| 5,108,422 A | 4/1992 | Green et al. | |
| 5,176,692 A | 1/1993 | Wilk et al. | |
| 5,179,964 A | 1/1993 | Cook | |
| 5,254,127 A * | 10/1993 | Wholey et al. | 606/153 |
| 5,263,973 A | 11/1993 | Cook | |
| 5,342,376 A | 8/1994 | Ruff | |
| 5,342,395 A | 8/1994 | Jarett et al. | |
| 5,352,229 A | 10/1994 | Goble et al. | |
| 5,383,897 A | 1/1995 | Wholey | |
| 5,425,747 A | 6/1995 | Brotz | |
| 5,486,196 A | 1/1996 | Hirshowitz et al. | |
| 5,531,760 A | 7/1996 | Alwafaie | |
| 5,531,790 A | 7/1996 | Frechet et al. | |
| D374,286 S | 10/1996 | Geobel et al. | |
| 5,569,272 A | 10/1996 | Reed et al. | |
| 5,571,104 A | 11/1996 | Li | |
| 5,571,216 A | 11/1996 | Anderson | |
| 5,584,859 A | 12/1996 | Brotz | |
| 5,586,971 A | 12/1996 | Newman | |
| 5,591,203 A | 1/1997 | Fahy | |
| 5,598,610 A | 2/1997 | Torigoe et al. | |
| 5,611,814 A | 3/1997 | Lorenc | |
| 5,662,714 A | 9/1997 | Charvin et al. | |
| 5,723,009 A | 3/1998 | Frechet et al. | |
| 5,779,706 A | 7/1998 | Tschakaloff | |
| 5,785,713 A | 7/1998 | Jobe | |
| 5,800,544 A | 9/1998 | Demopulos et al. | |
| 5,868,746 A | 2/1999 | Sarver et al. | |
| 5,906,617 A | 5/1999 | Meislin | |
| 5,911,721 A | 6/1999 | Nicholson et al. | |
| 5,916,224 A * | 6/1999 | Esplin | 606/151 |
| 5,919,234 A | 7/1999 | Lemperle et al. | |
| 5,925,078 A | 7/1999 | Anderson | |
| 5,931,840 A | 8/1999 | Goble et al. | |
| 5,941,878 A | 8/1999 | Medoff | |
| 5,950,633 A | 9/1999 | Lynch et al. | |
| 5,954,747 A | 9/1999 | Clark | |
| 5,961,520 A | 10/1999 | Beck et al. | |
| 5,968,097 A | 10/1999 | Frechet et al. | |
| 5,984,927 A | 11/1999 | Wenstrom, Jr. et al. | |
| 5,984,949 A | 11/1999 | Levin | |
| 6,015,410 A | 1/2000 | Törmälä et al. | |
| 6,039,741 A | 3/2000 | Meislin | |
| 6,066,159 A | 5/2000 | Bergstrom | |
| 6,080,192 A | 6/2000 | Demopulos et al. | |
| 6,083,244 A | 7/2000 | Lubbers et al. | |
| 6,106,544 A | 8/2000 | Brazeau | |
| 6,106,556 A | 8/2000 | Demopulos et al. | |
| 6,110,100 A | 8/2000 | Talpade | |
| 6,132,442 A | 10/2000 | Ferragamo et al. | |
| 6,165,203 A | 12/2000 | Krebs | |
| 6,168,596 B1 | 1/2001 | Wellisz et al. | |
| 6,168,633 B1 | 1/2001 | Shoher et al. | |
| 6,235,058 B1 | 5/2001 | Huene | |
| 6,241,747 B1 | 6/2001 | Ruff | |
| 6,267,772 B1 | 7/2001 | Mulhauser et al. | |
| 6,270,517 B1 | 8/2001 | Brotz | |
| 6,296,641 B2 | 10/2001 | Burkhead et al. | |
| 6,328,743 B2 * | 12/2001 | Lerch | 606/215 |
| 6,329,564 B1 | 12/2001 | Lebner | |
| 6,350,284 B1 | 2/2002 | Tormala et al. | |
| D462,766 S | 9/2002 | Jacobs et al. | |
| 6,445,535 B1 | 9/2002 | Rehm | |
| 6,482,232 B1 | 11/2002 | Boucher et al. | |
| 6,485,493 B1 * | 11/2002 | Bremer | 606/215 |
| 6,485,503 B2 | 11/2002 | Jacobs et al. | |
| 6,540,769 B1 | 4/2003 | Miller, III | |
| 6,645,226 B1 | 11/2003 | Jacobs et al. | |
| 6,692,499 B2 | 2/2004 | Törmälä et al. | |
| 6,712,830 B2 | 3/2004 | Esplin | |
| 7,041,135 B2 | 5/2006 | Michelson | |
| 2002/0022861 A1 | 2/2002 | Jacobs et al. | |
| 2002/0173807 A1 | 11/2002 | Jacobs | |
| 2003/0065360 A1 | 4/2003 | Jacobs et al. | |
| 2003/0069602 A1 | 4/2003 | Paganelli et al. | |
| 2003/0074021 A1 | 4/2003 | Morriss et al. | |
| 2005/0119694 A1 | 6/2005 | Jacobs | |
| 2005/0197699 A1 | 9/2005 | Jacobs et al. | |
| 2005/0209542 A1 | 9/2005 | Jacobs | |

FOREIGN PATENT DOCUMENTS

| | | |
|---|---|---|
| WO | WO 00/49983 | 8/2000 |

OTHER PUBLICATIONS

PCT/US03/18753.
U.S. Appl. No. 09/766,939, filed Jan. 22, 2001, Enzerink et al.
U.S. Appl. No. 10/246,174, filed Sep. 17, 2002, Jacobs et al.
U.S. Appl. No. 10/418,325, filed Apr. 17, 2003, Jacobs et al.
Dialog English abstract of French patent publication No. 2 744 623 published on Aug. 14, 1997, one page, located in Derwent file 351 on Mar. 25, 2002.

* cited by examiner

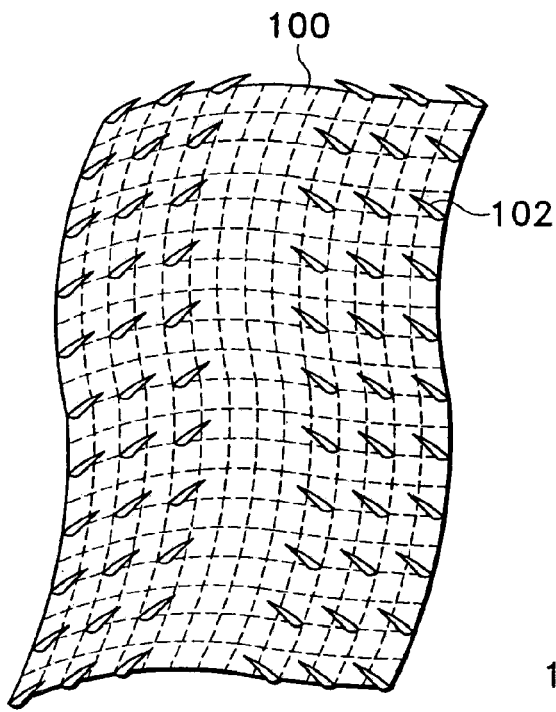
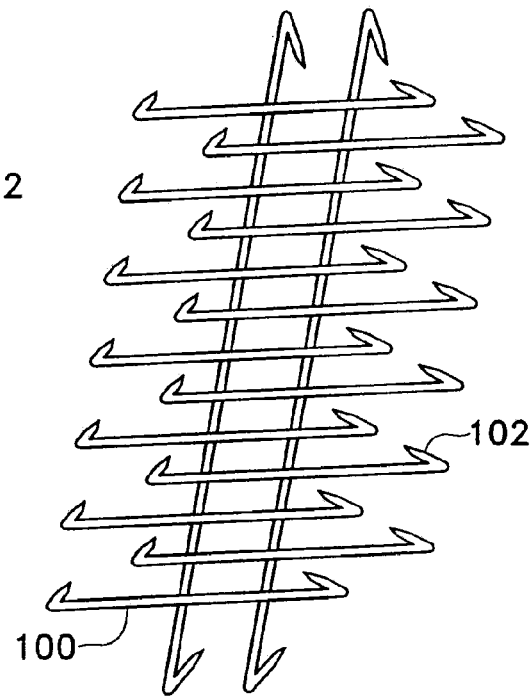
FIG. 1A  FIG. 1B
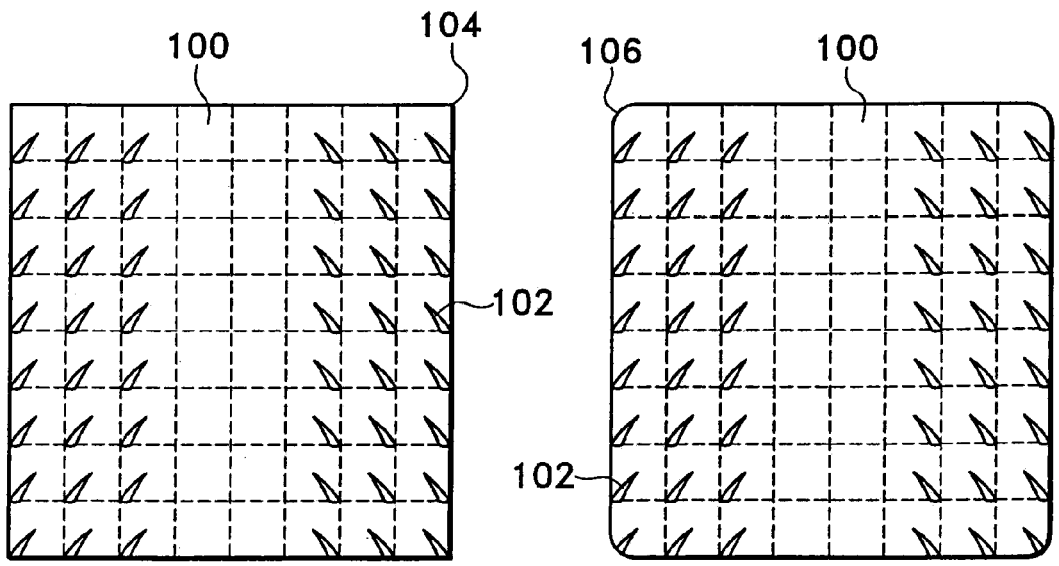
FIG. 1C  FIG. 1D

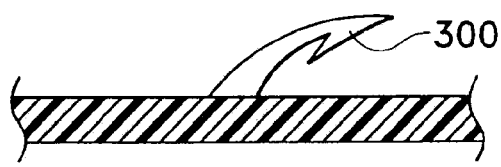
FIG. 3A
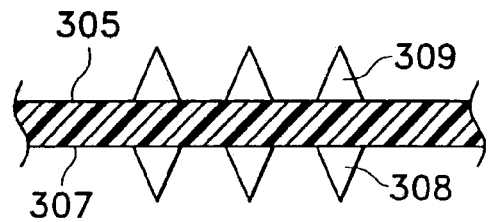
FIG. 3E
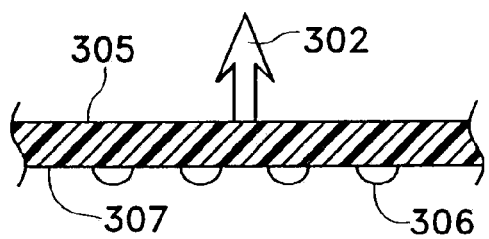
FIG. 3B
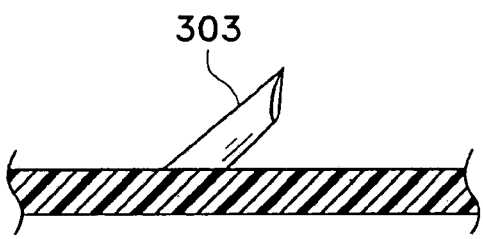
FIG. 3F
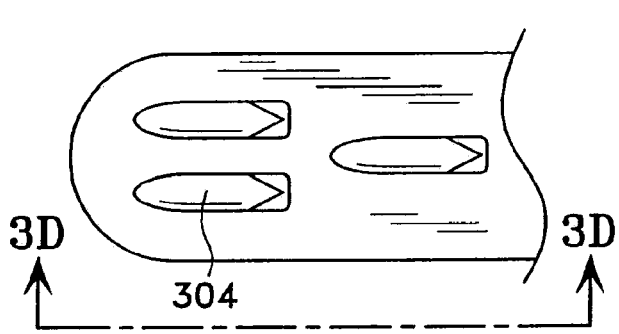
FIG. 3C
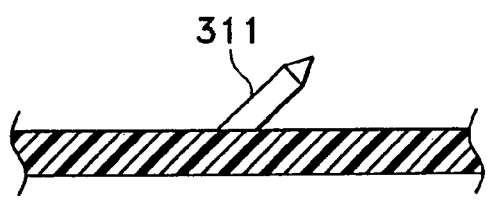
FIG. 3G
FIG. 3D
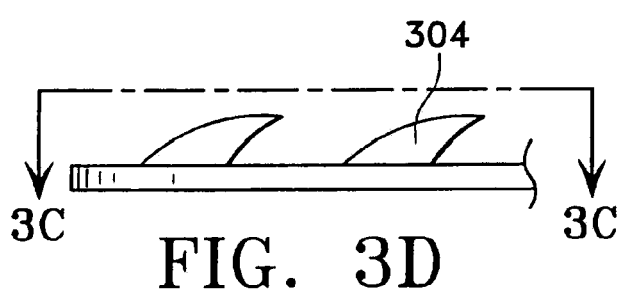
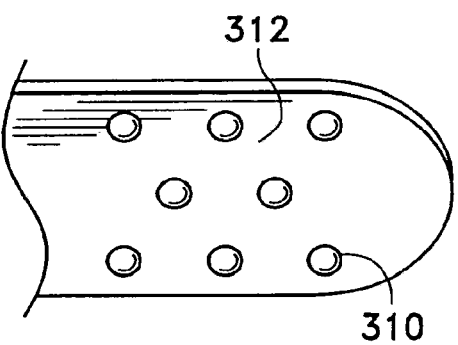
FIG. 3H

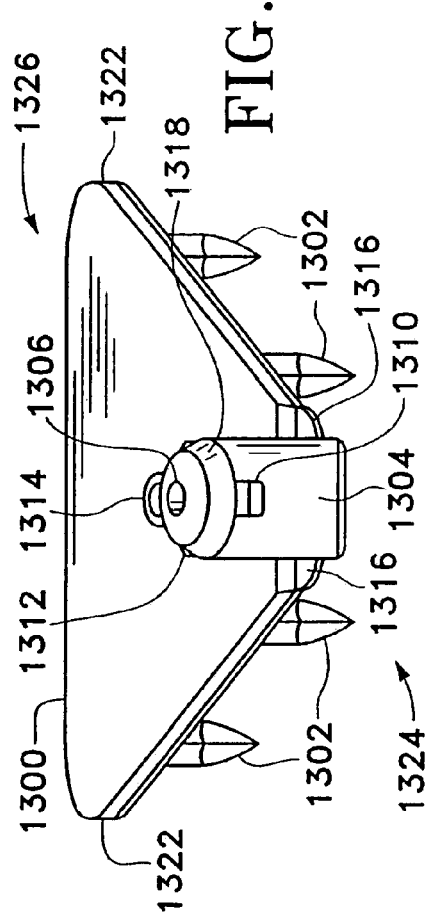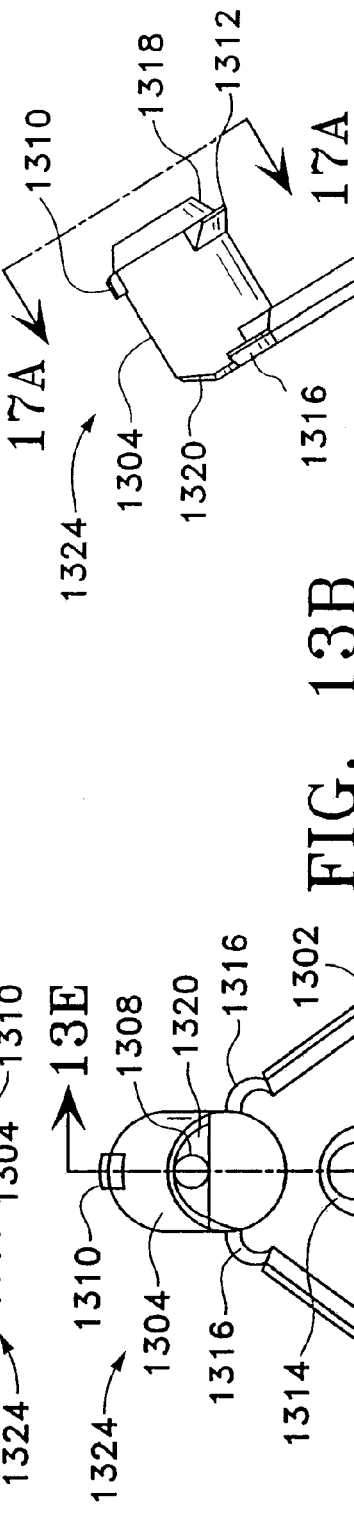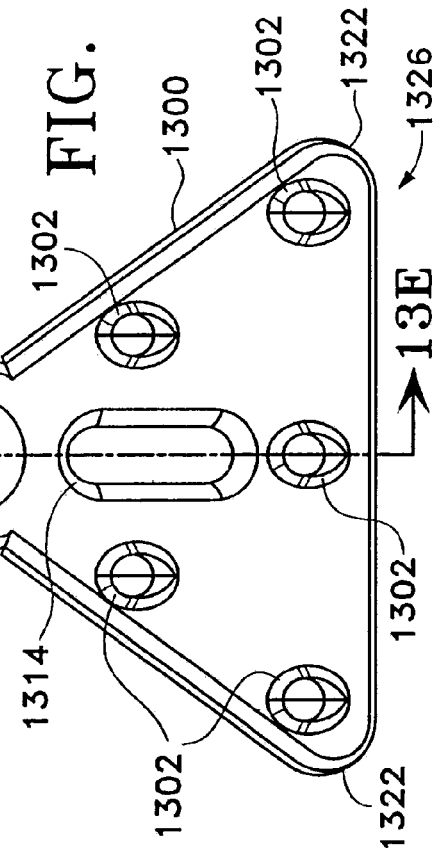
FIG. 13A
FIG. 13B
FIG. 13C

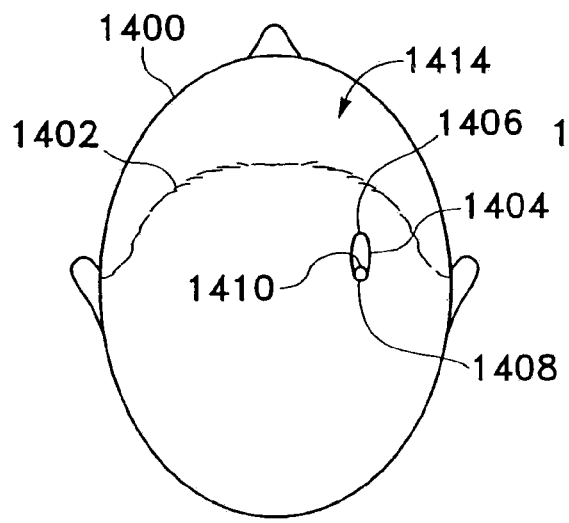
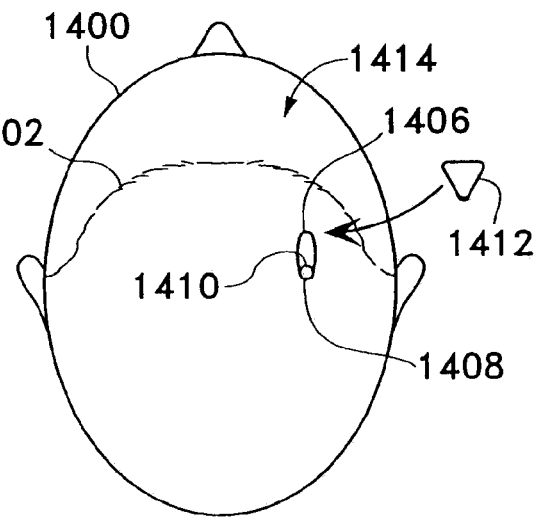
FIG. 14A  FIG. 14B
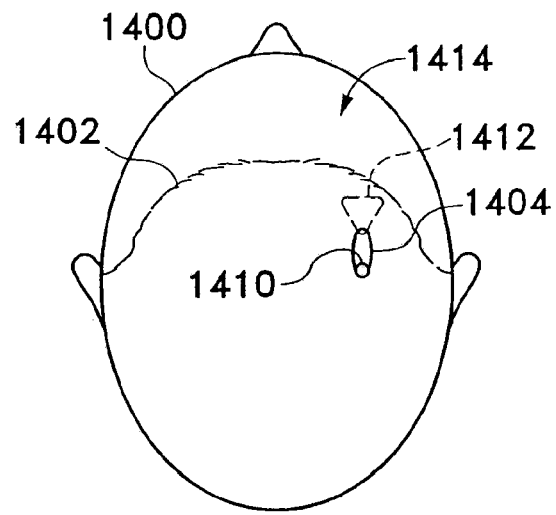
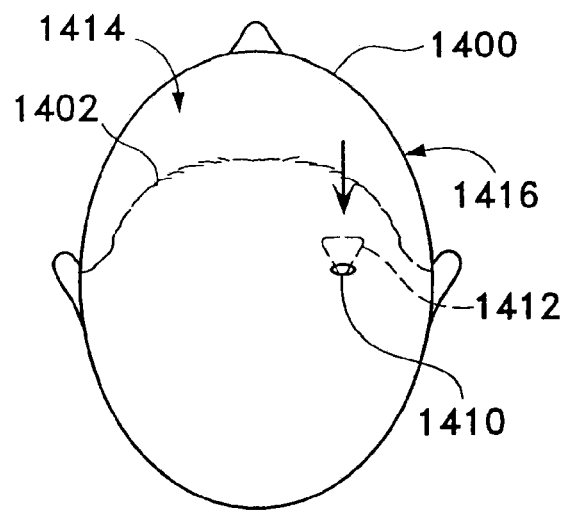
FIG. 14C  FIG. 14D
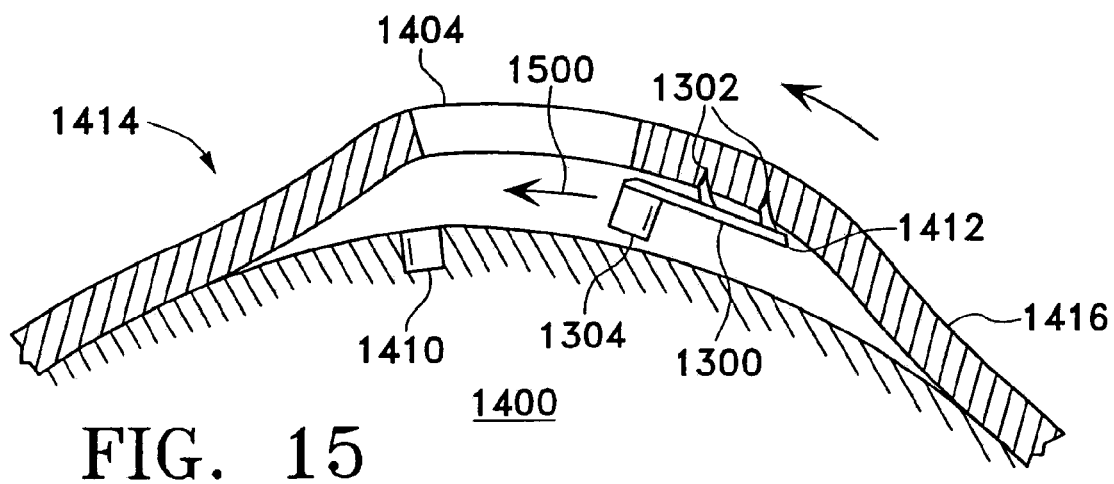
FIG. 15

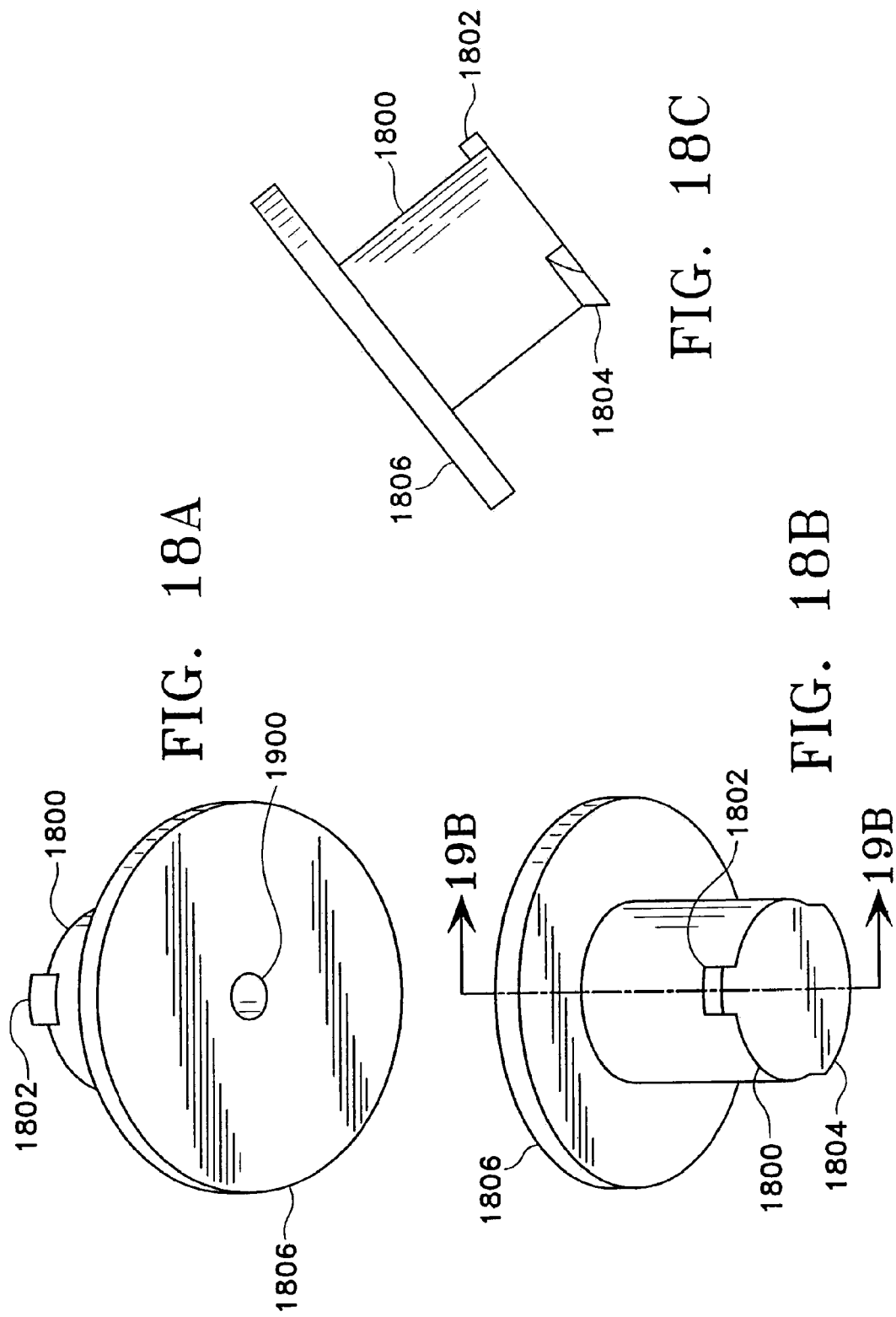

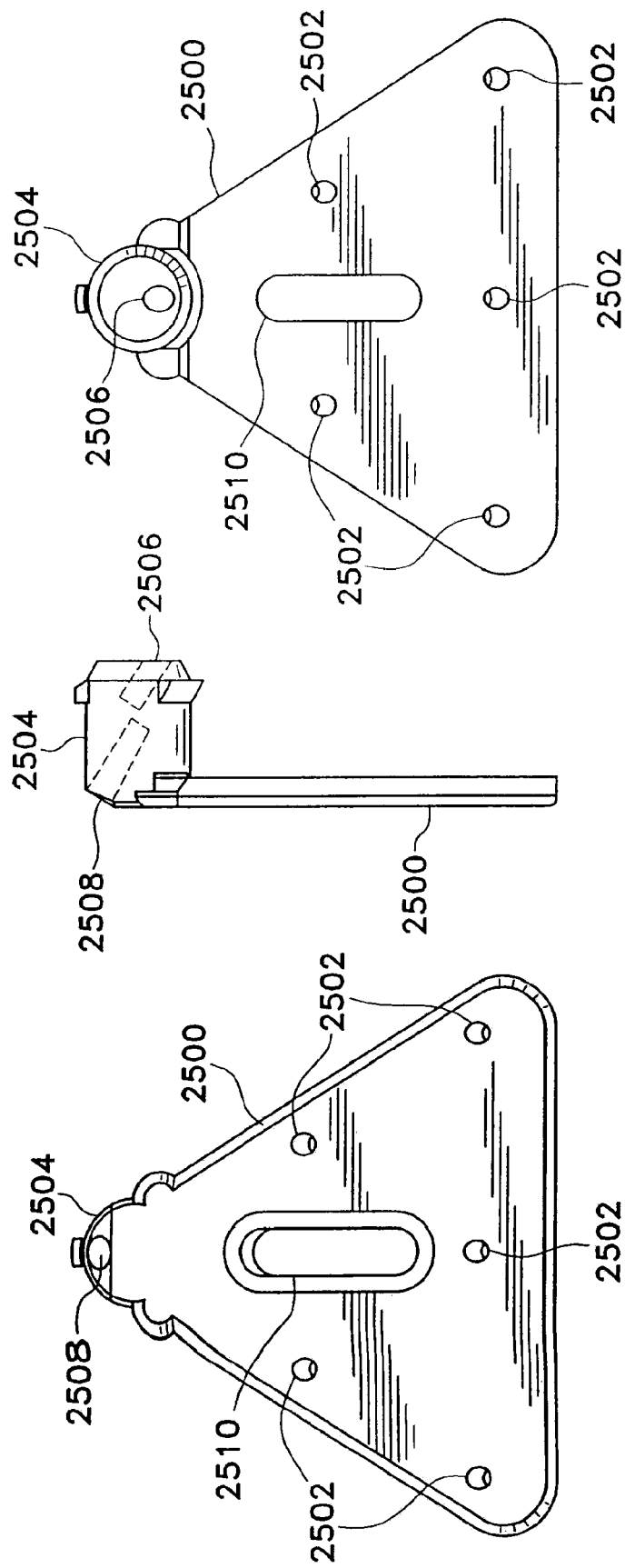

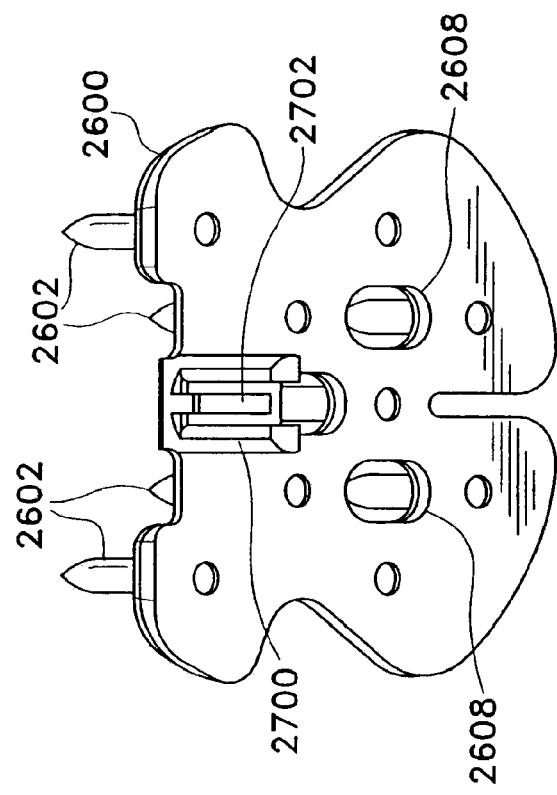
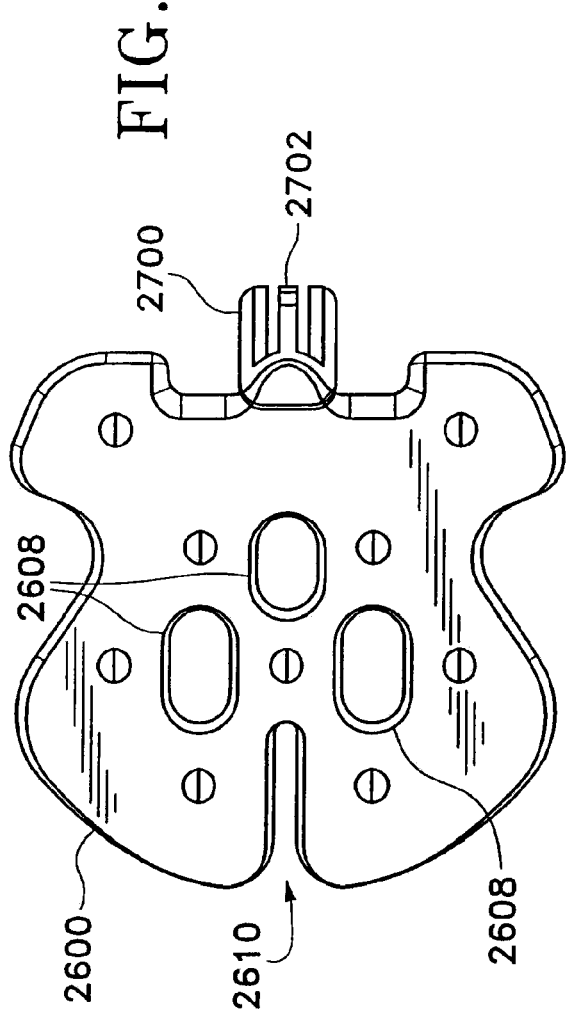
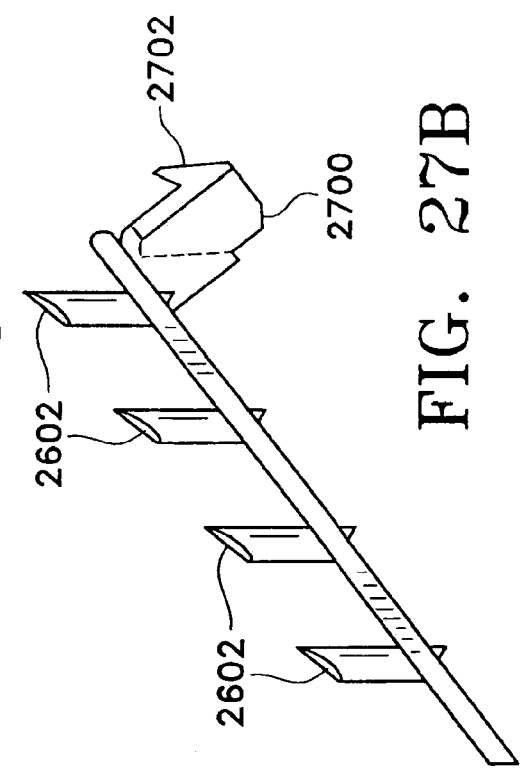

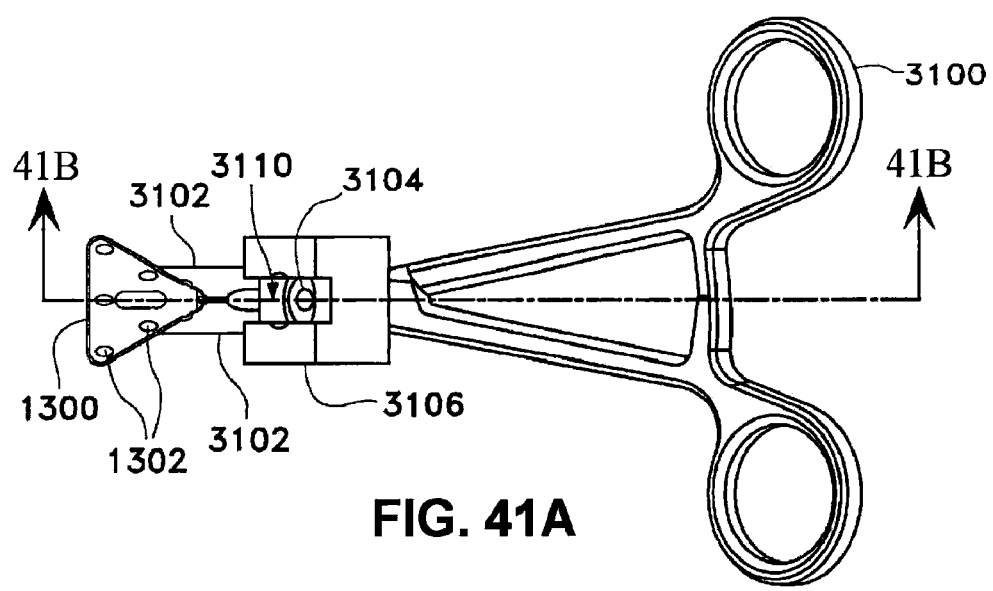
FIG. 41A
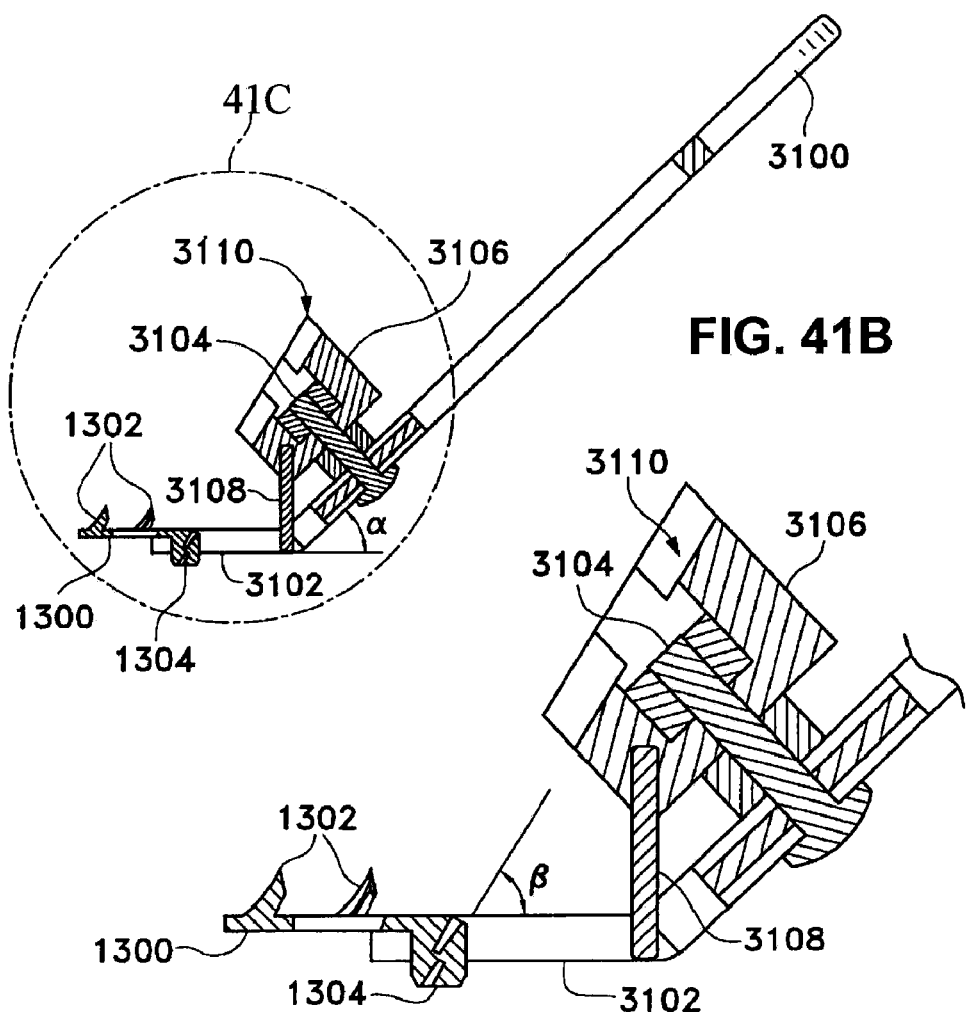
FIG. 41B
FIG. 41C

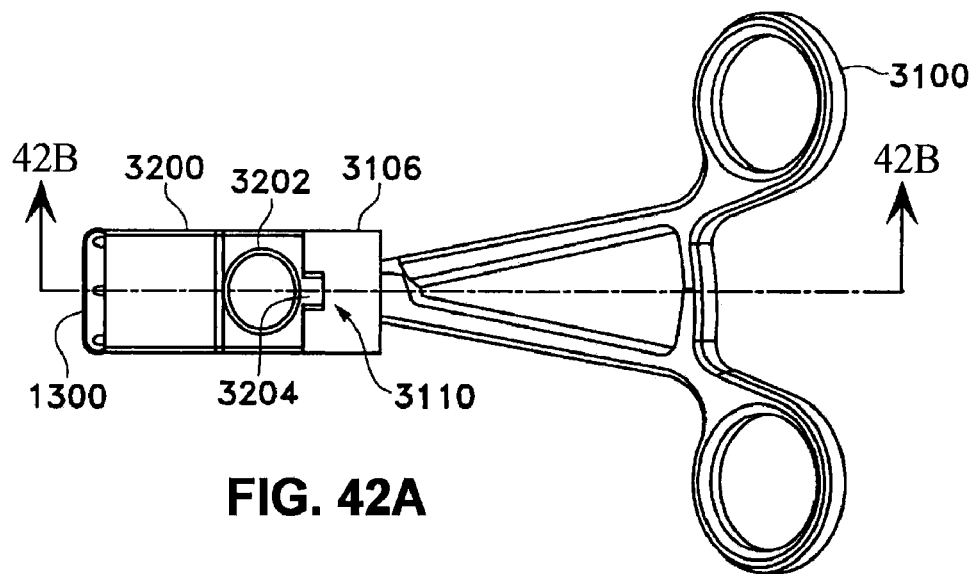
FIG. 42A
FIG. 42B
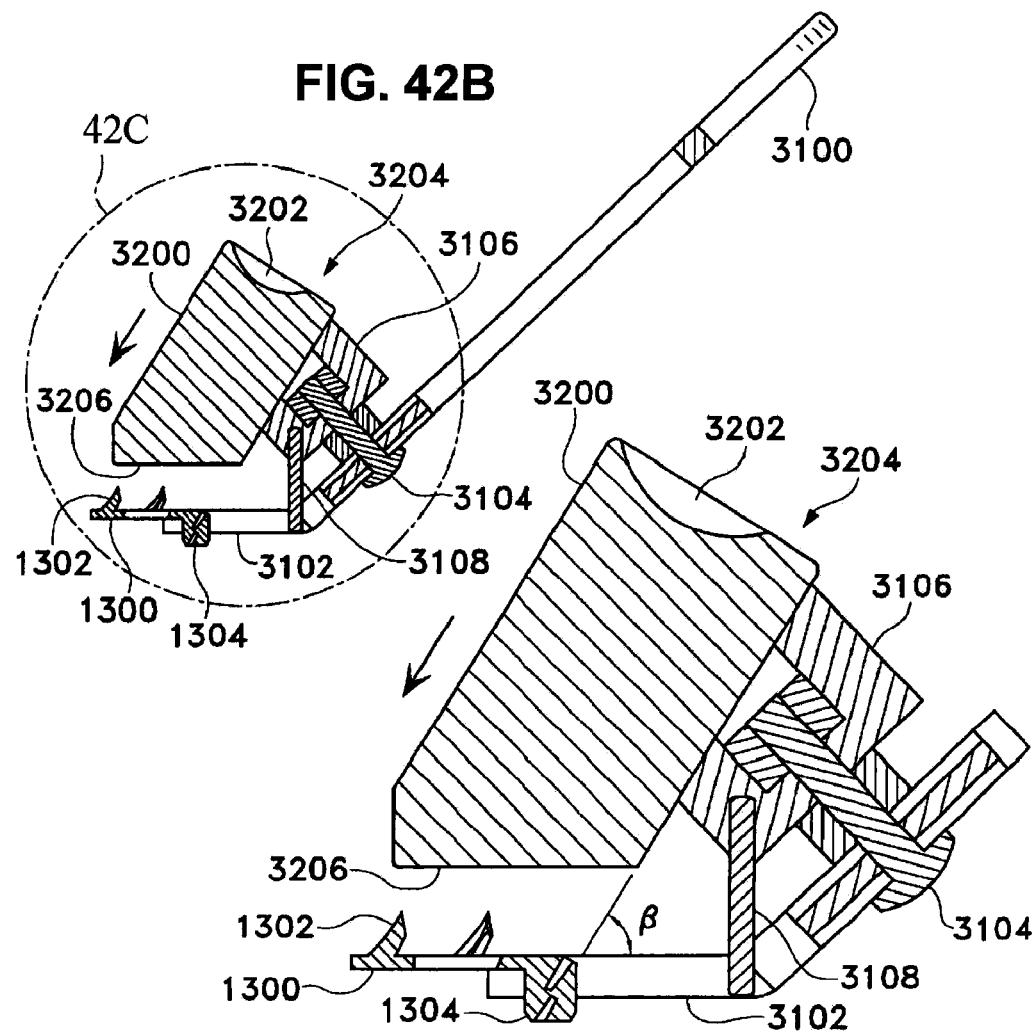
FIG. 42C

MULTI-POINT TISSUE TENSION DISTRIBUTION DEVICE AND METHOD, A CHIN LIFT VARIATION

CROSS-REFERENCE TO RELATED APPLICATIONS

This is a continuation-in-part of U.S. patent application Ser. No. 10/299,119 filed Nov. 18, 2002, which is a continuation of U.S. patent application Ser. No. 09/788,118 filed Feb. 16, 2001, which is a continuation-in-part of U.S. patent application Ser. No. 09/574,603 filed May 19, 2000, each of which is incorporated herein by reference in its entirety.

FIELD OF THE INVENTION

This invention is in the field of surgery. More particularly, it relates to a tissue approximation device. By "approximation" we mean to include variously the specific movement of two regions of tissue towards each other, the movement of one or more selected tissue regions or areas, the maintenance and/or fixation of one or more selected tissue regions in a selected position, and the maintenance and/or fixation of a selected area of tissue against shape variation due to tissue "springiness." We will also refer to these functions as "stabilization" of a tissue region. For instance, the inventive device may be used to facilitate wound healing by holding soft tissue together under improved distribution of tension and with minimal disruption of the wound interface and its nutrient supplies. Generally, the device has multiple sites for grasping said tissue using tines or prongs or other generally sharp, projecting points, extending from and preferably affixed to a single, supportive backing. Various processes of using the inventive device are also a portion of the invention.

BACKGROUND OF THE INVENTION

The inventive device is preferably used for the approximation, mobilization, or fixation of tissue. As noted above, these terms are meant variously to include the specific movement of two regions of tissue towards each other, the movement of one or more selected tissue regions or areas, the maintenance of one or more selected tissue regions in a selected position, and the maintenance of a selected area of tissue against shape variation due to tissue "springiness." Using our inventive device, a variety of approximation procedures may be achieved, variously from the movement of two tissue areas towards each other at a common wound margin to the maintenance of an area of tissue in a specific position during or after a surgical procedure, e.g. brow lifts or ACL regions.

For instance, our inventive device allows healing of soft tissue due to its maintenance of tissue position. The surgically induced healing of soft tissue wounds involves two phases, the mechanical phase of wound closure followed by the biochemical phase which involves protein bridging and scarring. In the mechanical phase, the edges of soft tissue are held in contact by essentially two components: 1) The physical properties and device-tissue interactions of the materials holding the tissue edges in contact, e.g. sutures or staples; and 2) An early deposition of proteinaceous material that has adhesive characteristics, e.g. fibrin glue.

Only in the biochemical phase, which occurs after the mechanical phase, do tissue components replace the mechanical components adhering the wound surfaces. During the biochemical phase, the inflammatory cascade generates signals which induce fibroblasts to migrate into the wound and synthesize collagen fibers.

Collagen is the primary constituent of connective tissue and ultimately determines the pliability and tensile strength of the healing wound. Tensile strength is gradually recovered; 60% of ultimate wound strength is achieved after approximately 3 months. However, this process is successful only if the previous mechanical phase has proceeded normally.

The surgeon's goal is to optimize the strength and often the cosmetic appearance of a wound closure or tissue coaptation. For this to happen, tissue is mechanically approximated until the wound has healed enough to withstand stress without artificial support. Optimal healing requires the application of appropriate tissue tension on the closure to eliminate dead space but not create ischemia within the tissue. Both of these circumstances increase the risk of wound infection and wound dehiscence.

Although the biomaterial composition of sutures has progressed considerably, the sophistication of manual suture placement in wounds has advanced relatively little since the original use of fabrics several thousand years ago to tie wound edges together. The wide tolerance ranges for suture placement, tension, and configurations, both amongst different surgeons and for different implementations by the same surgeon, result in a significant component of sub-optimal technique. Yet, the technique used for wound closure forms the foundation for all subsequent events in the healing process. It is during this mechanical phase that tissue tension is high, edema and inflammation are intense, wound edge ischemia is greatest, and that one can already observe the complication of wound failure.

Soft tissue is well known for its inability to hold tension. Even when optimally placed, sutures gradually tear through soft tissue, producing gaps in wounds and possibly leading to the eventual failure or sub-optimization of wound healing. Furthermore, since sutures require the implementation of high levels of tension to counteract the forces acting to separate tissues, they may strangulate the blood supply of the tissues through which they are placed, thus inhibiting the delivery of wound nutrients and oxygen necessary for healing.

There have been many attempts to construct wound closure devices that decrease closure time and improve cosmesis. U.S. Pat. Nos. 2,421,193 and 2,472,009 to Gardner; 4,430,998 to Harvey et al.; 4,535,772 to Sheehan; 4,865,026 to Barrett; 5,179,964 to Cook; and 5,531,760 to Alwafaie suggest such devices. However, these devices are not useful in surgical or deeper wounds. They only approximate the skin surface, joining skin edges variously through external approaches, using adhesives or nonabsorbable attachment points that penetrate tissue. The devices minimally improve the biomechanics of wound closure, and do not adequately approximate the deeper layers of the closure, i.e. fascia or dermis. Externally placed attachment points that puncture the skin lateral to the wound also interfere with long-term cosmesis and provide a possible conduit for infecting microorganisms.

U.S. Pat. No. 5,176,692 to Wilk et al., discloses a device for hernia repair that utilizes mesh with pin-like projections to cover hernia defects. This device, however, is used in a laparoscopic hernia repair in conjunction with an inflatable balloon. Closure devices for deeper tissues are described in U.S. Pat. No. 4,610,250 to Green; 5,584,859 to Brozt et al.; and 4,259,959 to Walker. However, these devices either work in conjunction with sutures, are made of materials that do not suggest biodegradability, or are designed in such a way as not to impart uniform tension on the closure, increasing the risk of wound separation and failure of wound healing.

The present invention is a biodegradable tissue approximation device. The device includes a plurality of attachment points, e.g. tines, prongs, or other generally sharp or blunt parts, connected to a backing that can be manipulated to close wounds, join soft tissue or bone, or create anastomoses. This multi-point tension distribution system (MTDS) device may be placed with minimal tissue trauma. The present invention typically incorporates the deeper layers of tissue within the closure, and the multiple attachment points distribute the resulting tension, often uniformly. Approximation from the internal aspect of the wound minimizes the potential for dead space in the closure, thus decreasing the risk of sub-optimal healing. Moreover, because the device is absorbed, a second procedure is not typically needed to remove the device.

Thus, the present invention improves the mechanical phase of healing by facilitating wound closure and/or the coaptation of tissues prior to initiation of the biochemical phase of wound healing. Placement of the device maximizes the chance for a good cosmetic result and is not heavily dependent on surgeon skill. Closure time is also shortened, decreasing overall cost and risk of operative complications.

SUMMARY OF THE INVENTION

The present invention is a device that improves the mechanical phase of wound healing. In the preferred embodiment, tissue edges are stabilized by a plurality of attachment points that extend from and are affixed to a supportive backing. The density, shape, length, and orientation of attachment points on the backing may be varied to suit the procedure, type of tissue being approximated, and/or area of the body involved. The flexibility of the backing is also variable and dependent on the materials used and dimensions of the backing. In function, the forces or tension placed upon the tissues by the inventive device are mirrored in the backing of the device. Said another way, the shape of the tines relay any forces to the backing of the device. The backing is generally in shear along its length. In the preferred embodiment, the device is biodegradable, and the attachment points uniformly distribute tension over the contact area between the device and tissue.

Processes of using the present invention are also provided. The device may be used to close wounds and create vascular anastomoses. The device may also be manipulated to approximate soft tissue and soft tissue to bone. The device may be used to mobilize, move, or stabilize a selected region or area of tissue, as noted above.

A further application may include approximation of soft tissue in brow lift and other craniofacial and maxillofacial surgical procedures. Such a device may be optimized to distribute loads over the device while the device remains attached to the patient's cranium. The brow lift device may further include multiple variations of the device, such as custom-fittable devices, and is preferably biodegradable and absorbable by the patient. The device may also be made from biological materials. The device may also optionally include coatings over the entire device or portions of the device to produce various biological effects, e.g., increased healing response, pain reduction, etc. A device variation may be installed into a patient by first creating an incision in the patient's scalp. This incision is preferably a predetermined length corresponding to the length of scalp or tissue desired to be lifted. At one end of the incision, preferably the end farthest away from the scalp or tissue to be lifted, the doctor or surgeon would drill a hole into the cranium. At the opposing end of the incision, the device may be inserted under the scalp or tissue which is then set on the device via attachment points affixed to the device surface. The surgeon may then lift the scalp or tissue via the device, which may then be secured to the cranium by inserting an anchoring post into the drilled hole. Alternatively, after the incision is made and the hole drilled in the cranium, the device may first be inserted into the hole via the post. The surgeon may then lift the scalp or tissue into position over the device and then set the lifted tissue onto the attachment points. Moreover, the device may utilize various types of coatings for selective placement over the device to effect various responses.

In either case, the procedures may be accomplished by a variety of methods. One particularly useful tool may comprise a manipulatable handle having opposing grasping arms. The grasping arms may be used to secure and handle the device via the anchoring post. The tool may include a slidable block which may be angularly disposed relative to the handle so that the block may press down and secure a portion of the scalp or tissue to be lifted. The block is preferably disposed angularly such that the angle of the block is similar to the angle of the attachment points affixed to the brow lift device. Angling the block may allow the tissue to be optimally set against the attachment points and may provide the least resistance to piercing the scalp or tissue. Alternatively, the tool may omit the slidable block completely and the tissue may be set against the attachment points by other methods such as simply pressing against the tissue by hand.

Another variation of the device may be used for chin lifts. The chin lift device may have a supportive backing which may be curved or bowed slightly such that it is configured to approximate a curvature of the underlying mandibular bone in the chin region of a patient. This device may also be configured to disperse the loading imparted by the tissue over an area sufficient so as to achieve desirable biological attachment and healing while the device remains attached to the patient's mandibular bone. The device may also be fabricated from a variety of biologically compatible materials as well as incorporate various coatings over the device, as described herein.

A deployment or installation tool may also be used with the chin lift device. Such a tool may have an attachment post for selectively engaging the chin lift device during installation into a patient.

BRIEF DESCRIPTION OF THE DRAWINGS

FIGS. 1A-1D are plan, perspective views of various MTDS devices.

FIGS. 3A-3D and 3F-3G are side views of various attachment points.

FIG. 3E is a side view of a two-sided MTDS device.

FIG. 3H is a plan, reverse perspective view of nubs on the inferior surface of a MTDS device.

FIG. 13A is a front view of a variation of a MTDS device having an integral post or anchor used in a brow-lift.

FIGS. 13B-13C are a top view and a side view, respectively, of the device of FIG. 13A showing the attachment points and integral post.

FIGS. 14A-14D show a top view of a patient's cranium during insertion of the device of FIG. 13A.

FIG. 15 is a cross-sectional side view of the insertion and securing procedure of the MTDS device from FIG. 14C.

FIGS. 18A-18C show back, front, and side views of a post variation missing a distal cavity.

FIGS. 25A-25C are top, side, and back views of another variation of the MTDS device which may receive separatable attachment points.

FIGS. 27A-27C are top, side, and back views of a variation of the MTDS device having a latching mechanism on the post.

FIG. 41A is a top view of a variation of the insertion tool showing the channel.

FIG. 41B is a view of cross-section 41B-41B from FIG. 41A showing an MTDS device and a side view of the support block.

FIG. 41C is a close-up view of the MTDS device and support block from FIG. 41B.

FIG. 42A is a top view of the insertion tool from FIG. 41A showing the block assembly.

FIG. 42B is a view of cross-section 42B-42B from FIG. 42A showing the MTDS device and a side view of the block assembly.

FIG. 42C is a close-up view of the MTDS device and block assembly from FIG. 42B.

DETAILED DESCRIPTION OF THE INVENTION

Figure 2A:
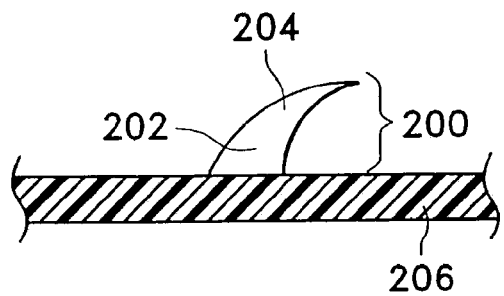
FIGS. 2A-2E are side views of various attachment point shapes and orientations.
Figure 2D:
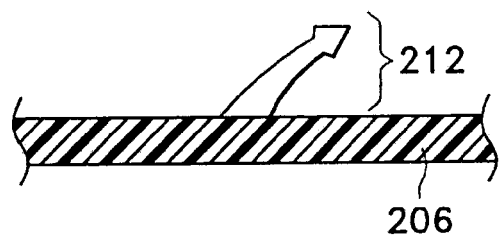
Figure 2B:
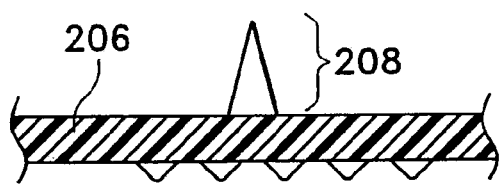
Figure 2E:
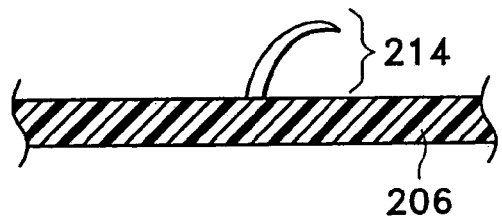
Figure 2C:
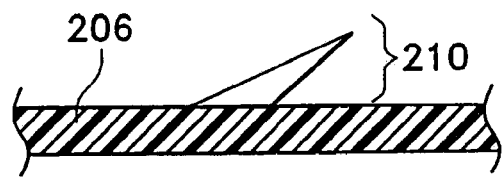

Our inventive device may be used when working with bone anchors or a variety of soft tissues. The device is of the general configurations shown in FIGS. 1A-1B and comprises a plurality of attachment points (102) emanating from and preferably affixed to a supportive backing (100) that is a generally a porous material that may have the structure of a mesh, net, or lattice. The degree of flexibility of the backing is determined by the material of construction, the shape and dimensions of the device, the type and properties of the approximated tissue, and the area of the body into which the device is placed. For example, a tightly curved or mobile part of the body, e.g., a joint, will require a more flexible backing, as would a tendon or nerve repair due to the amount of bending the device needs for the attachment. Also, depending on the type of material used, the thickness of the backing as well as its width and length may determine the flexibility of the device. Furthermore, the backing may be pre-fabricated into different shapes as shown by the sharp comers (104) and rounded comers (106) in FIGS. 1C and 1D. The fabricated cross-sectional shape and dimensions of the mesh elements may vary to promote flexibility in regions of the backing. The cross-sectional shape of the mesh elements may be chosen to minimize local compressive stress between the backing and surface it rests upon, or have rounded and filleted edges to be less obtrusive to local circulation. The plurality of attachment points distribute tension over the contact area between the device and the tissue. The tension or forces are generally also distributed in the tissue and in the backing parallel to the interfaces between the tissue and the device.

Materials such as biodegradable polymers are preferably used to construct the backing and attachment points. Polymers synthesized from monomers comprising esters, anhydrides, orthoesters, and amides are particularly suitable for biodegradation. Examples of biodegradable polymers are polyglycolide, polylactide, poly-α-caprolactone, polydiaxanone, polyglyconate, polylactide-co-glycolide, and block and random copolymers of these polymers. Copolymers of glycolic, lactic, and other α-hydroxy acids are highly desirable. Although we prefer to use a single polymer or copolymer in a specific device, generally for ease of construction, the invention is not so limited. An example of an inventive device may be made of two or more types of polymers or copolymers (or molecular weights of the same polymer or copolymer). For instance, the backing material might be produced from a more flexible polymer and the points or tines of a stiffer material. The inflammatory response to these polymers is minimal, and they have been safely used in suture materials, stents, drug delivery devices, orthopedic fixation devices, and intestinal anastomotic rings.

Generally, we will refer to the attachment points as "tines" or "prongs". These tines will refer both to points which are either sharp, i.e. able to separate tissue in a chosen use, or blunt, i.e. not able to separate tissue in that use. The attachment points may also be referred to as "barbs" when those points have the retaining point shown in several of the Figures discussed below. Generally, the tines, prongs or barbs penetrate into soft tissue and for a short distance. The attachment points preferably do not traumatize tissue in any major way, e.g., by penetration through a selected area of tissue to meet another device on the opposite side of the tissue. For instance, the attachment points generally do not penetrate the subject soft tissue more than 0.100". The attachment points may be considered to interlock with modulation in the adjacent soft tissue rather than penetrate as by a pin or bolt.

As shown in FIGS. 2A-2E, the shape of the attachment points or barbs may be varied depending, e.g., on the area of the body involved and the type of tissue requiring closure or reapproximation. The tines may be canted or erect, but in a preferred variation, the general structure of the tines is of a rose thorn shape. As shown in FIG. 2A, the tines (200) have a wide base (202) that supports a projection (204) from the backing (206) against the degree of tension required to close a wound or approximate tissue. For example, the attachment points may be erect tines (FIG. 2B-208), canted tines (FIG. 2C-210), canted arrowheads (FIG. 2D-212), canted hooks (FIG. 2E-214), or may have a single straight cross-section (FIG. 3G-311) that is nail-like, that does not vary over the length of the prong, for example, similar in shape to a nail or sharpened pencil. Furthermore, the tip of the attachment points may be varied as shown in FIGS. 3A-3D. The tips may be barbed (300 in FIG. 3A), arrowhead (double-barb) (302 in FIG. 3B), or cheese grater (304 in FIG. 3D). A side view of the cheese grater tips is shown in FIG. 3D. A faceted tip (303 in FIG. 3F) is shown. The faceted tip is especially desirable where the force to penetrate tissue is normal to the tissue surface.

The connection of the prong to the backing may be rounded or filleted, or the backing built-up around the prong, to reduce structural stress concentrations. The backing or connecting structure may branch out away from the center, with each branch in turn branching to grapple tissue in a distributed fashion. All edges of the device may be smooth except where sharpness is needed at the tip of the prong to pierce into the tissue. Once the prongs pierce into the tissue, the tissue may become supported against the backing to minimize additional piercing or irritation by the prong tip. The device may be molded, stamped, machined, woven, bent, welded or otherwise fabricated to create the desired features and functional properties.

The MTDS device may also have attachment points both on its front side (305), and on a back side (307). As shown in FIGS. 3B and 3E, the front and back sides have attachment points. The attachment points on the front side (309) generally approximate tissue. The attachment points on the back side (307) are auxiliary attachment points that may comprise forms such as round nubs (306) or pointed nubs (308). The auxiliary attachment points may be used to secure or promote stable implantation of the device. Soft tissue may be gently pressed into open regions of the backing thereby helping to fix the device in place against both underlying and overlying tissue after the modulation or interlocking of skin. FIG. 3H shows a reverse view of the nubs (310) on the back side of the device (312). The attachment points on a two-sided device are not limited to the combinations disclosed above, but may comprise any combination of the previously mentioned attachment point shapes and orientations.

Figure 4A:
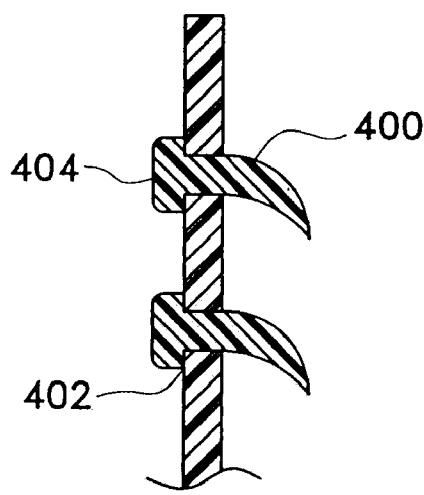
FIG. 4A is a side, cross-sectional view of attachment points that run through the width of a backing.
Figure 4B:
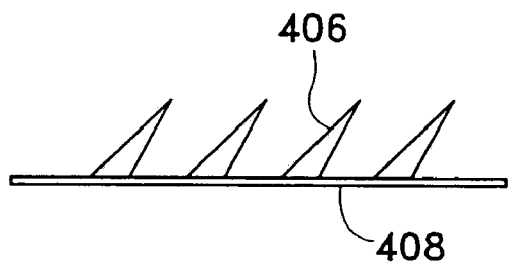
FIG. 4B is a side view of attachment points on a strip of backing material.
Figure 4C:
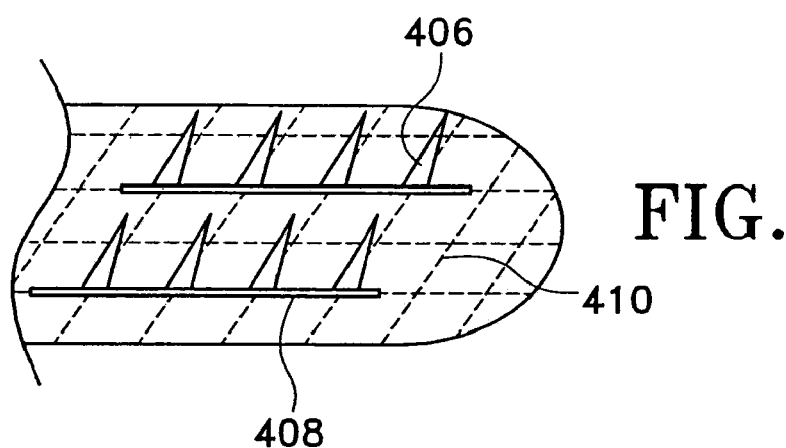
FIG. 4C is a plan, perspective view of the embodiment in 4B on a backing.
Figure 4D:
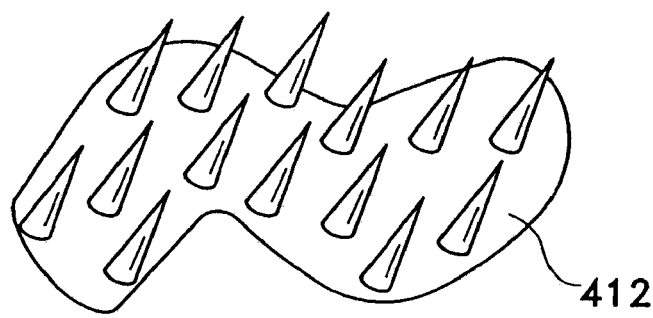
FIG. 4D is a plan, perspective view of attachment points on a solid backing.

Structural variations can also be made to the backing of the device. As shown in FIG. 4A, the attachment points (400) may be placed through a plurality of openings in the backing (402) and secured to the backing by a flange (404) or hub. In FIGS. 4B and 4C, the points (406) may also connect to strips (408) of the same material as the attachment points which are then secured to a backing (410). The backing may also be comprised of a solid material (412) instead of a porous material.

The extent of porosity, or total surface area may be used to control the absorption rate of the device, and may also be used to optimize the strength-to-mass properties of the device, increasing the section modulus of structural cross-sections per unit mass. The backing structure may comprise partial folds, waves or grooves to help hold tissue against both surfaces of the backing. Regions of the backing may function as suction cups to help hold tissue to the backing.

Figure 5A:
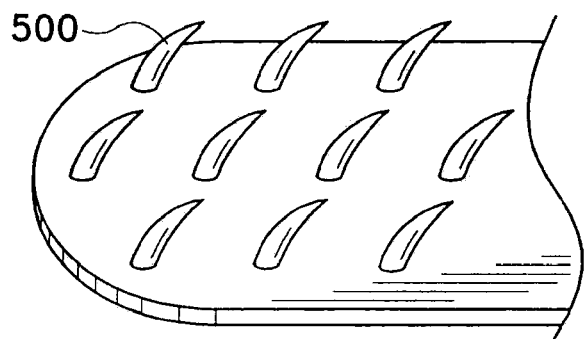
FIG. 5A is a plan, perspective view of attachment points canted in one direction.
Figure 5B:
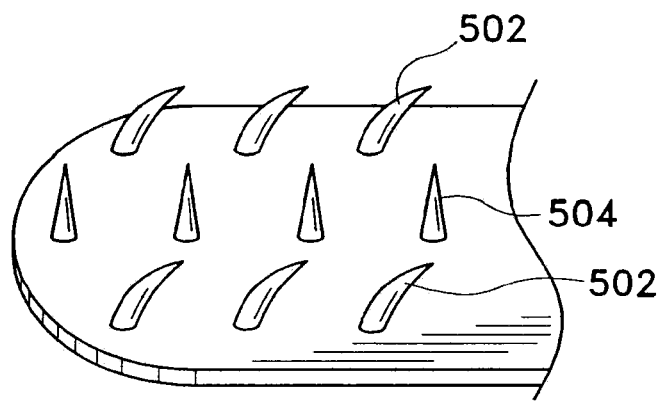
FIGS. 5B-5D are plan, perspective views of attachment points with various orientations on a backing.
Figure 5C:
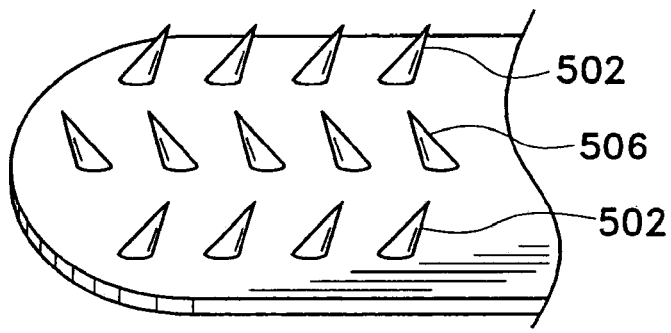
Figure 5D:
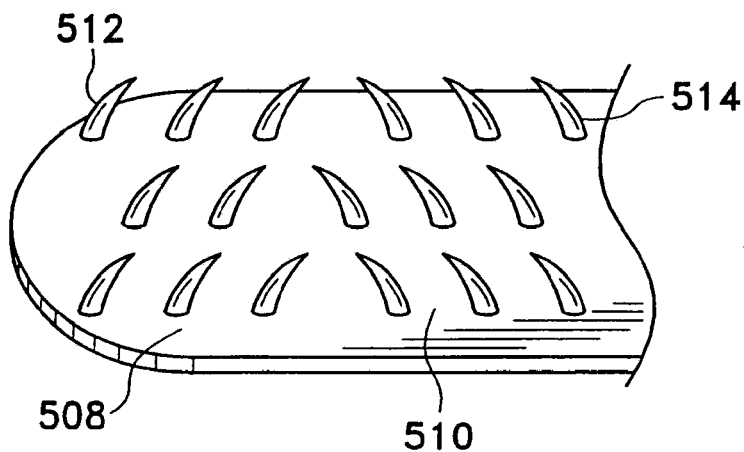

The density, distribution, length, and orientation of attachment points on the backing may be modified depending on the type of wound closure. Attachment points may be bent or curve gradually, with the tip directed at an optimal angle relative to the backing to aid device penetration and stability within the tissue, and to reduce tissue irritation after device installation. Attachment points may be canted in one direction (500), such as toward the center of the device as shown in FIG. 5A. The attachment points may also be variously oriented, such as toward center (502) and erect (504), or toward center (502) and away from center (506). It is within the scope of this invention to have attachment points extending in any relative direction or orientation on the backing. Or, as shown in FIG. 5D, the backing is divided into a first area (508) and a second area (510). Attachment points in the first area (512) and second area (514) are canted toward each other. The inventive device may also be sectioned into a plurality of areas, with each section being variously oriented to another section.

Figure 5E:
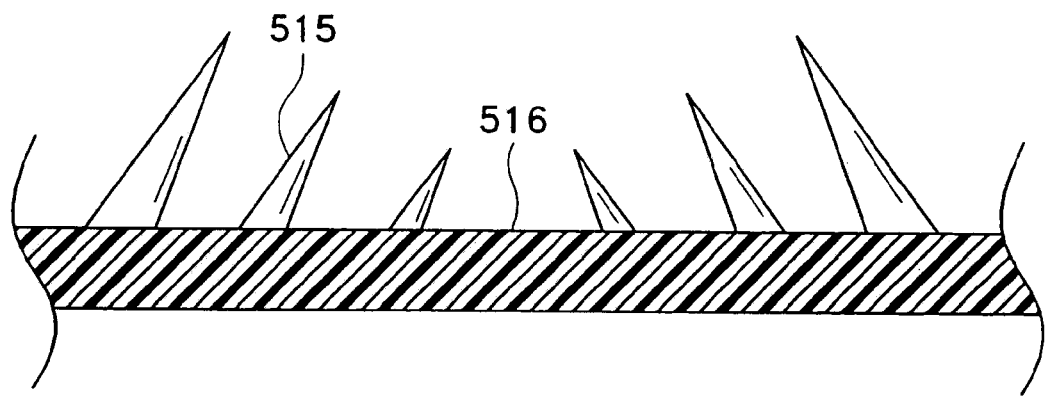
FIG. 5E is a side view of attachment points becoming progressively shorter the closer they are to the center of the device.
Figure 5F:
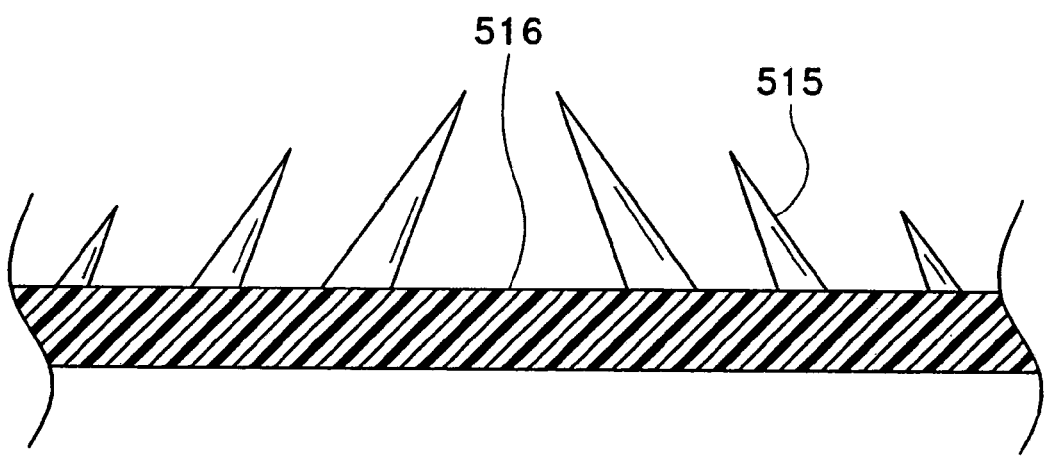
FIG. 5F is a side view of attachment points becoming progressively shorter the farther they are from the center of the device.

In another variation of the invention, attachment points of various lengths emanate from a single backing. For example, in FIG. 5E, the attachment points (515) are progressively shorter the closer they are to the center of the device (516). The attachment points (515) may also become progressively shorter the farther they are from the center of the device as shown in FIG. 5F. The variations shown in FIGS. 5B and 5C have regions of attachment points canted toward the center (502) and with other regions of attachment points with erect points (504 in FIG. 5B) or canted away from the other end (506 in FIG. 5C) of the device. These variations are more difficult to dislodge when situated in an area of the body having both to-and-fro movement, e.g., the inside of an elbow or back of the knee, or during placement of the device.

Figure 6A:
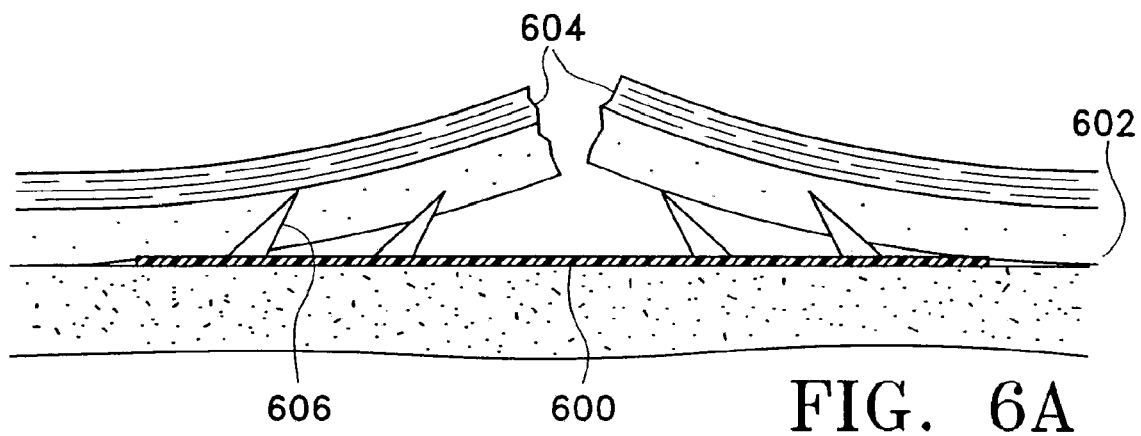
FIGS. 6A-6B are schematic views of a skin wound and wound repair using the MTDS device.
Figure 6B:
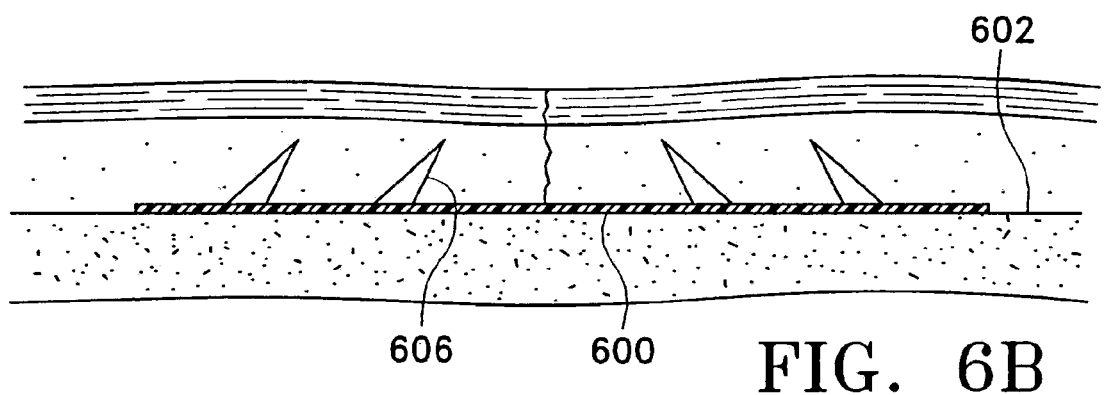
Figure 7:
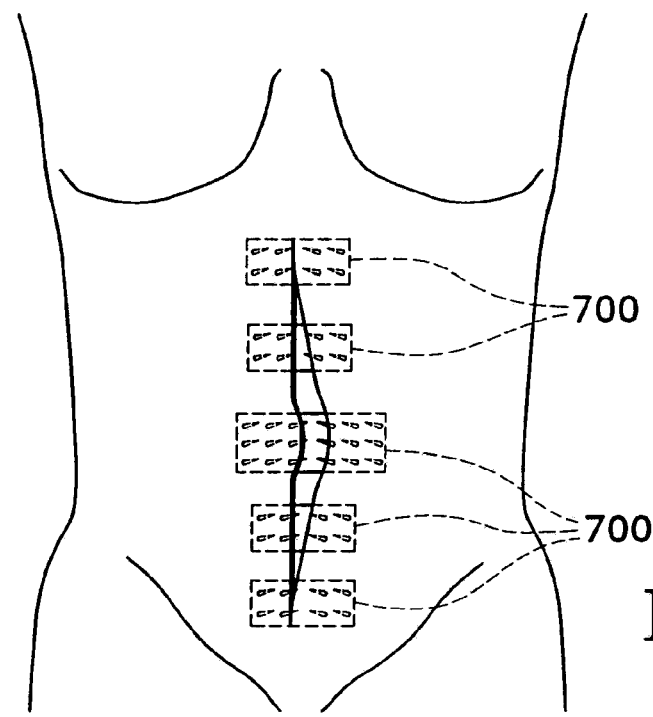
FIG. 7 is a schematic view of an abdominal wound closure using MTDS devices.

Portions of simple wound closures are shown in FIGS. 6A-6B. These wound closures involve placing the MTDS device (600) at the bottom of the wound, usually at the level of the sub-dermis (602). The edges of the wound (604) are approximated and then secured by fixation, e.g., by pressing, to the multiple attachment points (606). An example of the MTDS device placement in a laparotomy closure is shown in FIG. 7. The increased length of this incision requires placement of multiple devices (700).

Figure 8A:
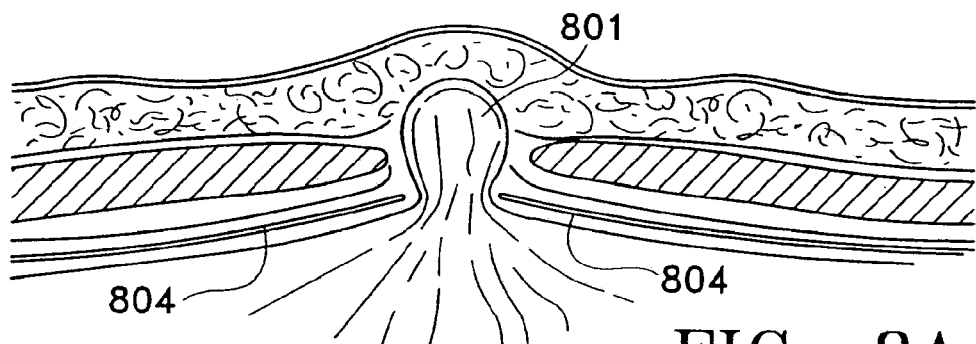
FIGS. 8A-8B are schematic views of an abdominal hernia and hernia repair using the MTDS device.
Figure 8B:
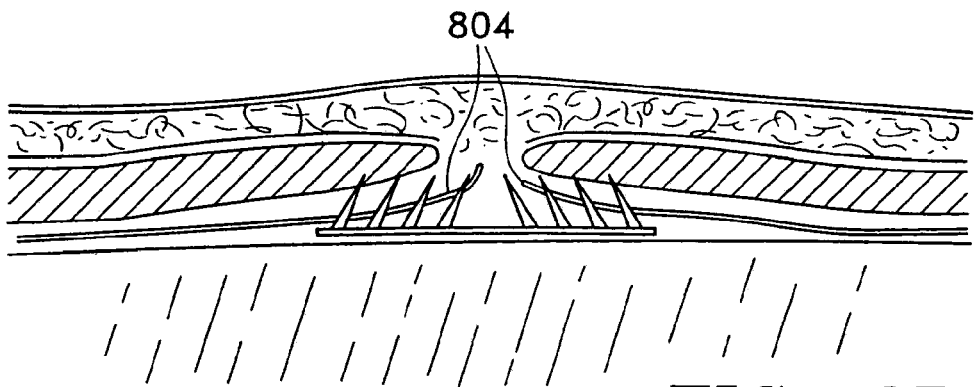
Figure 8C:
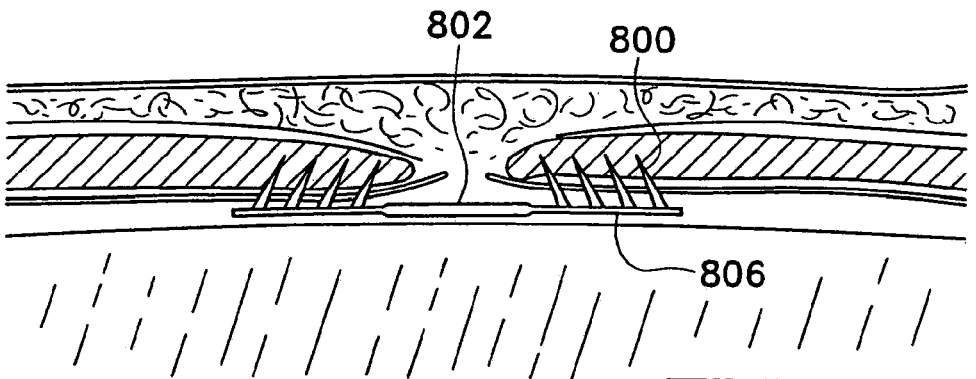
FIGS. 8C-8D are side and schematic views, respectively, of a MTDS device with attachment points on the edges of the backing and a central area without attachment points.
Figure 8D:
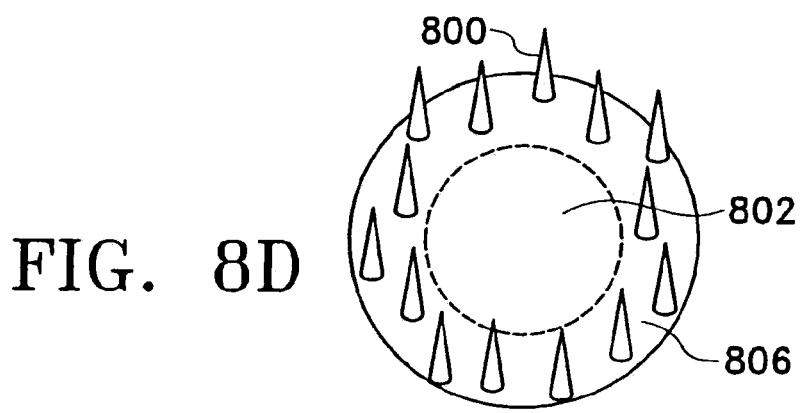

A unique application of this device occurs in hernia repair in which case the biomaterials are not absorbable but rather are more likely to be PTFE and POPU ("Gore-Tex"), polypropylene, or other permanent implant material. Once the hernia (801) is reduced, a MTDS device may be used to close the hernia defect by joining the edges of the separated fascia (804) as seen in FIGS. 8A and 8B. However, the device may also be modified to aid repair of a difficult hernia resulting from such circumstances as operating on an obese patient or large hernia, or having a wide fascial debridement where the fascial edges cannot be brought together. FIGS. 8C and 8D are variations of the inventive device that may be used in these cases. The attachment points (800) are secured to the ends of the backing (806) and are still used to adhere the device to tissue, but the points are spaced so that the central area of the backing is a flat surface without points (802) that covers the defect. The device in FIG. 8D is preferably used in an incisional hernia repair.

Figure 9A:
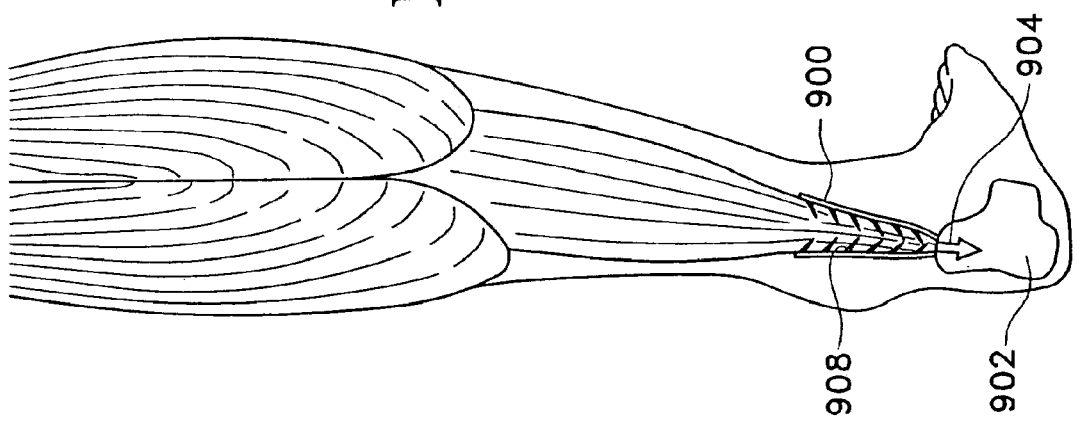
FIGS. 9A-9B are schematic views of a ruptured tendon and tendon to bone repair using the MTDS device.
Figure 9B:
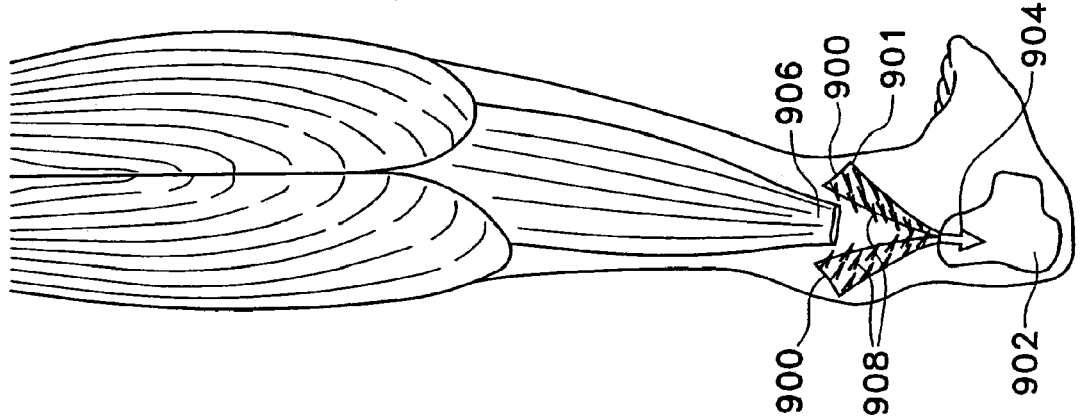

The MTDS device may also be constructed to reattach soft tissue such as tendons and ligaments to bone, as well as other soft tissue such as cartilage and the free ends of vessels or nerves. In FIG. 9A, the inventive device functions similar to a clamp. Backings with attachment points (900) are sides of a clamp that has a first end (901) and a second end (904). The first end (901) grasps tissue and the second end (904) is an anchor for tissue. For example, a ruptured tendon (906) may be fixed to the attachment points (908) of the first end of the clamp (901) and approximated to bone (902) with an anchor such as a pin or nail at the second end of the clamp (904), as seen in FIG. 9B. After mechanical fixation of the tissues, the biochemical phase of the wound healing process will begin, eventually forming a natural union between tendon and bone. Ligament and cartilage to bone unions using the MTDS device would undergo the same mechanical and biochemical processes.

Figure 10A:
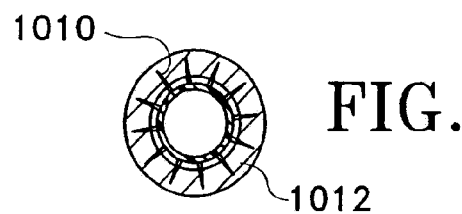
FIG. 10A is an axial view of a cross-section of a vessel repaired with the MTDS device.
Figure 10B:
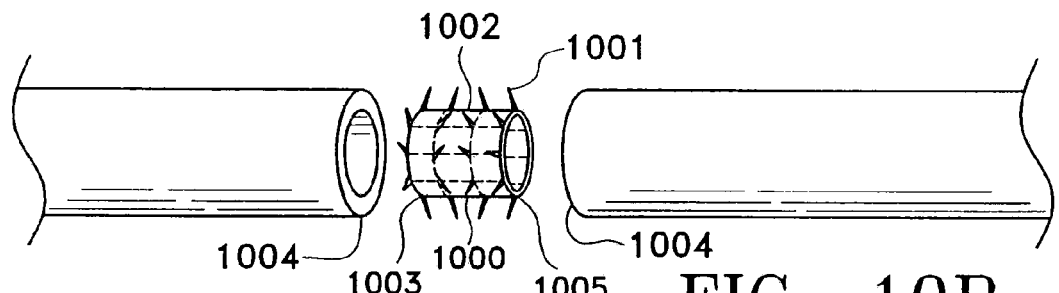
FIGS. 10B-10C are side, schematic views of vessel free ends and a vascular anastomosis using the MTDS device.
Figure 10C:
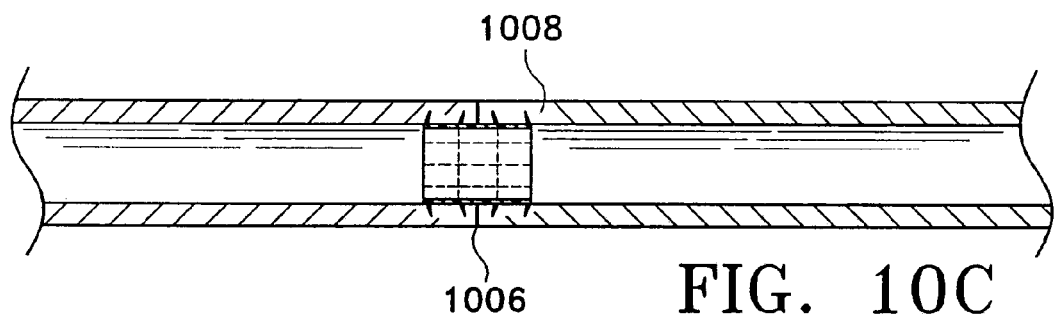

Vascular anastomoses may also be constructed with the MTDS device. In FIG. 10B, the backing has a tubular shape (1000) with attachment points (1001) on the outside surface (1002). The outside surface (1002) has a first end (1003) and a second end (1005) that opposes the first end (1003). The free ends of a vessel(s) (1004) are placed over the device, creating an anastomosis (1006) that is secured by attachment points fixed into the wall of the vessels (1008). The attachment points are preferably pointing towards the anastomosis (1006), with the attachment points on the first end (1003) being canted toward the second end (1005) and vice-versa. An axial view of the relationship of the attachment points (1010) to the vessel wall (1012) is shown in FIG. 10A.

Figure 11A:
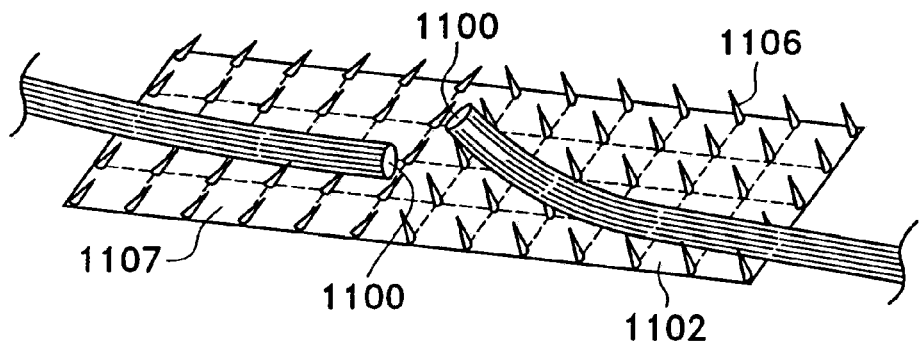
FIGS. 11A and 11B-11C are schematic, side, and cross-sectional side views, respectively, of a transected tendon and a tendon to tendon repair using the MTDS device.
Figure 11B:
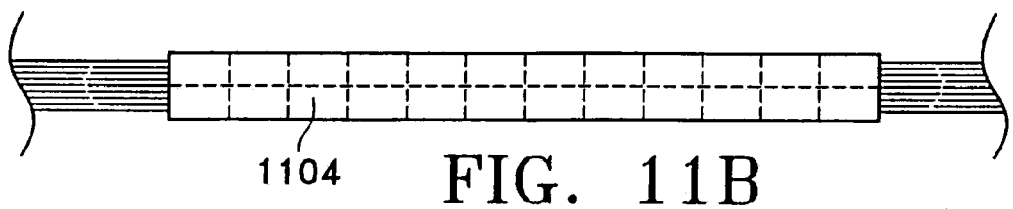
Figure 11C:
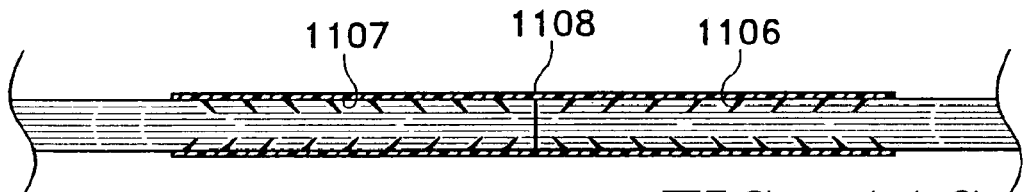
Figure 11D:
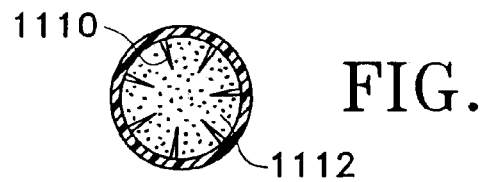
FIG. 11D is an axial, cross-sectional view of the MTDS tendon to tendon repair.
Figure 11E:
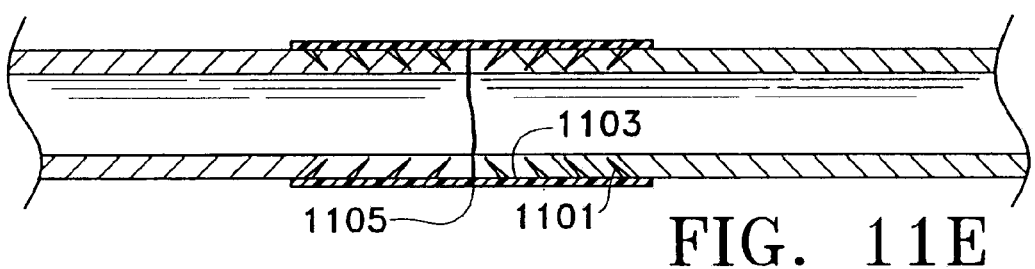
FIG. 11E is a side view of a vascular anastomosis using the MTDS device on the external surface of a vessel.
Figure 11F:
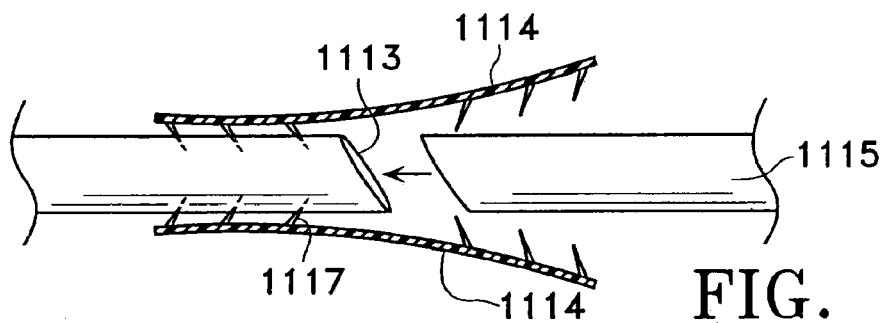
FIGS. 11F-11G are side, schematic views.
Figure 11G:
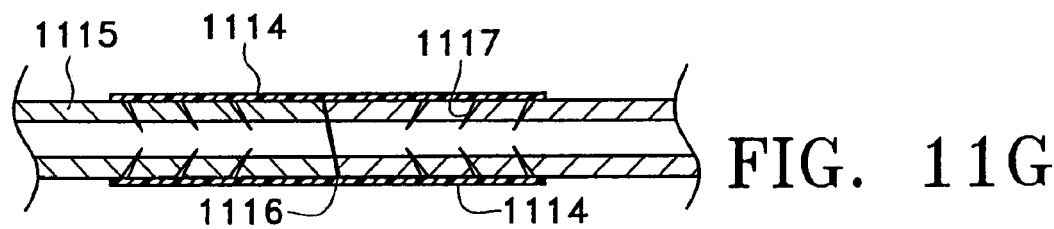
Figure 11H:
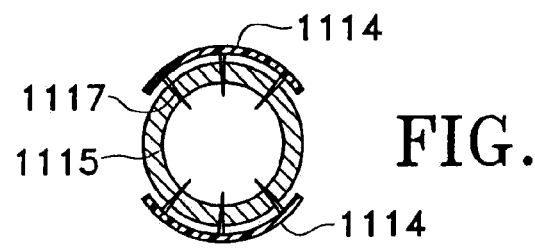
FIG. 11H is an axial view of the ends of a tubular structure being joined by externally placing strips of a MTDS device on approximated tissue.

Vessels and other soft tissue such as nerves, cartilage, tendons, and ligaments may also be joined as seen in FIGS. 11A and 11B. Two ends of tissue (1100) are brought and held together by the backing and attachment point construct (1102) being wrapped around the circumference of the tissue (1104). The attachment points (1106) are on the inside surface of the backing (1107) and secure the union at a central region (1108) as seen in FIG. 11C. An axial, cross-sectional view of the relationship between the attachment points (1110) and tissue (1112) is shown in FIG. 11D. The resulting form is, i.e., a tubular structure that has an inside surface (1107) with a central region (1108). The attachment points on the inside surface (1106) may be canted toward the central region (1108). FIG. 11E shows the device with attachment points (1101) on the inside surface of the backing (1103) being wrapped around vessel ends to create an anastomosis (1105). Instead of being wrapped around tissue, edges (1113) of tubular structures (1115) can also be joined by externally placing 2 or more strips of backing of a MTDS device (1114) on approximated tissue as shown in the side views of FIGS. 11F-11G, and the axial view in FIG. 11H. The attachment points (1117) also point toward the area of tissue approximation (1116).

Figure 11I:
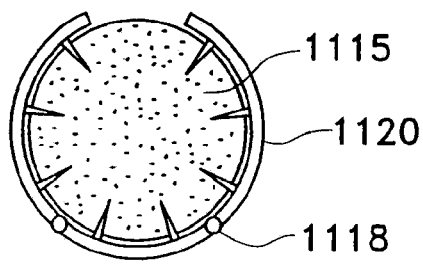
FIG. 11I is an axial view of a hinge in the backing of a device.
Figure 11J:
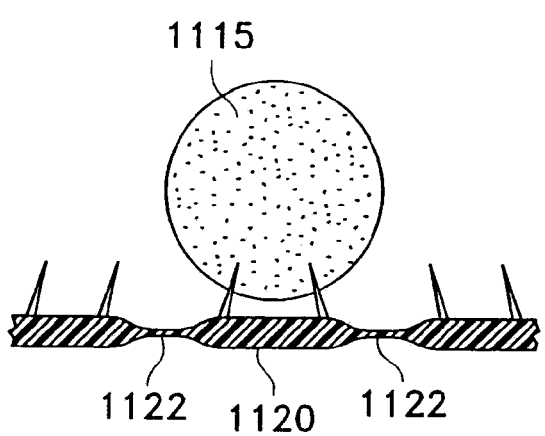
FIGS. 11J-11K are axial views of decreased backing material that are areas of enhanced device flexibility.
Figure 11K:
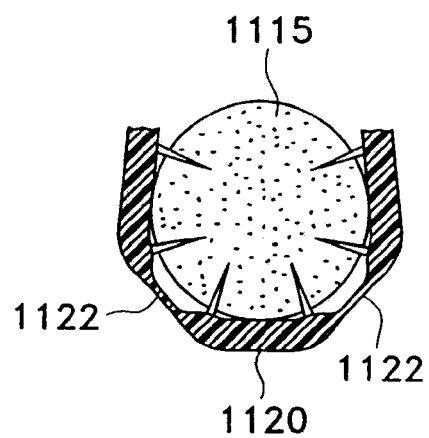
Figure 11L:
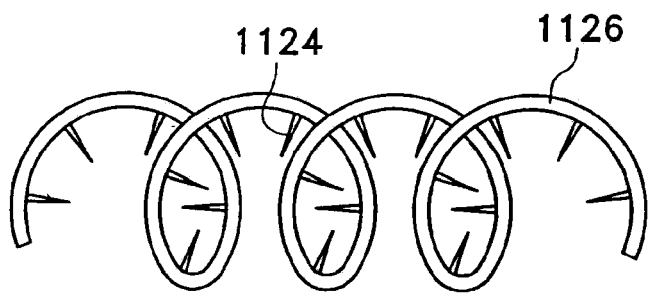
FIGS. 11L-11M are side views of a spring or coil-like MTDS device being used to approximate tissue.
Figure 11M:
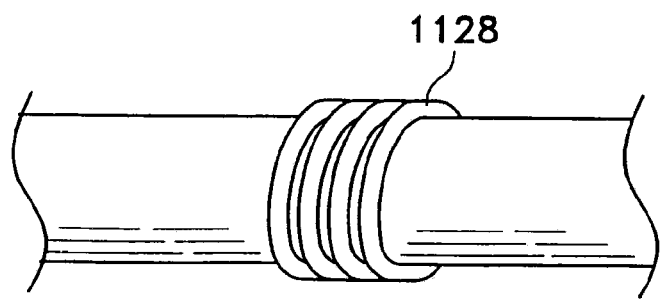

FIGS. 11I-11M are additional variations of the invention which vary the mechanisms used to improve device flexibility. In FIGS. 11I-11K, the backing has areas of comparatively higher flexibility than other areas of the backing. In an axial view of the variation in FIG. 11I, the backing is equipped with hinges (1118) that allow bending of the backing (1120) around tubular soft tissue structures (1115). In a second variation, the amount of material in the areas of the device that fold (1122) is reduced as shown in FIGS. 11J-11K. Another variation is seen in FIGS. 11L-11M where attachment points (1124) of a device extend from a backing in the form of a coil or spring (1126). The edges of soft tissue are approximated when the coil or spring is reduced (1128).

Device for Brow and Face Lift Procedures

Figure 12A:
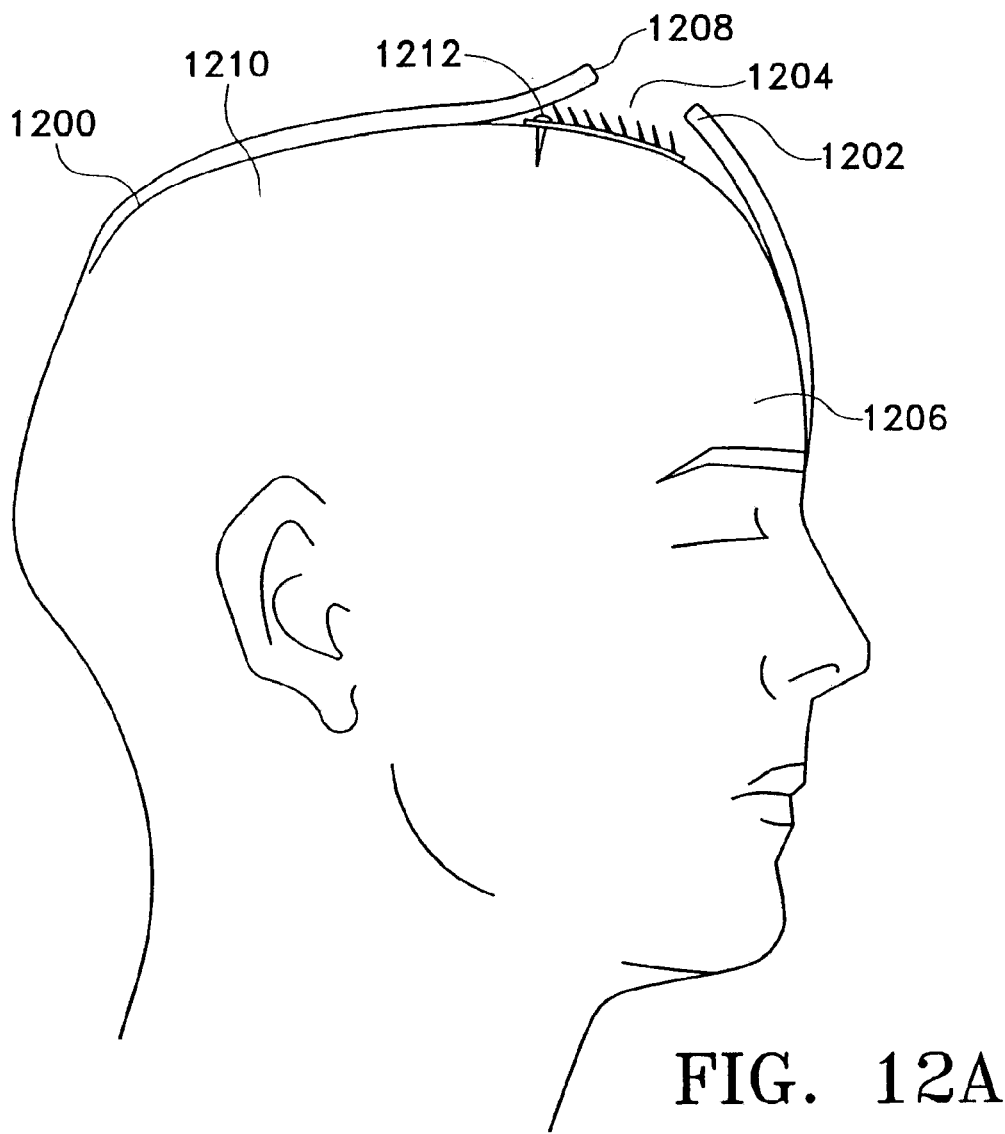
FIG. 12A is a schematic view of the MTDS device being used in a brow-lift procedure.
Figure 12B:
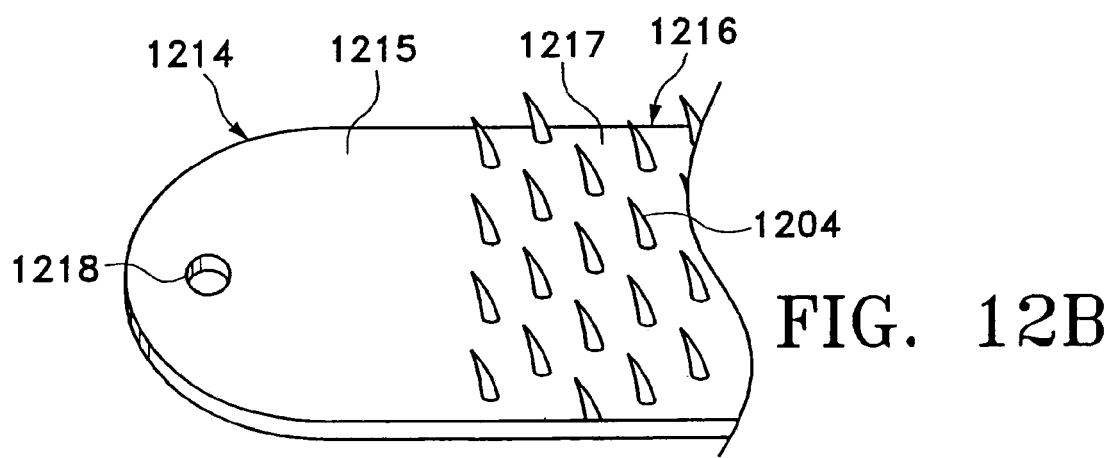
FIG. 12B is a plan, perspective view of the MTDS device used in a brow-lift.

The device may also be used in soft-tissue remodeling, such as a brow-lift, shown in FIG. 12A. After dissection of the scalp (1200), the anterior scalp flap (1202) may be raised over the attachment points (1204) to lift the brow (1206). The ends of both the anterior flap (1202) and posterior flap (1208) may then be trimmed and fixed onto the attachment points (1204) to close the wound. The device may be secured to the skull (1210) by a screw (1212). The inventive device in this example may have a first end (1214) and a second end (1216), the first end having a first area (1215) and the second end having a second area (1217). The first area (1215) and second area (1217) may have extending attachment points (1204) or one or more openings (1218) to accommodate a screw(s) (1212). The second area attachment points are canted toward the first end of the device as shown in FIG. 12B.

FIGS. 13A-13C show an alternative variation of the device which may be used in a brow-lift or similar surgical procedure. This device may generally be inserted under a patient's scalp while securely interlocking a small portion of the scalp to the device preferably via a plurality of attachment points. It may also be designed generally to lay against the cranium in a low profile while secured to the cranium to provide a brow lift. This variation comprises supportive backing (1300), which is shown substantially as an equilateral triangle, or in a delta shape. Backing (1300) may be any of a wide variety of triangular shapes, e.g., isosceles, etc. which functions to distribute planar loads equally radiating from a small area, e.g., post (1304). Various alternative shapes are discussed below in greater detail. Post (1304) is functionally for the maintenance of the device in place; other sections of the surgical procedure used to support the device in a specific part in the body. Post (1304) is placed on the side of the body opposite to the tines.

Figure 13D:
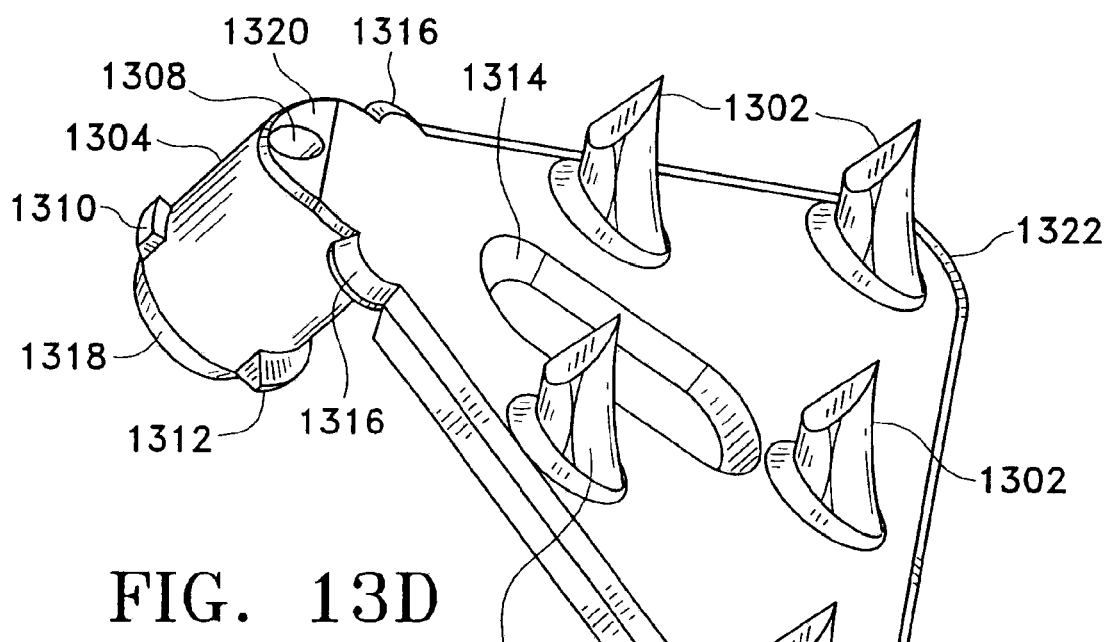
FIG. 13D is a perspective view of the device of FIG. 13A.

FIG. 13A shows a front side view of supportive backing (1300). This variation may incorporate sharp corners at the triangle vertices, but preferably has radiused or rounded corners (1322) to aid in reducing abrasion and cutting in adjacent tissue. Anchoring post (1304) may be located at one of the vertices of backing (1300). This anchoring post (1300) is shown in this variation as being substantially perpendicular to a plane of backing (1300), but may be other shapes as discussed below. Moreover, this device may be made of any of the materials discussed herein, and is preferably comprised of a biodegradable or bioabsorbable material but is obviously not limited by material type. For instance, the device may be comprised of certain biological materials as well, e.g., collagen, hydroxyapatite from both natural and synthetic sources, bone graft, or any combination or polymerized version of these materials. FIG. 13D shows more clearly a perspective view of a preferred variation of the device shown in FIGS. 13A-13C.

In this variation, supportive backing (1300) may comprise a triangular form having a first end (1324) and a second end (1326). This variation may typically be comprised of a front side, as shown in FIG. 13A, and a back side, as shown in FIG. 13B. On the front side, preferably near a vertex of the triangular shape, is an anchoring region. This region may comprise anchoring post (1304) as seen in FIGS. 13A-13C, and this anchoring post (1304) may be a variety of shapes, e.g., a hook or an angled post, etc., but is preferably a perpendicular post having a proximal and a distal end. Moreover, post (1304) is preferably integral with backing (1300) so as to be formed from a single piece. This allows the device to be formed entirely into a single integral device by various manufacturing methods, e.g., injection or die molding. Post (1304) may also be a separate structure fixedly attached to backing (1300) by any variety of fastening methods, e.g., mechanical fasteners or adhesives. The distal end of post (1304) maybe chamfered (1318), as shown in FIGS. 13A and 13C; this would provide a degree of tolerance to enable the surgeon to easily locate and insert post (1304) into a receiving hole without sacrificing device integrity.

Post (1304) may preferably further comprise a locking device proximal of chamfer (1318). This locking device may utilize a variety of locking mechanisms but is shown in this variation as front tab (1310) and partial collar (or rear tab) (1312). The locking mechanism is preferably integral with post (1304) and may have a diameter which is greater than a diameter of post (1304). In any case, partial collar (1312) is preferably elastically deformable, but may also be plastically deformable. Such deformability allows front tab (1310) and partial collar (1312) to compress upon insertion into a patient's skull and subsequently be able to spring back upon full insertion to provide a friction-fitted locking or securing feature. The locking device may alternatively be a locking key mechanism or any conventional locking mechanism. However, the locking mechanism may be omitted entirely because the device bases much of its stability, once inserted into a patient's cranium, upon the downward forces applied by the overlying tissue. Thus, much of the forces acting on the device apply bending loads on post (1304) rather than axially-oriented tensile loads.

Figure 13E:
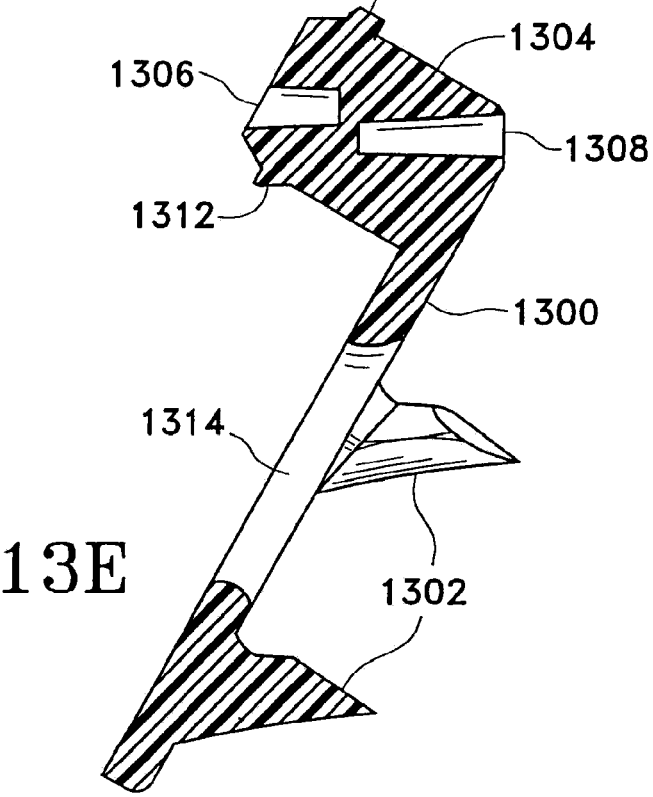
FIG. 13E is a view of cross-section 13E-13E from FIG. 13B showing the cavities in the post.

As seen in FIG. 13A, post (1304) may incorporate a distal channel or cavity (1306) which may extend partially into the post from the distal end or entirely through the post. This distal cavity (1306) may have a diameter which is smaller than the diameter of post (1304) and may be aligned along an axis defined by post (1304) or may extend at an angle within post (1304). The cross-section 13E-13E of FIG. 13B is shown in FIG. 13E and shows more clearly the orientation of distal cavity (1306) within post (1304) for this variation. Distal cavity (1306) may aid in reducing the amount of material used in the manufacture of the device, and is particularly useful in imparting a desirable degree of flexibility to post (1304) which may facilitate the insertion of post (1304) into the cranium.

Post (1304) may further define another hole, proximal cavity (1308), which may be used for tooling purposes as well as further adding to the flexibility of post (1304). Proximal cavity may extend from chamfered proximal end (1320), which may also aid in tooling and helping to prevent tissue abrasion. Proximal cavity (1308) may be non-concentrically located relevant to distal cavity (1306) and as shown in FIG. 13E, may extend partially into post (1304) or may be a through-hole extending entirely through to the distal end of post (1304). Although proximal cavity (1308) may not necessarily be required, it may be utilized in a variety of ways. For example, proximal cavity (1308) may be used for aligning the device for tooling during manufacture, or it may also be used as a location to allow a user or surgeon to manipulate the device using tools for placement of the device within a patient. This proximal cavity (1308) may have a diameter, e.g., about 1 mm, which is smaller than a diameter of post (1304).

In addition to proximal cavity (1308), the device may also comprise protrusions, tabs, or "ears" (1316), as seen in FIGS. 13A-13D. These protrusions (1316) are preferably integral with backing (1300) and may generally be located anywhere on backing (1300), but is preferably located near first end (1324), and more preferably near post (1304). FIG. 13B shows protrusions (1316) located on either side of post (1304) and may provide a surface for manipulating the device by the doctor or surgeon either during placement into the patient or during removal.

FIGS. 13A and 13C show the front and side views, respectively, of attachment points (1302). As discussed above, attachments points (1302), also called "tines" or "prongs" are preferably integrally affixed to backing (1300) but may also be separately attachable. They are preferably located on the back side of backing (1300), i.e., the side opposite of post (1304), and are preferably angled towards first end (1324). Moreover, individual attachment points (1302) may be of varying sizes and angles depending upon the desired securing effect. Attachment points (1302) are discussed in greater detail above. In this variation, individual attachment points (1302) may vary in density, but are optimally spaced relative to one another. Factors for optimizing attachment point relative placement may comprise the ease of securing tissue to attachment points (1302) and the distribution of loads generated by the attached tissue over each of attachment points (1302). For instance, if attachment points (1302) were located too closely to one another, piercing the tissue would be difficult because of the distribution of stresses on the tissue to be pierced by attachment points (1302).

Another example may include having an increasing number of attachment points (1302) placed on backing (1300) the farther they are located from post (1304) or front end (1324), where the greatest number of attachment points are located in the direction of tensile loads on the device. The spacing between individual points (1302) may be functional in that the number, density, and placement of points (1302) are such that the points (1302) optimally distribute the loads, e.g., shearing forces and bending moments, generated by the attached scalp in a brow-lift procedure. Moreover, attachment points (1302) are preferably configured to penetrate partially through the soft tissue. For instance, the sharpness of attachment points (1302) are such that they allow easy penetration through the periosteum.

FIGS. 13B and 13D show supportive backing (1300) which may also comprise through-hole (1314) that is defined within backing (1300). Through-hole (1314) may generally be any shaped hole but is shown in this variation as being slotted. Through-hole (1314) serves several functions which may include reducing the amount of material used in manufacturing the device, it may also add desirably to the flexibility of backing (1300). Additionally, through-hole (1314) may be configured as an alignment aid for tooling purposes. In addition to aligning, through-hole (1314) may also serve as a surface for a tool to grasp during device placement or removal. Flexibility is preferable because it enables backing (1300) to bend and conform more closely to the shape of the patient's cranium against which the device is placed. The degree of flexibility of backing (1300) may be tuned to a predetermined degree depending upon several factors, e.g., the configuration and size of through-hole (1314). Although shown as a slot, backing (1300) may define virtually any through-hole shape which serves the functions discussed above, i.e., increasing backing (1300) flexibility and aiding in tool alignment.

Method of Installing and Securing

FIGS. 14A-14D illustrate a preferable method of installing the device of FIG. 13A. The top of a patient's head is shown having a hairline (1402). As seen in FIG. 14A, the doctor or surgeon may initially make an incision (1404) in scalp (1414) preferably along a sagittal plane defined by cranium (1400). The incision (1404) may typically be done in the patient's hairline, if possible, to minimize any visible scarring which may result. The length of incision (1404) is typically determined by the length or amount of scalp the patient may desire or the surgeon may determine necessary to be lifted for a successful brow-lift procedure. This incision length may generally range from about 1 to 2 cm but may be more or less depending on the desired results.

Once incision (1404) is made, a hole (1410) may be drilled within cranium (1400) at the incision second end (1408). Hole (1410) drilled into cranium (1400) may typically be about 4.0 mm in diameter and may be made by a conventional surgical drill (not shown). As shown in FIG. 14B, once the incision and hole are made, an MTDS device (1412) may be inserted between cranium (1400) and scalp (1414) at the incision first end (1406) such that post (1304) faces towards cranium (1400) and attachment points (1302) face the underside of scalp (1414), i.e., subperiosteal. FIG. 14C shows an outline of device (1412) placed at incision first end (1406) and beneath scalp (1414). Once device (1412) has been inserted, the portion of the scalp tissue to be raised (1416) is set on device (1412) via attachment points (1302). FIG. 15 shows a cross-sectional view of FIG. 14C where the tissue to be raised (1416) has been set on attachment points (1302). Once tissue (1416) is set, a force (1500) maybe applied to device (1412) preferably via post (1304). Force (1500) then draws the device (1412) and tissue (1416) towards hole (1410) which is configured to receive post (1304). As shown in FIG. 14D, once post (1304) is secured within hole (1410), force (1500) may be removed, thereby leaving the brow desirably lifted.

Once device (1412) has been installed, attachment points (1302) and post (1304) undergo shear and bending loads from the lifted tissue (1416) pulling on the device (1412). However, these loads may decrease rapidly and approach zero as scalp (1414) heals. This decrease in loading may take up to about six weeks, but device (1412) may stay in place beneath scalp (1414) for up to several years, with sufficient strength for about six weeks, to prevent scalp (1414) from moving excessively during the healing process and thereafter being absorbed by the body, thereby removing the necessity for a second procedure to remove device (1412).

Variations on Attachment Points

Figure 16D:
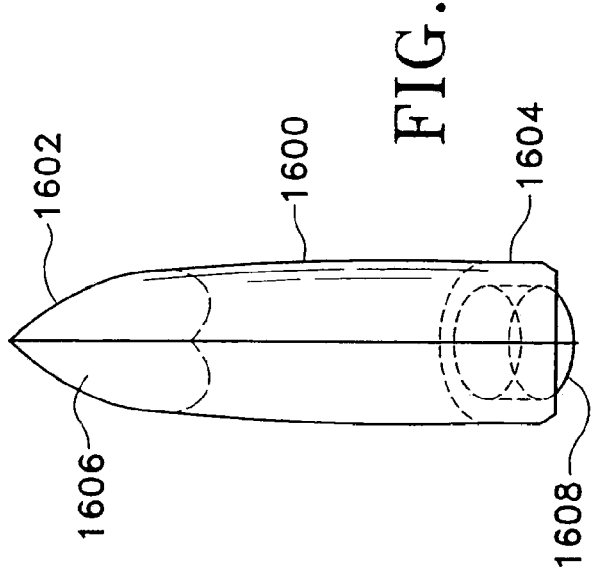
FIGS. 16A-16D are various views of an exemplary attachment point from FIG. 13A.
Figure 16C:
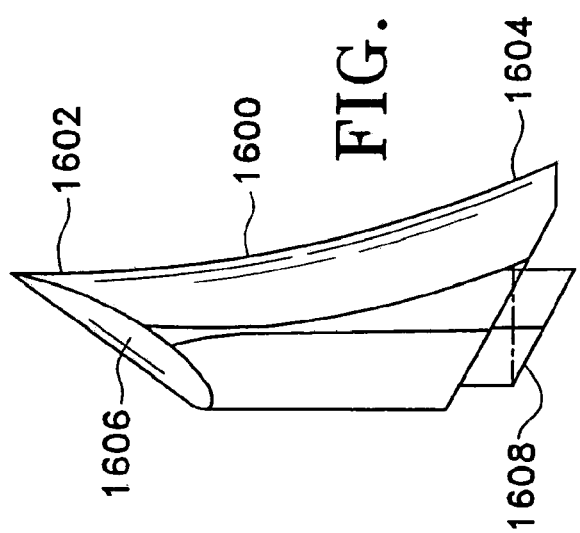
Figure 16A:
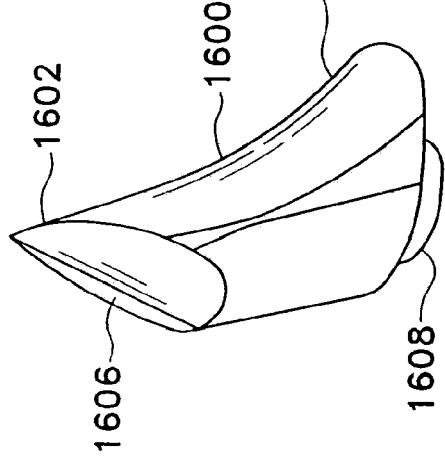
Figure 16B:
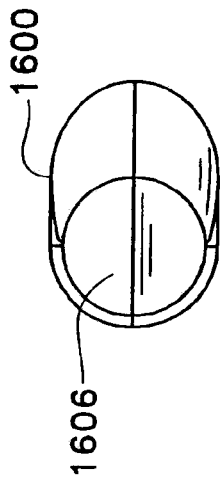

FIGS. 16A-16D show a preferred variation for an attachment point on a brow lift device. FIG. 16A shows a top view of a single attachment point (1600) having a swept face (1606). FIG. 16B is a side view of attachment point (1600) comprising distal pointed end (1602) and proximal base end (1604). Although any variations of attachment points discussed above may be used on the brow lift device, this variation is preferable because it is able to readily pierce tissue through the periosteum and simultaneously secure the tissue solidly by resisting any bending moments. In particular, swept face (1606) may be specifically faceted so that face (1606) is preferably oriented to be essentially perpendicular to the plane of the tissue or scalp being penetrated, even though the tine axis defined by attachment point (1600) may not be perpendicular to the plane of the tissue or scalp.

Attachment points of this variation may optionally be manufactured individually and separately from the supportive backing and then individually attached via backing attachment (1608) to the backing by a variety of fastening methods, e.g., friction fitting, adhesives, etc. Optional backing attachment (1608) is seen in FIG. 16B, and more clearly in the back view of FIG. 16C. FIG. 16D shows the variation more clearly in a perspective view. Attachment point (1600), as mentioned, may be manufactured separately and attached, but it is preferably made integral with the MTDS device. Integrating the attachment point(s) (1600) with the backing not only provides uniformity in material type but also eliminates contact interfaces, which in turn may provide superior material strength and resistance to bending.

As discussed above and as shown in FIGS. 13A-C, attachment points (1600) are preferably manufactured or attached so that they are all substantially canted in parallel towards the post. However, the attachment points are faceted such that the tips of attachment points (1600) are effectively perpendicular to the tissue to be penetrated. Attachment points (1600) may also be manufactured or assembled so that they point in different predetermined directions, depending on the desired application. Furthermore, attachment points (1600) may optionally be made of varying sizes, as discussed in further detail above.

Variations on Posts

Figure 17A:
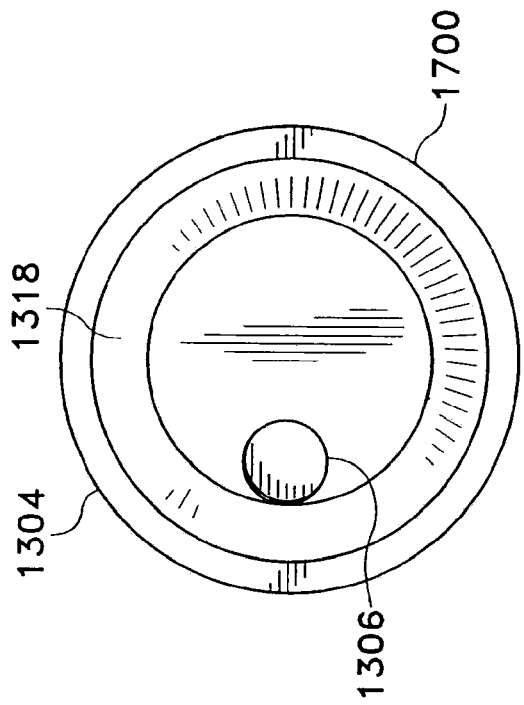
FIG. 17A is a view from perspective 17A-17A from FIG. 13C of the post having a partial collar.

FIG. 17A shows perspective 17A-17A from FIG. 13C of the distal end of post (1304). As shown, partial collar (1312) and front tab (1310) preferably comprises integral extensions or protrusions which act as a locking device. Both partial collar (1312) and front tab (1310) may be plastically deformable but is preferably elastically deformable. The protrusions provide opposing forces upon insertion into the skull to produce a friction fit which secures the device in the patient. Partial collar (1312) may essentially circumscribe any predetermined percentage of the circumference of post (1304), provided that a sufficient fit is produced.

Aside from partial collar (1312), post (1304) may alternatively use locking mechanisms comprising barbs and subcortical wings. Moreover, post (1304) may also be threaded so as to be rotated, or screwed, into a threaded mating hole located within the patient's cranium.

Figure 17B:
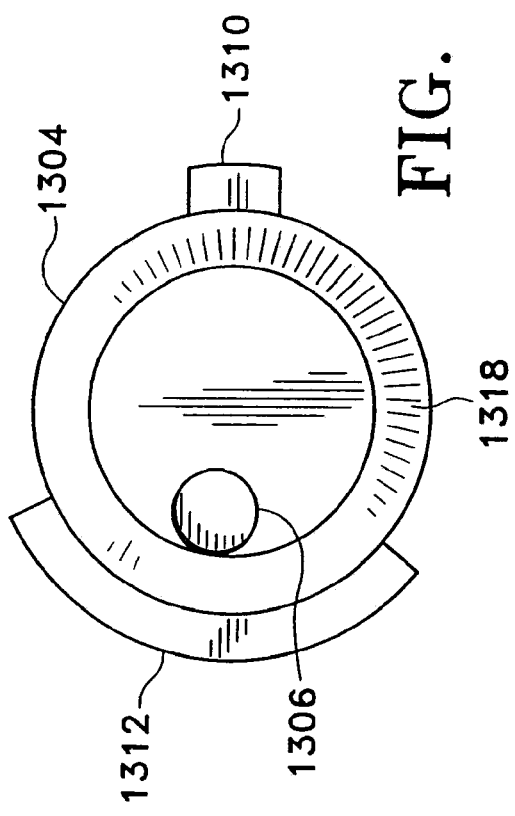
FIG. 17B is a variation of FIG. 17A of the post having a full collar.
Figure 17C:
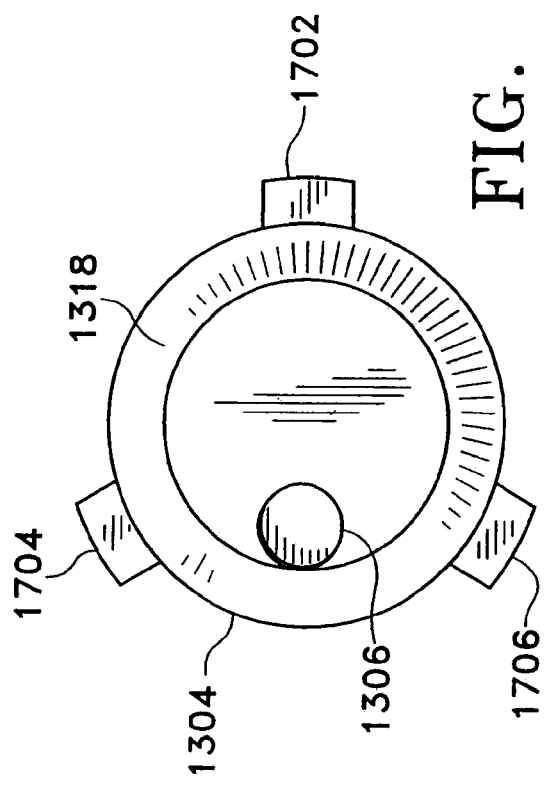
FIG. 17C is a variation of FIG. 17A of the post having several tabs.

FIG. 17B shows an alternative locking configuration from FIG. 17A. Here, partial collar (1312) is replaced by full collar (1700), which is preferably integral with post (1304) and may also be plastically or elastically deformable. A further variation for a locking configuration is shown in FIG. 17C, in which first, second, and third tabs (1702), (1704), (1706), respectively, replaces partial collar (1312). Again, tabs (1702), (1704), (1706) are preferably integral and elastically deformable, although they may also be plastically deformable. Essentially any locking configuration may be utilized by a doctor or surgeon depending upon the desired fit of post (1304).

Figure 19A:
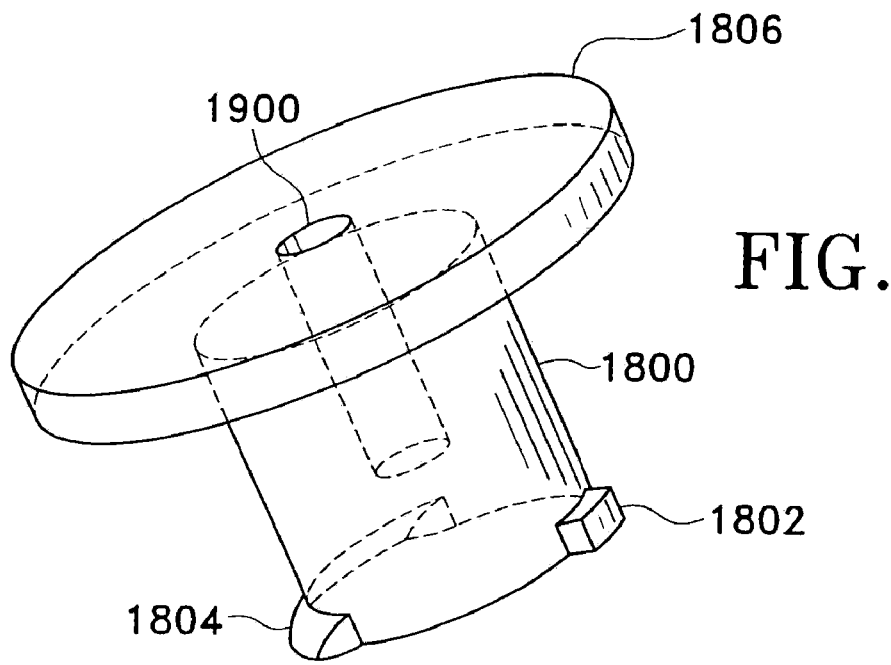
FIG. 19A is a perspective view of the post from FIG. 18B showing the proximal cavity within the post.
Figure 19B:
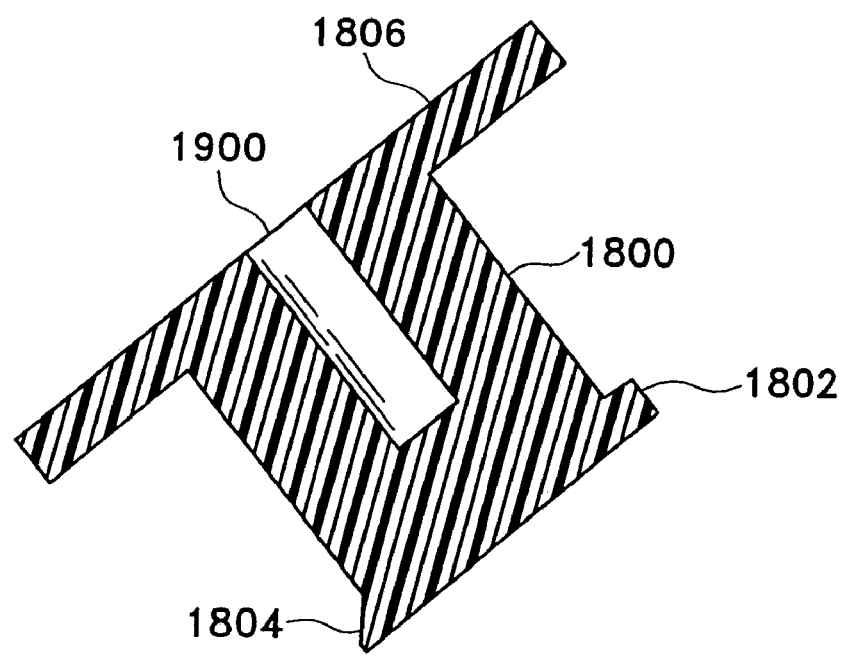
FIG. 19B is a view of cross-section 19B-19B from FIG. 18B showing the proximal cavity.

Aside from varying locking mechanisms, the flexibility of the post may be varied as well. As mentioned above, cavities may be disposed within the post to increase the post flexibility. FIG. 18A shows a back view of a variation of the cavity from FIG. 13B. As seen in FIGS. 18B and 18C, post (1800) is similar in most respects to the post shown in FIG. 13B. Post (1800) is illustrated extending from backing (1806), which is partially shown merely for clarity, with front tab (1802) and partial collar (1804). However, FIG. 18A shows a single axial cavity (1900) disposed within and extending from a proximal end of post (1800). FIG. 19A shows a perspective view of post (1800) from FIGS. 18A-18C where axial cavity (1900) is axially disposed within post (1800) and extends partially through. Cavity (1900) may extend through post (1800) perpendicularly to backing (1806) and concentrically along an axis defined by post (1800), but it may also extend off-axis and at an angle, as shown in FIG. 13E. Furthermore, cavity (1900) may also extend entirely through post (1800) as a through-hole. FIG. 19B shows the cross-section 19B-19B taken from FIG. 18B clearly showing cavity (1900) extending partially into post (1800).

Figure 20:
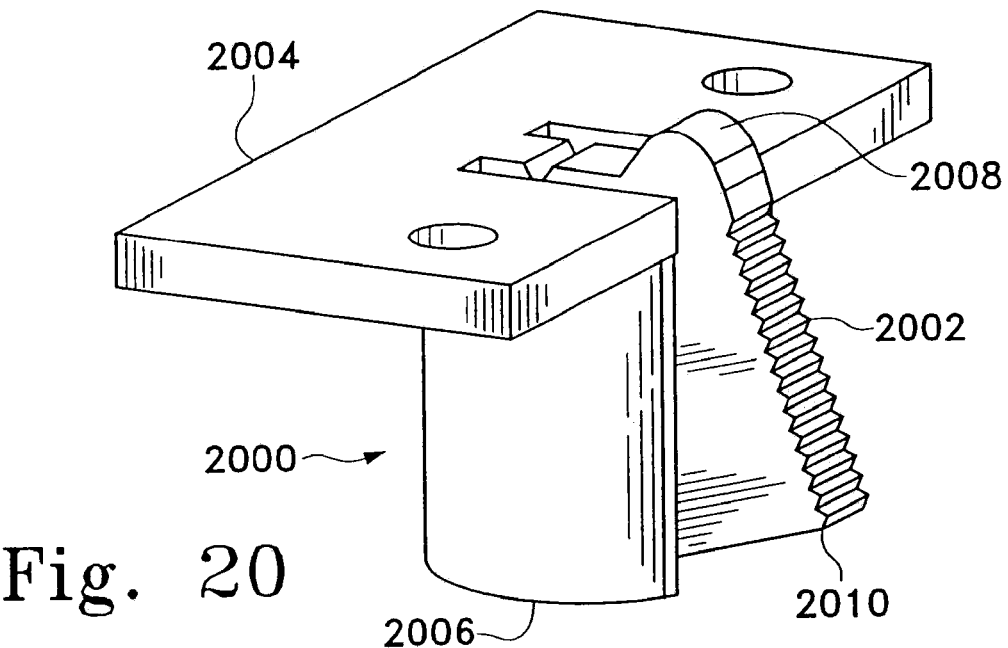
FIG. 20 is a perspective view of a post variation having a beveled latching mechanism.

Another variation on the post is shown in FIG. 20. Latched post (2000) is shown having beveled latch (2002) pivotally disposed between post members (2006). Latched post (2000) is shown extending from backing (2004) of which only a portion is shown for clarity. Beveled latch (2002) is preferably integrally attached at a proximal end so that latch distal end (2010) is free to move. Beveled latch (2002) is also preferably beveled to provide a gripping surface once the device is secured in the patient. Because latch distal end (2010) may be free to move, latch (2002) may be configured so that latch distal end (2010) may be biased to extend angularly away from post members (2006). As post (2000) is inserted into a patient's cranium, latch distal end (2010) may be urged towards post members (2006) to facilitate insertion by depressing lever (2008), located at the proximal end of latch (2008). Once latched post (2000) has been positioned in the patient, lever (2008) may then be released, thus allowing latch distal end (2010) to protrude angularly against the interior of the hole in the patient's cranium thereby providing a locking action.

Figure 21:
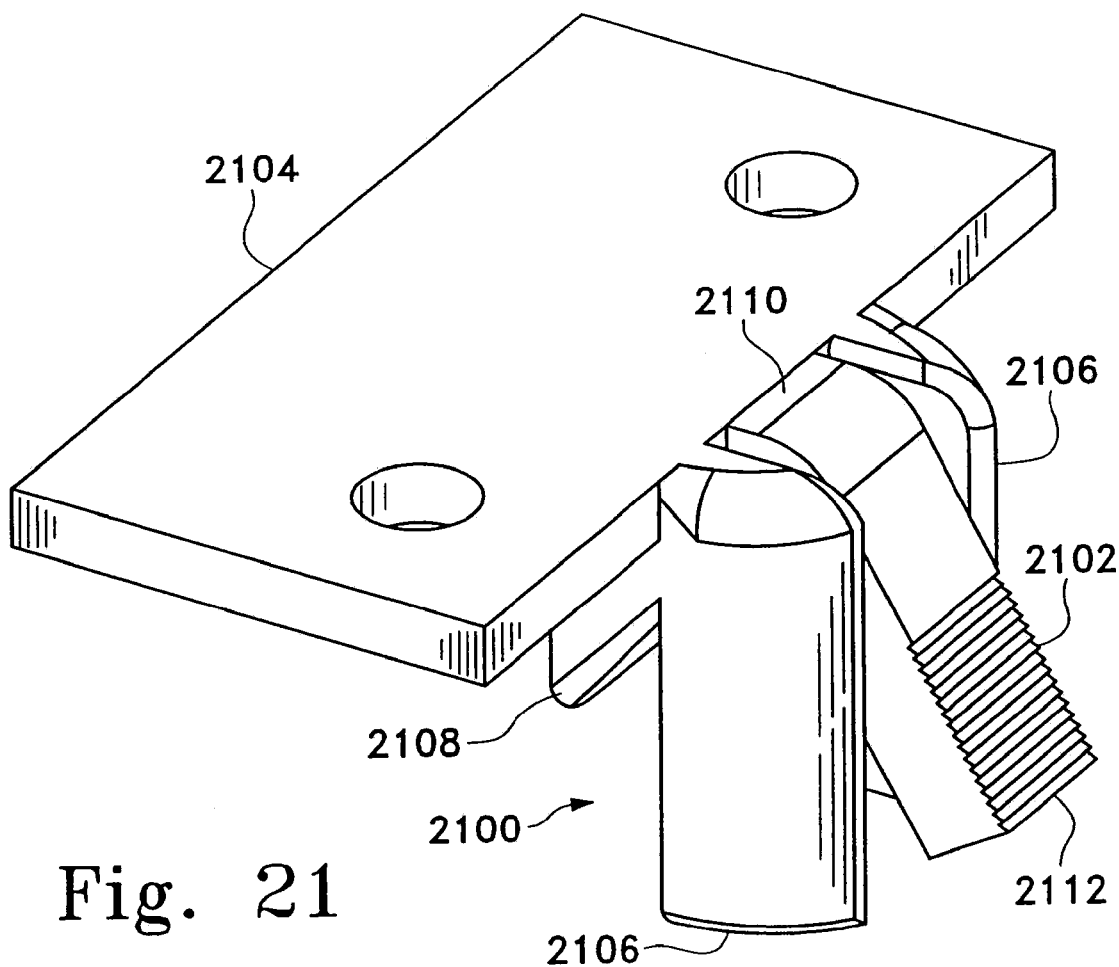
FIG. 21 is a perspective view of another post variation having an integral beveled latching mechanism.

A further variation of the post is shown in FIG. 21. Here, angled latch post (2100) is preferably an angled latch (2102) having a beveled surface and being integral with backing (2104) of which only a portion is shown for clarity. Angled latch (2102) may be integral with backing (2104) at the latch proximal end (2110) and disposed in-between post members (2106). Angled latch (2102) may further be biased so that the latch distal end (2112) is angled away from backing (2104) and protrudes from in-between post members (2106). Accordingly, as angled latch post (2100) is inserted into the patient's cranium, latch distal end (2112) may similarly be urged towards post members (2106) to likewise facilitate insertion. This movement or urging may be accomplished by depressing latch extension (2108), which may be integrally attached to both backing (2104) and angled latch (2102). Because latch extension (2108) may be attached in apposition to angled latch (2102), depressing it would thereby move latch distal end (2112) accordingly.

Figure 22A:
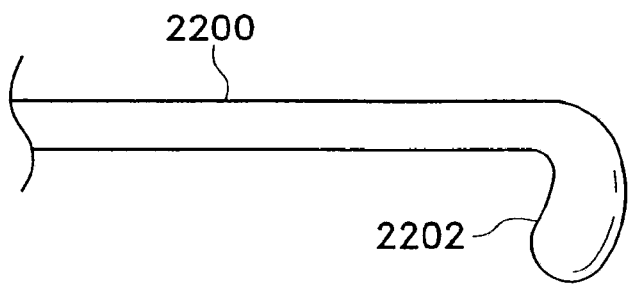
FIG. 22A is a side view of a post variation having a rounded hook.
Figure 22B:
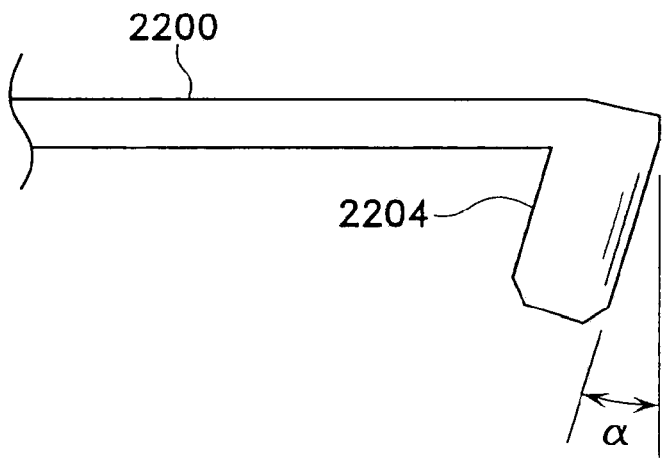
FIG. 22B is a side view of a post variation having an angled post.
Figure 22C:
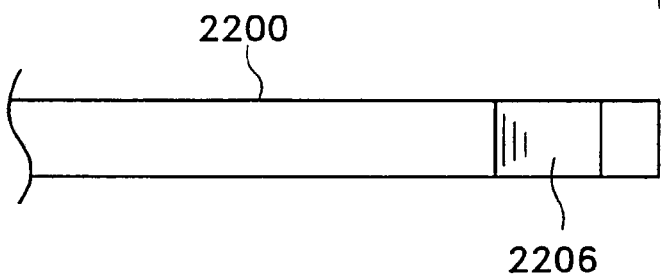
FIG. 22C is a side view of the supportive backing defining a hole to receive a separate fastening device.

FIGS. 22A-22B show alternative variations of the post which may include any of the features discussed herein. FIG. 22A shows rounded post (2202) having a radiused distal end. FIG. 22B shows angled post (2204) which defines a predetermined angle, α, between a plane of backing (2200) and a longitudinal axis defined by angled post (2204). FIG. 22C shows another variation where a post is not used at all. Rather, a hole may be provided which has a diameter sufficient to receive a separate fastener. In this variation, the fastener may be used to secure backing (2200) to the patient's cranium through hole (2206). Fasteners may comprise any conventional fasteners, e.g., pins, nails, screws, and so forth. Alternatively, rather than securing the device via a fastener through a hole, the hole (2206) may be omitted entirely and the backing (2200) may be secured to the cranial surface via an adhesive, e.g., cyanoacrylate. Such an adhesive is preferably biocompatible and provides sufficient bonding strength to support the tissue or scalp when lifted.

Figures 22D, 22E:
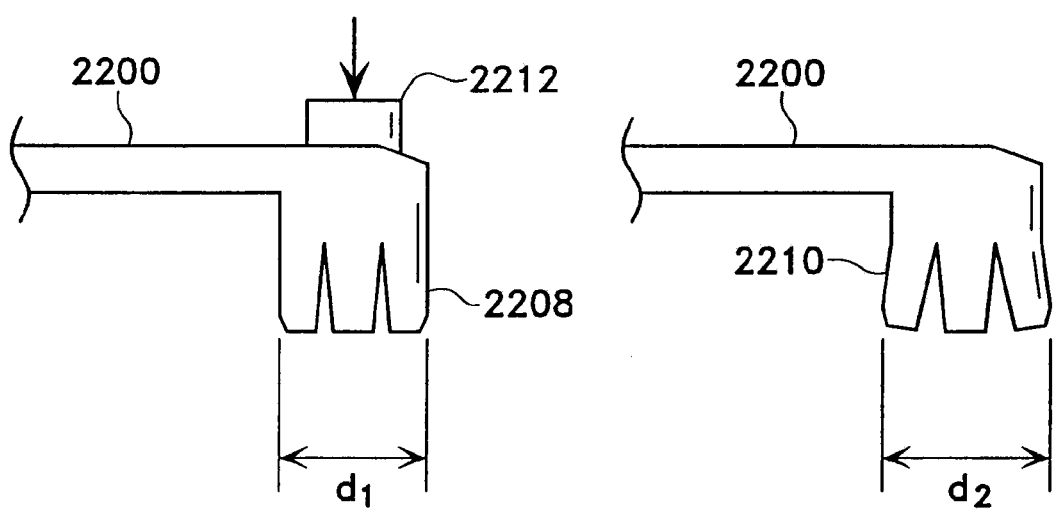
FIGS. 22D-22E are side views of a radially expandable post variation.

FIGS. 22D-22E show an alternative variation where the post comprises radially expandable extensions. Expandable post (2208) is preferably integral with backing (2200) to provide a uniform device. FIG. 22D shows expandable post (2208) having a first diameter, $d_1$. This device may be inserted into the patient's cranium and positioned in a desired location and configuration. Once positioned, the diameter may be expanded by inserting expander device (2212), or using a tool configured to expand radially, which pushes against the inner surfaces of expandable post (2208). The resulting expanded configuration is shown in FIG. 22E where expanded post (2210) has a second diameter, $d_2$, which is larger than first diameter $d_1$ and thus aids in securing the device in place.

Variations on Drilled Holes

Figure 23A:
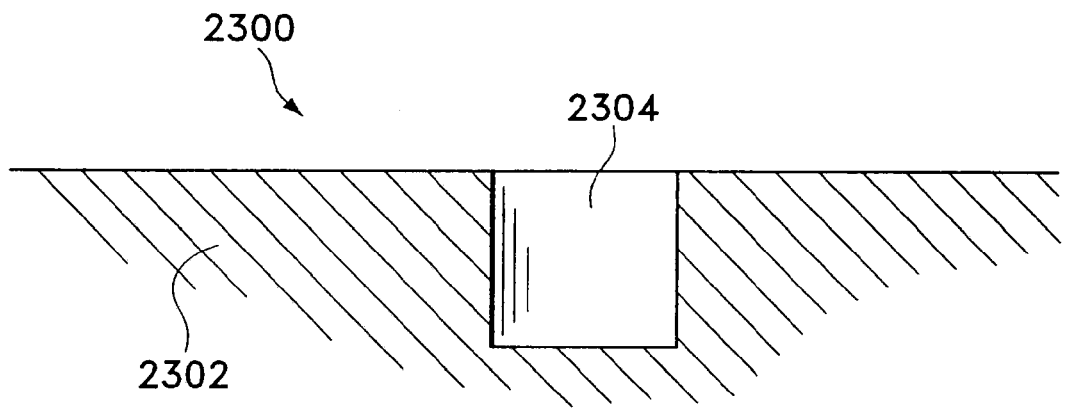
FIG. 23A is a cross-sectional view of a typical hole in a patient's cranium for receiving a post.
Figure 23B:
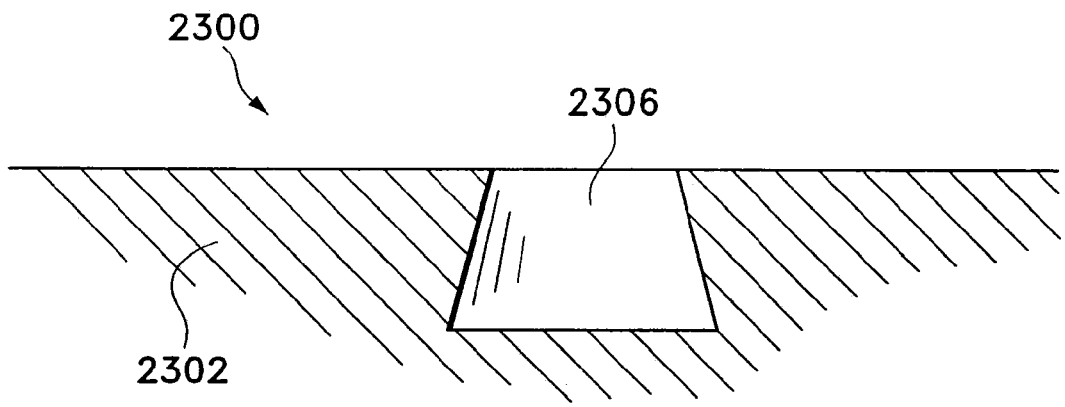
FIG. 23B is a cross-sectional view of an angled hole variation for receiving a post.
Figure 23C:
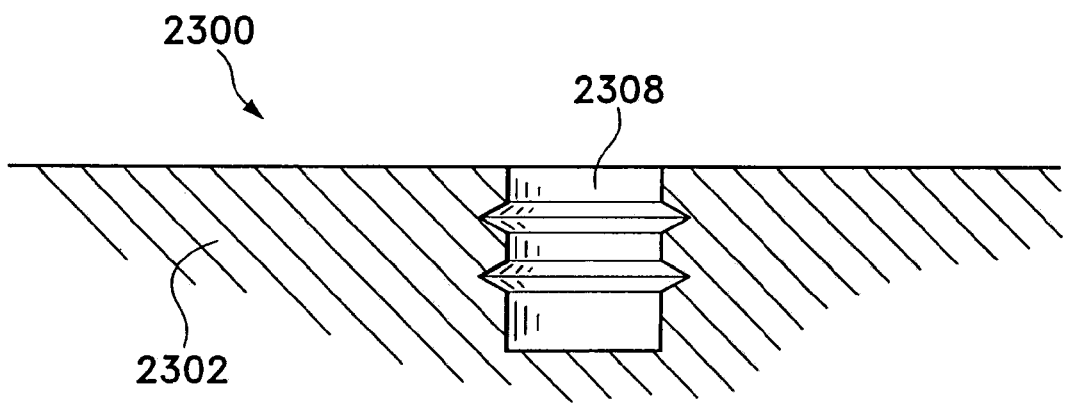
FIG. 23C is a cross-sectional view of a possible keyed hole variation for receiving a post.

In securing a brow lift device within a patient, a hole may be drilled into the cranium to receive the securing post of the device. As mentioned above, the hole may be drilled by any number of conventional drills or specialized surgical drills. FIG. 23A shows a cross-sectional view of a typical drilled hole (2304) in cranium (2300) which extends down into the cranial bone (2302). FIG. 23B shows another variation having angled hole (2306) which may be used to receive any of the post variations discussed herein. A further variation is shown in FIG. 23C where the hole may comprise keyed hole (2308). This variation shows keyed hole (2308) having two concentric grooves within the hole; however, any number of grooves or variations thereof may be incorporated depending upon the desired hole profile and the tightness of the fit of the post within the hole.

Variations on Supportive Backings

Figure 24A:
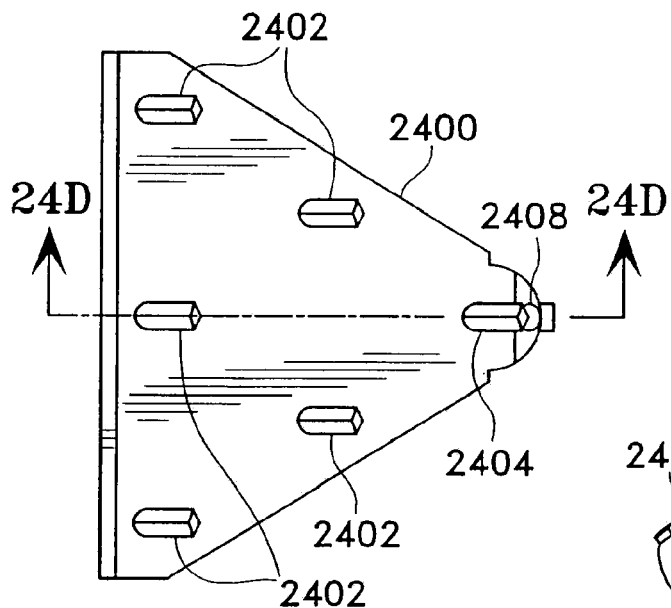
FIGS. 24A-24C are top, side, and perspective views of an alternative variation of the MTDS device.
Figure 24C:
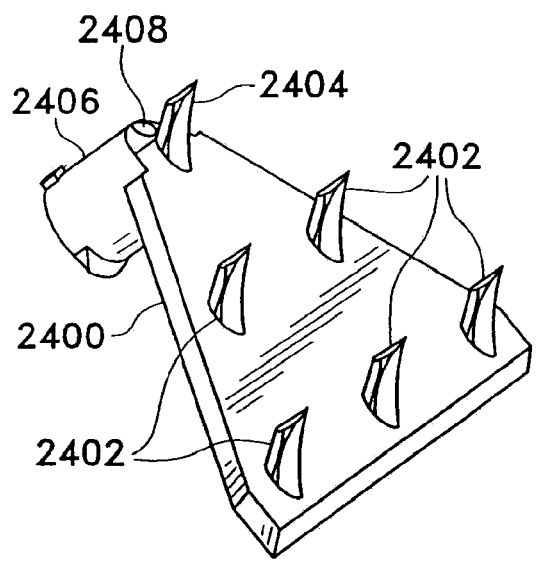
Figure 24B:
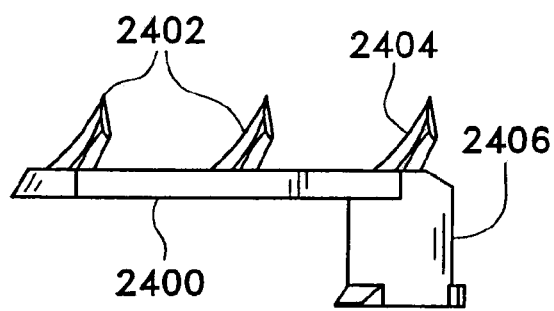
Figure 24D:
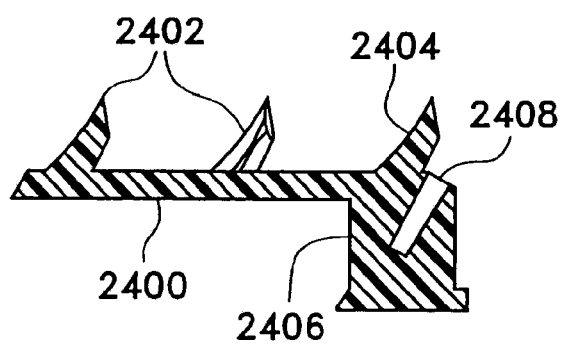
FIG. 24D is a view of cross-section 24D-24D from FIG. 24A.

FIGS. 24A-24D show a variation on the brow lift device backing. FIGS. 24A-24B show a top and side view of a device which is similar in many aspects to the device as shown in FIGS. 13A-13C. The device comprises supportive backing (2400), post (2406), proximal cavity (2408), and attachment points (2402). However, this variation also comprises an additional leading attachment point (2404). This leading attachment point (2404) may be incorporated as a redundancy to ensure tissue adhesion should the other attachment points (2402) slip or tear from the scalp tissue. FIG. 24C shows a perspective view of the device with leading attachment point (2404). And FIG. 24D shows a view of cross-section 24D-24D from FIG. 24A. Proximal cavity (2408) is clearly seen to extend partially into post (2406); but post (2406) may incorporate other cavities and configurations as discussed above.

FIG. 25A shows a top view of supportive backing (2500). This variation is also similar in many aspects to the device as shown in FIGS. 13A-13C. The device may comprise post (2504), proximal cavity (2508), and through-hole (2510), which may be slotted or may comprise any other shape. Also, as seen in FIGS. 25B and 25C, the device may also comprise distal cavity (2506); however, this variation may have separatable attachment points which may be held in attachment point locations (2502). This variation may allow a doctor or surgeon to attach variously shaped attachment points in a variety of orientations relative to one another depending upon the desired result. Moreover, this variation may allow one to selectively attach attachment points at desired attachment point locations (2502). Any number of attachments points may be utilized; however, it is preferable that at least three attachment points or tines spaced relatively apart be used to optimize the holding capacity of the device to the tissue.

Figure 26C:
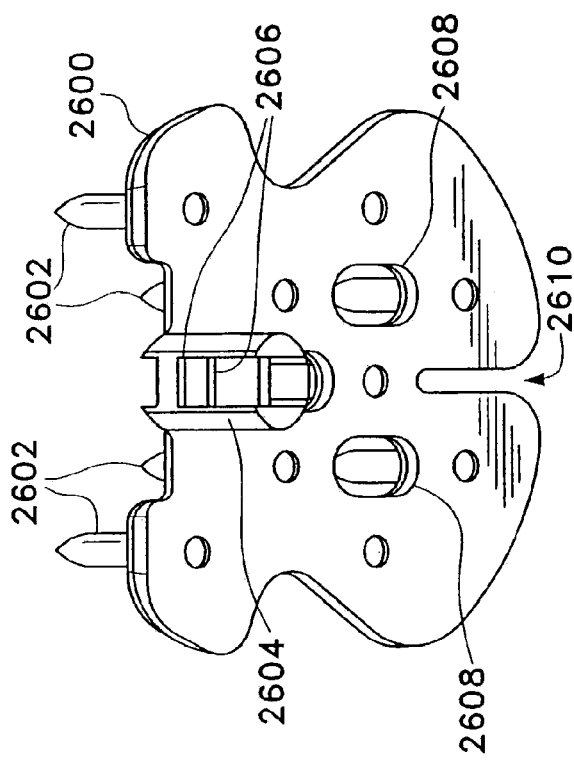
FIGS. 26A-26C are top, side, and back views of a variation of the MTDS device having dual tabs on the post.
Figure 26A:
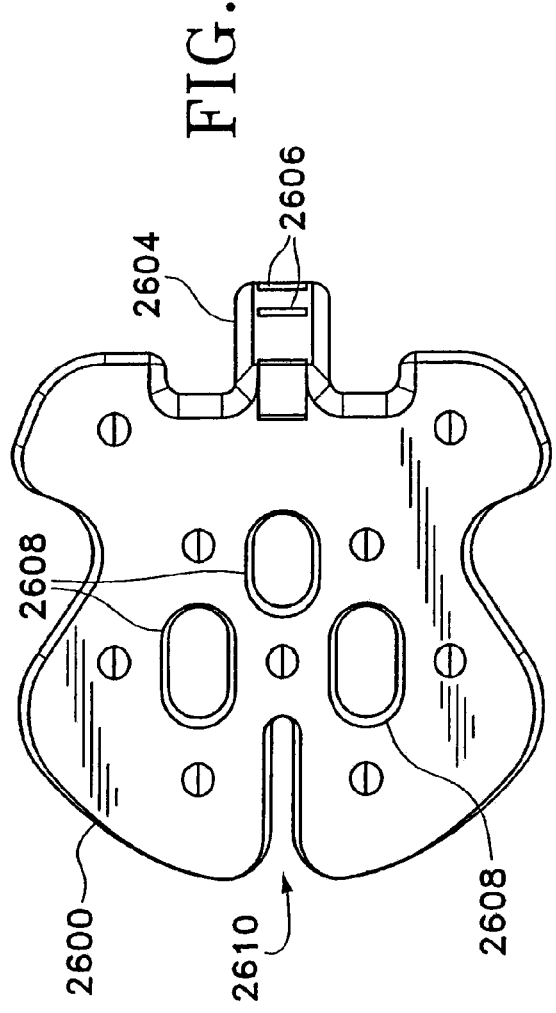
Figure 26B:
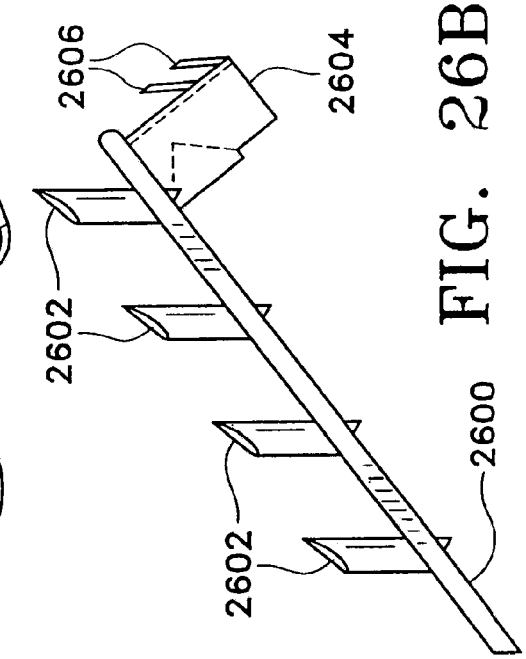

FIG. 26A shows a top view of an alternative variation for supportive backing (2600) which is configured to be flexible and hold multiple attachment points (2602). This particular variation may be configured to reduce the amount of material used and simultaneously increase the flexibility to allow backing (2600) to conform to the patient's cranium. Flexibility may be achieved via the use of through-holes (2608) and slot (2610) which are seen in FIGS. 26A and 26C. This variation also may incorporate post (2604) which may comprise anchoring tabs (2606), as seen in the side view of FIG. 26B, to aid in securing the device to the cranium.

FIG. 27A shows a top view of another alternative variation for supportive backing (2600) which is similar in most aspects to the device shown in FIG. 26A. As seen in FIGS. 27A-27C, particularly 27B, this variation incorporates latched post (2700). Post (2700) may utilize a latching mechanism similar to the latched posts illustrated in FIGS. 20-21. This particular post comprises latch (2702) which is shown as having a hooked distal end.

Figure 28A:
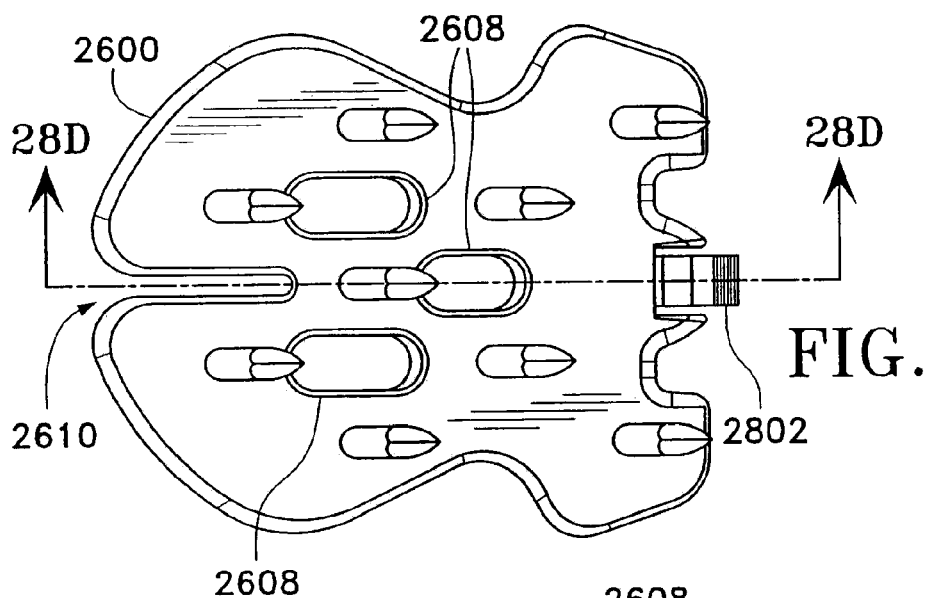
FIGS. 28A-28C are top, side, and perspective views of a variation of the MTDS device having another latching mechanism on the post.
Figure 28C:
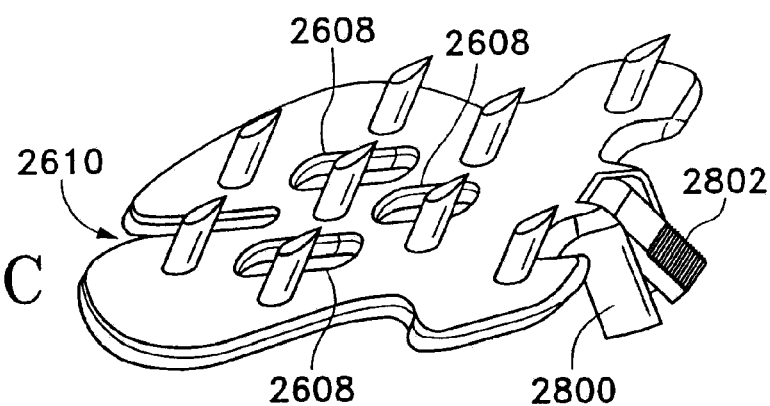
Figure 28B:
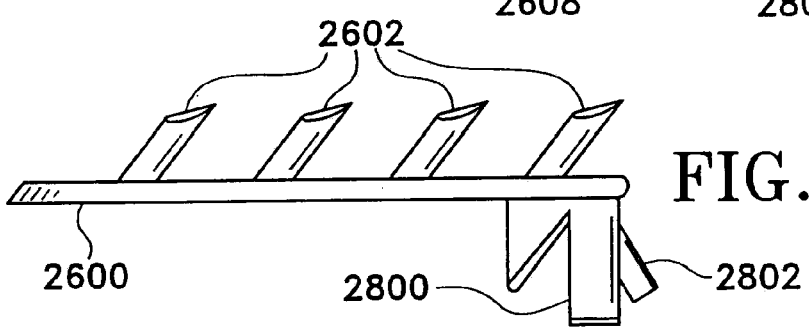
Figure 28D:
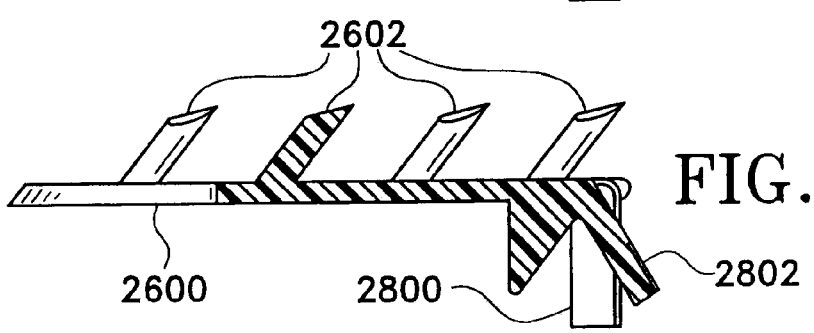
FIG. 28D is a view of cross-section 28D-28D from FIG. 28A.

FIGS. 28A-28C shows top, side, and perspective views of a further variation for supportive backing (2600). This variation illustrates latched post (2800) having beveled latch (2802) which may be similar to the latching device shown in FIG. 21. FIG. 28D shows a view of cross-section 28D-28D taken from FIG. 28A. The latched post (2800) and the configuration of latch (2800) may be seen where latch (2802) is preferably integral with backing (2600).

Figure 29B:
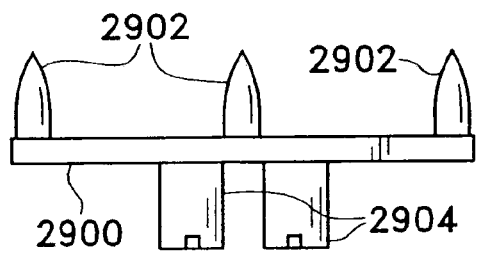
FIGS. 29A-29C are edge, back, and side views of a variation of the MTDS device having two adjacent posts.
Figure 29A:
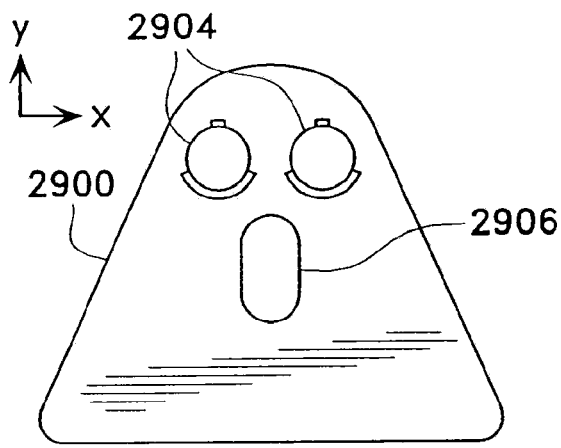
Figure 29C:
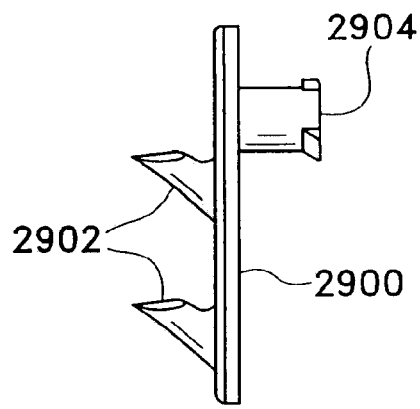

In addition to alternative backings, variations of MTDS devices having multiple posts may also be utilized. FIG. 29C shows a variation also having attachment points (2902) and through-hole (2906). As seen further in FIGS. 29B, this variation may comprise a configuration where two posts (2904) are attached to backing (2900). Posts (2904) are preferably attached integrally to backing (2900) and may be orientated, as seen in FIG. 29A, such that posts (2904) are aligned along an x-axis. The addition of a second post along the x-axis may aid in increasing the device resistance to rotation about the posts (2904) once it is inserted into the cranium. This added rotational stability may then allow the device to be inserted at various angles within the cranium relative to the tissue to be lifted depending upon the desired results.

Figure 30B:
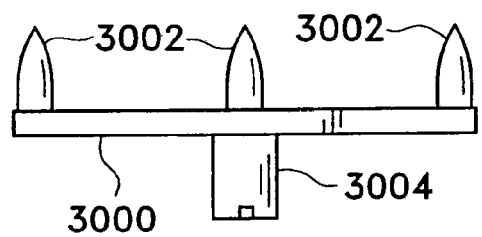
FIGS. 30A-30C are edge, back, and side views of another variation of the MTDS device having two aligned posts.
Figure 30A:
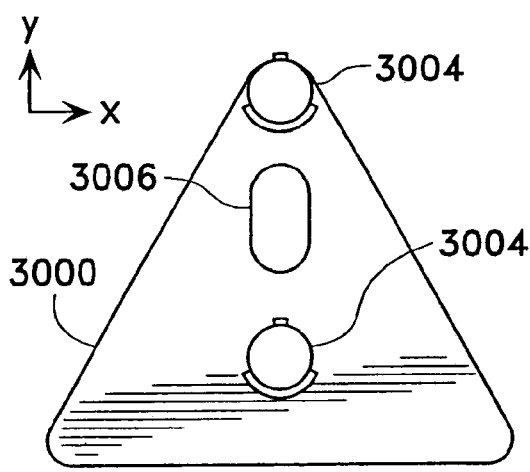
Figure 30C:
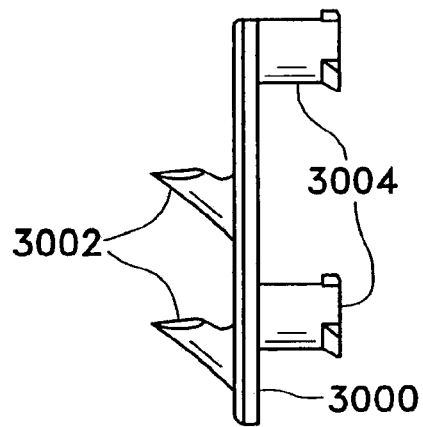

A further alternative backing having multiple posts is shown in FIG. 30A. Also seen in this variation are attachment points (3002) attached to backing (3000) and through-hole (3006) defined within backing (3000). However, this variation comprises two posts (3004), which are preferably integral with backing (3000), aligned along a y-axis. The additional post along the y-axis may aid greatly in also increasing the device resistance to rotation about posts (2904). This variation likewise may allow the device to be inserted at various angles within the cranium depending upon the desired results and the angle of desired lift. Furthermore, this particular variation may be desirable where cranial physiology would prevent two adjacent posts from being secured into the cranium.

Figure 31A:
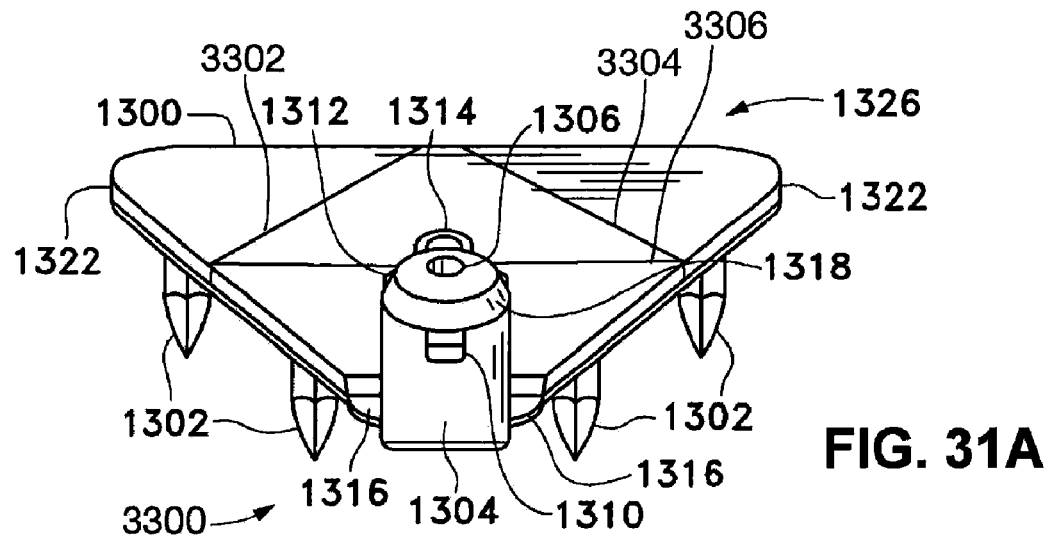
FIGS. 31A and 31B show various views of one variation of a device having serrations or score lines over the backing.
Figure 31B:
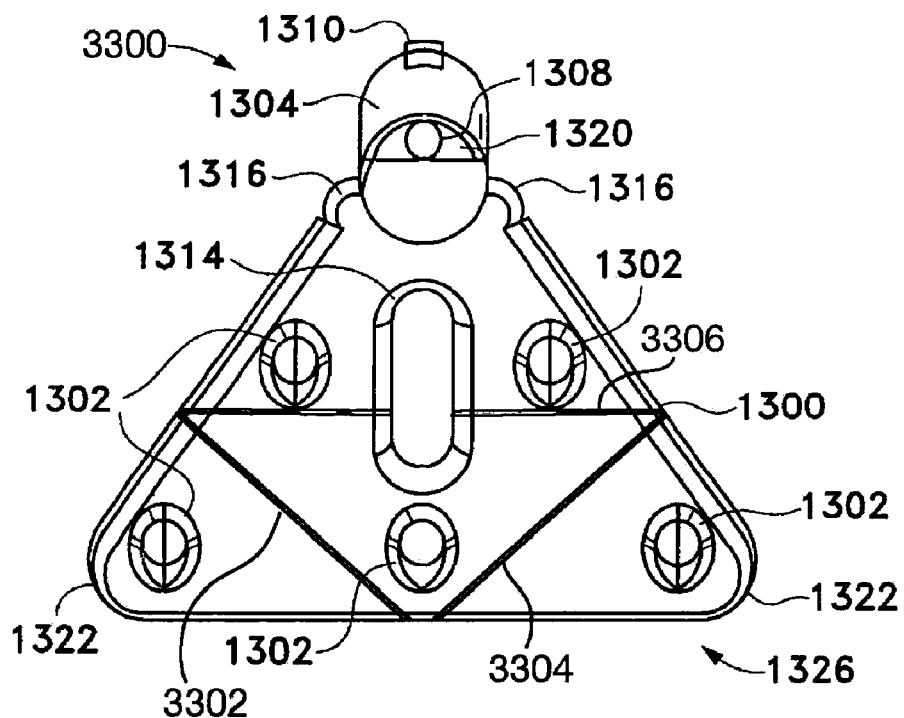

FIGS. 31A and 31B show a variation of the device (3300) in which the backing (1300) may be pre-fabricated into a standard shape with serrations or score lines (3302), (3304), (3306) formed throughout the backing (1300). Serrations (3302), (3304), (3306) may be formed by scoring the backing (1300) to create regions or boundaries having a reduced cross-sectional area relative to other parts of the backing (1300). These serrations (3302), (3304), (3306) may then allow a physician or surgeon to selectively break off portions of the backing (1300) to create a device which is custom-fitted for placement within specific regions of the body. FIG. 31A shows the back side of backing (1300) while FIG. 31B shows the top side of backing (1300) showing one example for the possible placement for serrations (3302), (3304), (3306) along backing (1300).

Figure 32A:
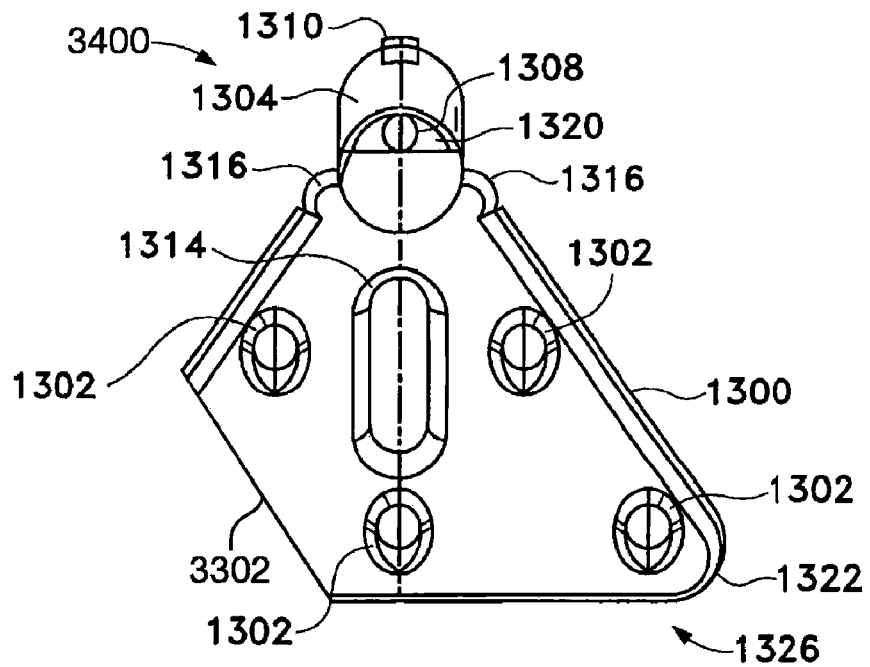
FIGS. 32A to 32D show variations of the device of FIGS. 31A and 31B in which selective portions of the backing may be removed to provide a custom-fitted device.
Figure 32B:
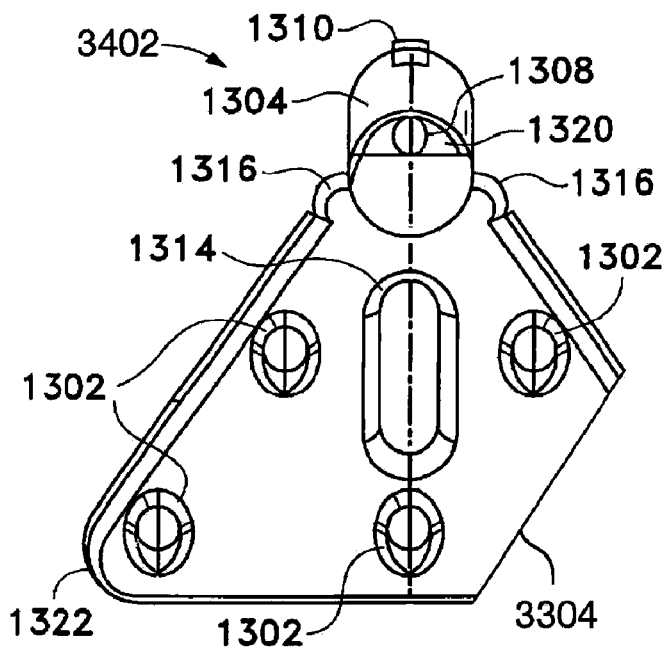
Figure 32C:
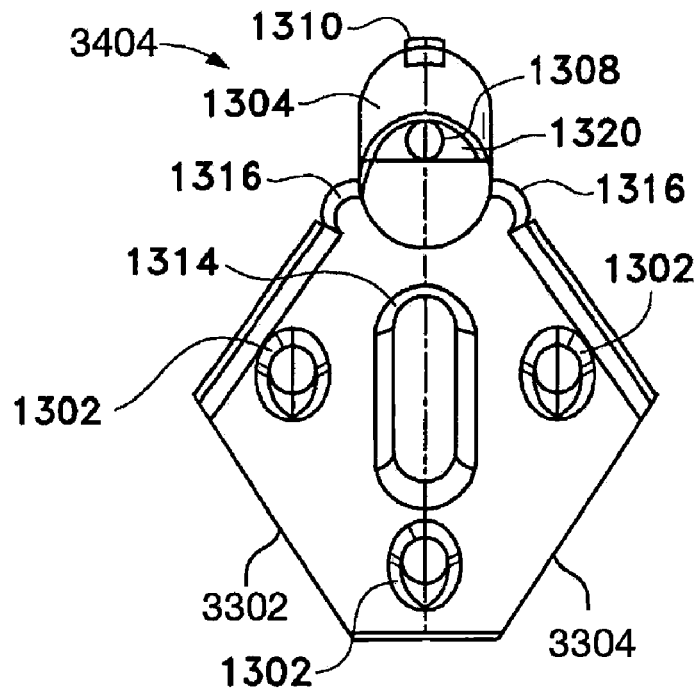
Figure 32D:
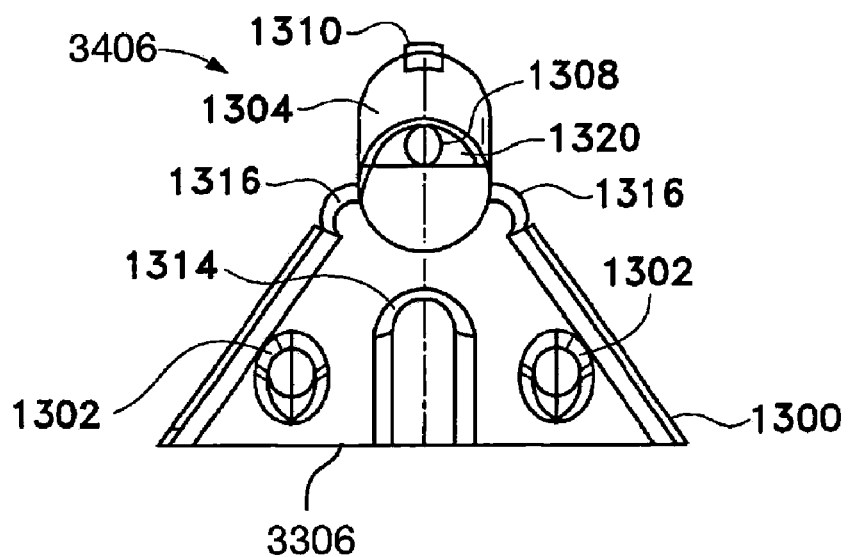

FIG. 32A illustrates one variation of the device (3400) in which a portion of the backing (1300) has been removed along serration (3302). FIG. 32B illustrates another variation in device (3402) where the backing (1300) has been removed along serration (3304) while FIG. 32C illustrates yet another variation (3404) where portions of the backing (1300) have been removed along both serrations (3302), (3304) to result in a diamond-shaped backing. Finally, FIG. 32D illustrates yet another variation (3406) where portions of the backing (1300) have been removed along serration (3306) to result in a smaller device.

Figure 33A:
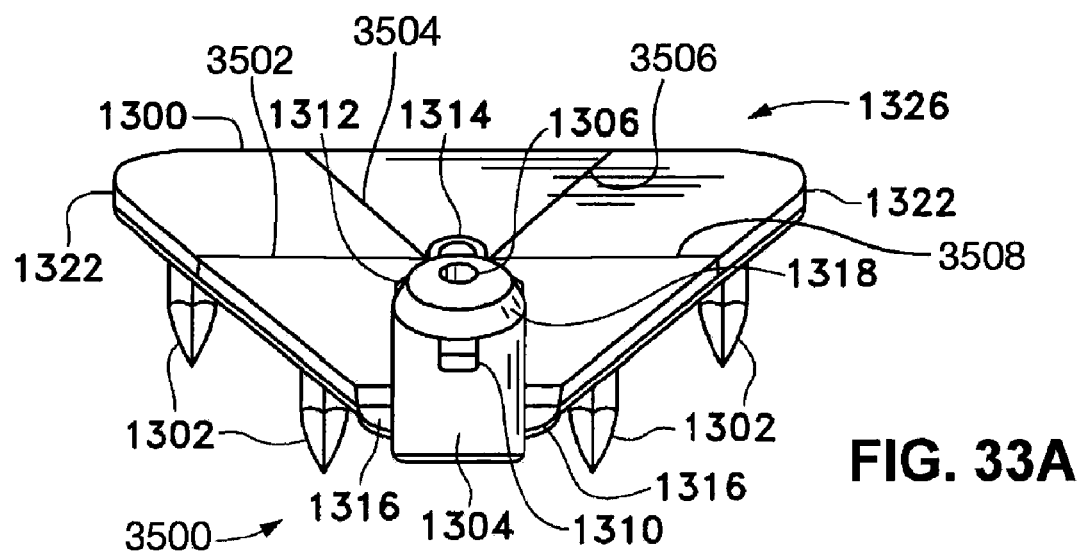
FIGS. 33A and 33B show various views of another variation of a device having alternatively placed serrations over the backing.
Figure 33B:
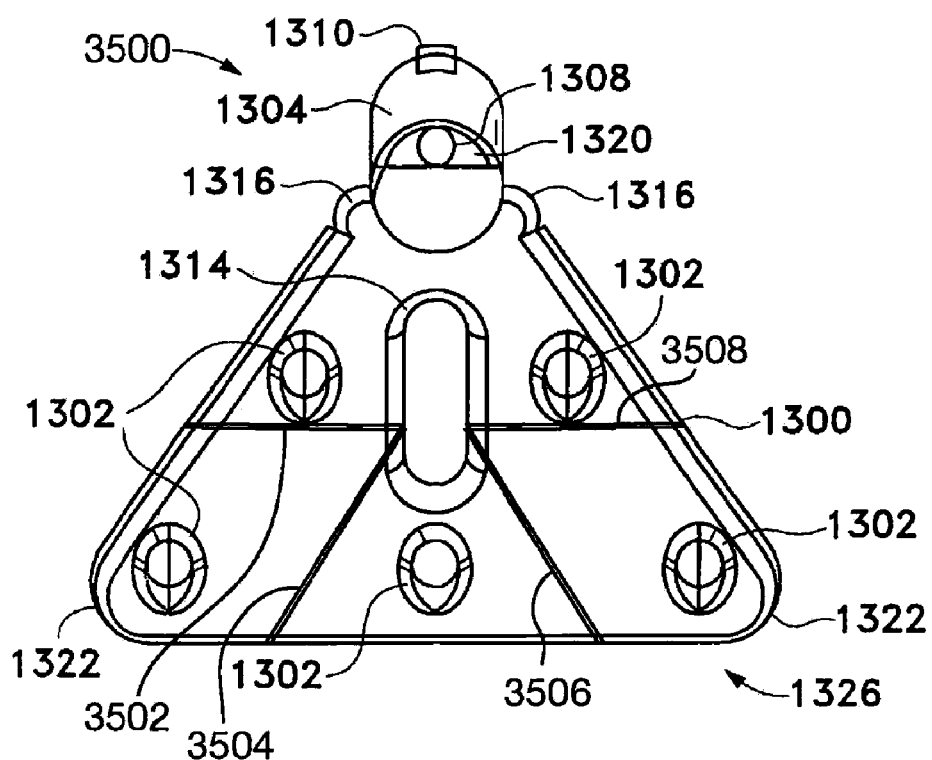
Figure 34A:
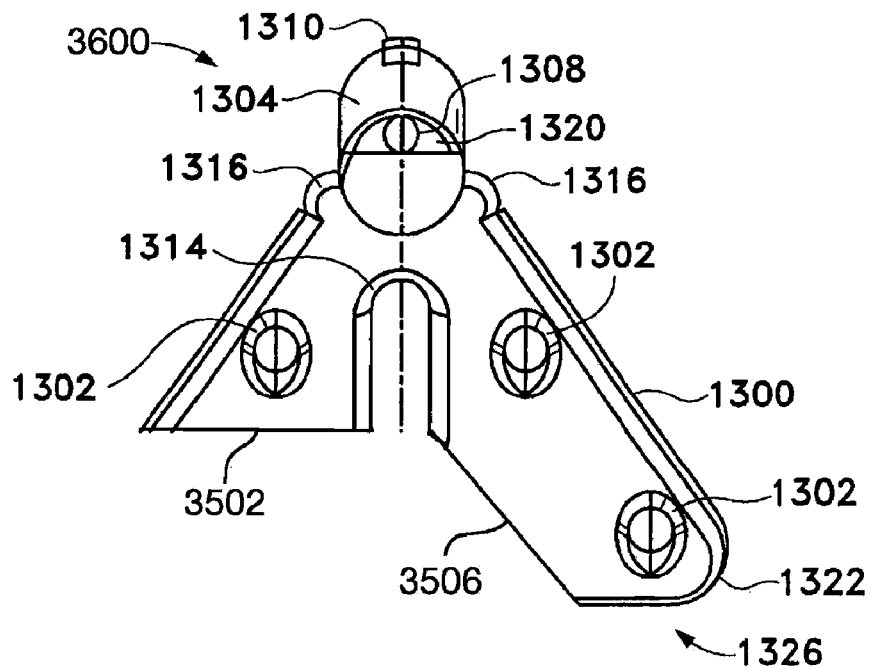
FIGS. 34A and 34B show variations of the device of FIGS. 33A and 33B in which selective portions of the backing may be removed to provide an alternative custom-fitted device.
Figure 34B:
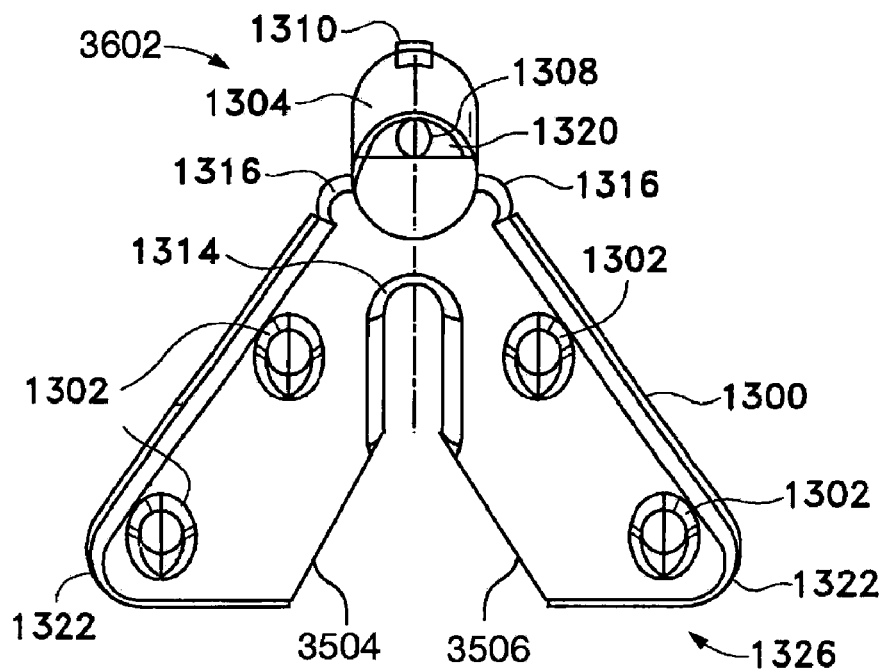

FIGS. 33A and 33B show another variation of the device (3500) in which the backing (1300) may have alternately positioned serrations (3502), (3504), (3506), (3508) over the backing (1300). FIG. 34A shows another variation of the device (3600) in which portions of the backing (1300) may be removed along serrations (3502) and (3506) to result in an asymmetrically shaped backing. Alternatively, FIG. 34B illustrates yet another variation in device (3602) in which a portion of the backing (1300) may be removed along serrations (3504) and (3506).

Generally, the serrations may be formed at regular intervals over the device. Prior to placement within the body, the physician may break off part of the backing along the break lines to form a device having a configured area. The use of serrations along the backing may be used in any of the variations of the devices described above and are not limited to the examples described herein for serration placement or positioning. These examples are merely illustrative of the possible variations in placing serrations and configuring the backing to result in a desired custom-fitted configuration. The serrations, if utilized, may be positioned along the backing in an infinite variety of geometries and locations and are dependent upon the desired shapes which may be formed and regions within the body in which the device may be placed.

Figure 35A:
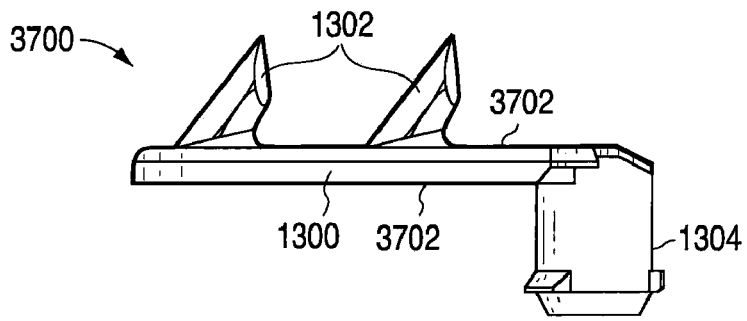
FIGS. 35A to 35C show side views of variations in which coatings may be selectively placed over the device.
Figure 35B:
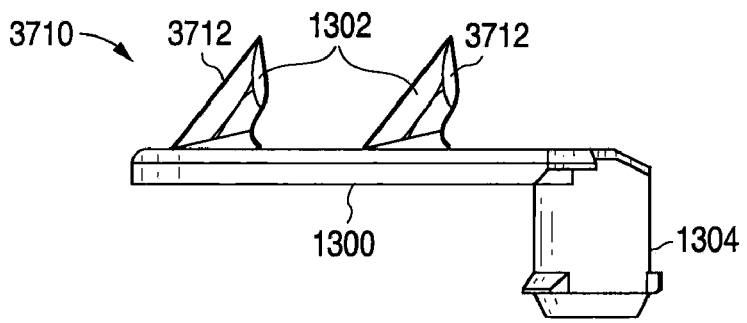
Figure 35C:
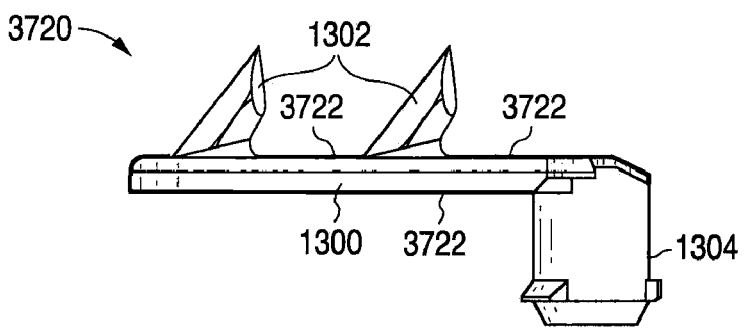

FIGS. 35A to 35C show yet another variation of the invention in which various coatings may be selectively placed over the device. FIG. 35A shows one representative variation (3700) in which a coating (3702) may be placed over the entire device, including the backing (1300) and tines (1302). Alternatively, coating (3702) may be placed only upon a single surface, e.g., the surface upon which tines are located, or along the back surface only. FIG. 35B shows another variation (3710) in which the coating (3712) may be placed only upon the tines (1302). The coating (3712) may be selectively placed over all the tines (1302) or only over a selective number of tines depending upon the desired results. FIG. 35C shows yet another variation (3720) in which the coating (3722) may be placed only upon the backing (1300) and omitted from the tines (1302). The coating (3722) in this variation (3720) may be placed upon both surfaces of backing (1300) or only upon a single surface depending upon the desired results.

The type of coatings placed upon the device may vary depending upon the desired results. For instance, one type of coating, e.g., fibrin, cyanoacrylate, etc., may be used to increase adhesion of the device or to act as an anchoring mechanism for the device to the tissue or bone surface, another type may be used to encourage or enhance the growth of the bone upon or within which the device is placed, e.g., bone matrix protein. Various coatings may also be used to create a lubricious surface over the device to facilitate its insertion within the tissue or bone. Another type of coating made from, e.g., fibroblast growth factors, may be used to enhance the healing of the wound or a coating made with, e.g., lidocaine, may also be an analgesic to reduce any accompanying pain. Another type of coating may be used on the device to promote the biocompatibility of the device and to reduce the risk of rejection by the body. To enhance the healing of the wound as well as to promote the biocompatibility of the device, the coating made from, e.g., aminoglycoside, may additionally have anti-viral and anti-bacterial properties.

Alternatively, other coating variations made from, e.g., corticosteroids, may be used to prevent or manipulate, i.e., minimize, any resulting scars, accelerate degradation of the underlying backing, or alternatively to enhance the structural strength of the device, i.e., materials such as linear polymers which increase the tensile strength of the device. Moreover, another coating variation having a high surface roughness may be coated over the device to provide an increased roughened area for facilitating tissue and bone ingrowth as well as helping to prevent slippage of the device. Any of the preceding coatings which may be utilized may include any types of coating materials as conventionally known and used in the art.

Device for Chin Lift Procedures

Figure 36A:
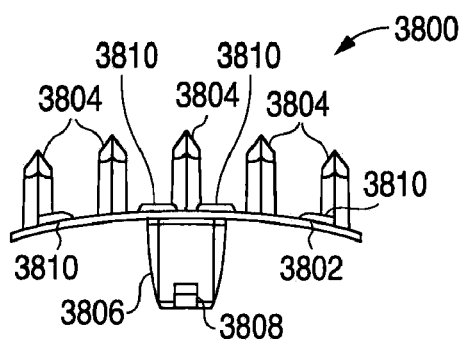
FIGS. 36A to 36C show front, top, and back views, respectively, of a variation which may be implanted in the chin area.
Figure 36B:
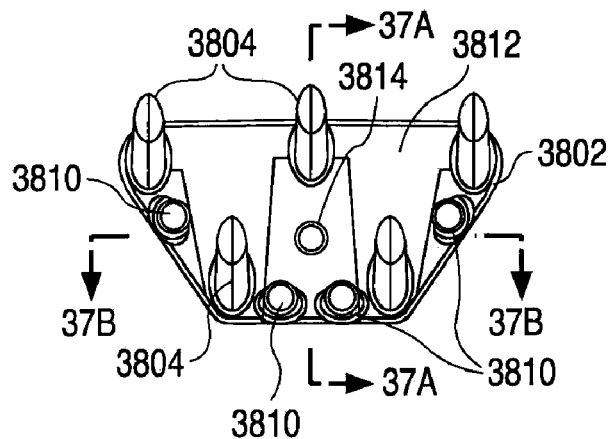
Figure 36C:
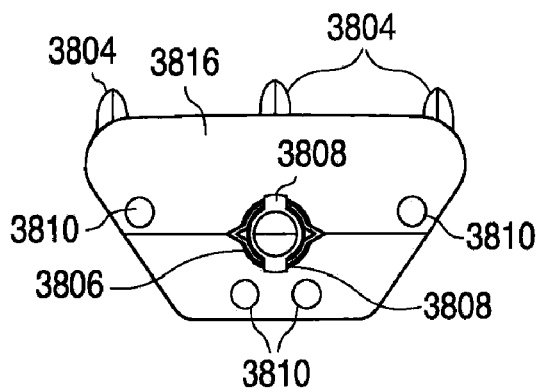

Another variation of the device is shown in FIGS. 36A to 36C, which shows front, top, and back views, respectively, of a device which may be suitable for approximating tissue in the chin region of a patient. FIG. 36A shows variation (3800) as having a supportive backing (3802) which may be curved or bowed slightly to approximate a curvature of the underlying mandibular bone in the chin region of a patient. Backing (3802) is shown generally as having a trapezoidal shape, e.g., in the shape of an isosceles trapezoid, yet backing (3802) may have a variety of configurations, e.g., triangular, rectangular, circular, ovular, etc., depending upon the bone geometry of the patient and the desired tissue fixation results. Furthermore, this device may be made of any of the biocompatible materials described above and may further incorporate the use of coatings over the device or portions of the device as also described above.

As seen in FIGS. 36A and 36B, a plurality of attachment points (3804) may extend from upper (or attachment) surface (3812) of backing (3802) in a manner similar to that described above. Although the backing (3802) may be curved, attachment points (3804) angularly extending from the backing (3802) may be configured to project parallel to one another for facilitating tissue placement onto the device (3800). The parallel configuration of the attachment points (3804) extending from the curved backing (3802) may be clearly seen in FIG. 36A. Alternative variations may have individual attachment points (3804) extending perpendicularly from the backing (3802) such that the points (3804) fan out relative to the backing (3802). Moreover, the backing (3802) may be configured such that its radius of curvature is perpendicular to a direction of the loading forces imparted by the tissue onto the device (3800) once implanted.

The backing (3802) may also have an anchoring region or post (3806) extending from lower surface (3816), i.e., the side opposite to the attachment points (3804), as seen in FIG. 36C. As described above, post (3806) may be a variety of shapes, e.g., a hook or an angled post, etc., but is typically a post perpendicularly extending from backing (3802). Moreover, post (3806) may be formed integrally with backing (3802) so as to form a single piece. Alternatively, post (3806) may also be a separate structure fixedly attached to backing (3802) by a variety of fastening methods, as further described above.

Moreover, the distal end of post (3806) may be chamfered so as to provide a degree of tolerance to enable the surgeon to easily locate and insert post (3806) into a receiving hole.

As described above, post (3806) may also comprise a locking device, e.g., partial collars (or tabs) (3808), located near the distal end of post (3806) to facilitate the secure anchoring of the device (3800) within bone and to prevent rotation of the device about post (3806) once implanted within the bone. Moreover, although only two tabs are shown on opposite sides of post (3806), any number of tabs may be used and placed around post (3806) to vary the anchoring effect. Partial collars or tabs are shown in the FIGS. 36A and 36C, but a circumferential collar may instead be utilized again depending upon the desired anchoring effect. Tabs (3808) may be formed to work in much the same manner as described above.

Curved backing (3802) may optionally further define at least one, and preferably several, holes (3810) through backing (3802). Four holes (3810) are shown in FIGS. 36B and 36C as being located around the periphery of backing (3802); these holes (3810) may be used for securing sutures or other flexible fastening materials should the surgeon perform an additonal procedure where, e.g., the polyglotis muscle is sutured and secured to the holes (3810) via the sutures to tighten the overall region within the neck. Fewer or additional holes may be utilized and their positioning along backing (3802) may also be varied. For instance, rather than placement along the periphery of backing (3802), one or more holes may be positioned closer to the center of the device (3800). Sutures may optionally be anchored to the device (3800) for additional procedures such as a cervicoplasty (neck lift) or platysmaplasty (repair of the neck muscle).

Figure 37A:
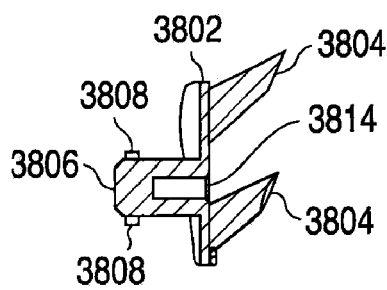
FIG. 37A is a view of cross-section 37A-37A from FIG. 36B showing the post and attachment points.
Figure 37B:
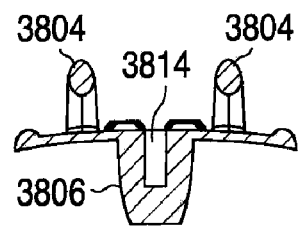
FIG. 37B is a view of cross-section 37B-37B from FIG. 36B showing another view of the post and attachment points.
Figure 38:
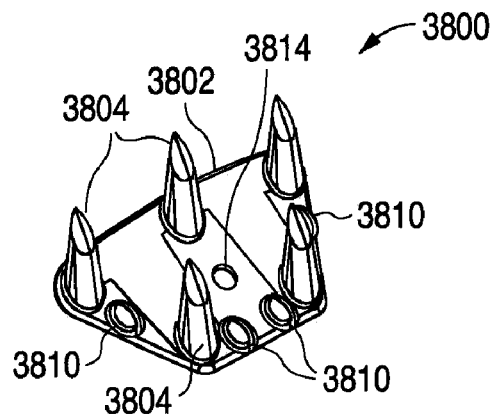
FIG. 38 is a perspective view of the device of FIGS. 36A to 36C.

Backing (3802) and post (3806) may incorporate a cavity or hole (3814) for use with a deployment tool, as described below. FIG. 36B shows cavity (3814) defined within backing (3802). Cavity (3814) may be clearly seen in FIG. 37A, which shows cross-section 37A-37A from FIG. 36B. The cavity (3814) may extend partially into post (3806) from upper surface (3812) or it may extend entirely therethrough so long as an opening is provided for receiving a deployment tool, which is described in further detail below. FIG. 37B shows another cross-section 37B-37B from FIG. 36B also showing another view of cavity (3814). FIG. 38 shows a perspective view of the device (3800).

Figure 39A:
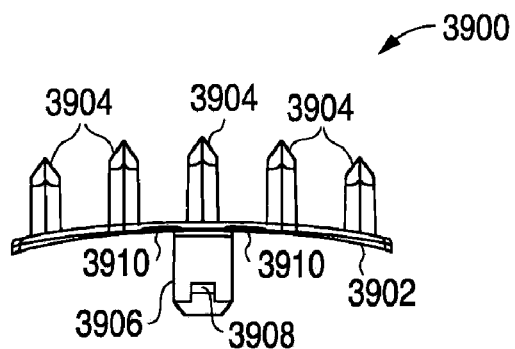
FIGS. 39A and 39B are front and back views, respectively, of another variation which may be implanted in the chin area.
Figure 39B:
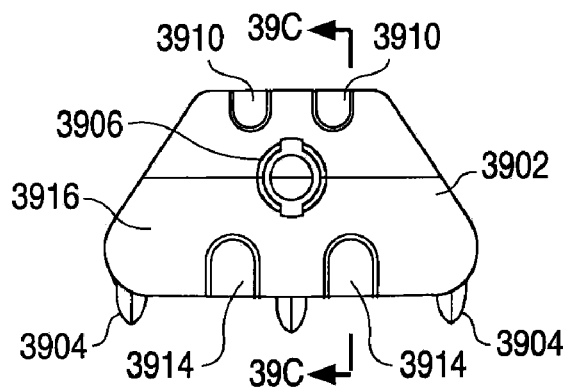
Figure 39C:
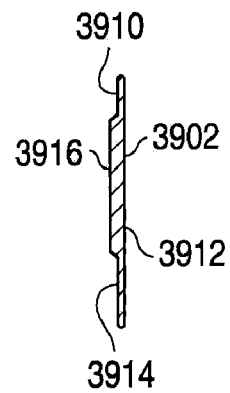
FIG. 39C is a view of cross-section 39C-39C from FIG. 39B.

FIGS. 39A to 39C show front, back, and cross-sectional side views of another variation which is similar to that shown in FIGS. 36A to 36C. As shown, the device (3900) has a supportive backing (3902) which may also be curved or bowed slightly to approximate a curvature of the underlying mandibular bone in the chin region of a patient. Attachment points (3904) may extend from upper or attachment surface (3912) and post (3906) may extend from an opposite lower surface (3916). Post (3906) may similarly have a partial collar, full collar, or locking tabs (3908) to facilitate the anchoring of the device (3900) within the bone.

This variation, however, may include one or several regions along backing (3902) which are configured to facilitate placement or positioning of the device (3900) in the bone with a placement tool. As shown in FIG. 39B and 39C, surface regions (3910), (3914) may be configured as areas of the backing (3902) having a reduced thickness. FIG. 39C shows cross-section 39C-39C from FIG. 39B where the reduced thickness of surface regions (3910), (3914) may allow for a tool to grasp backing (3902) for placement onto the bone. Surface regions (3910), (3914) may also allow for the pulling or manipulation of backing (3902) even when a majority of lower surface (3916) is flush against an outer surface of the bone.

Figure 40A:
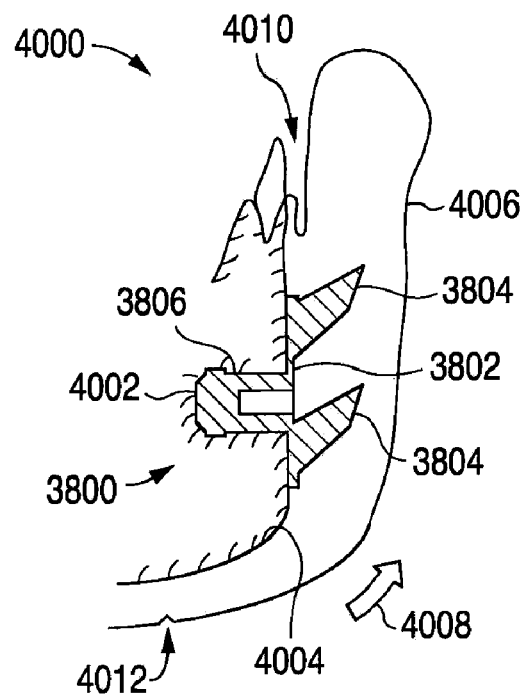
FIG. 40A is a cross-sectional side view of the device of FIGS. 36A-36C shown implanted within the chin area.

FIG. 40A shows an example of the device of FIGS. 36A-36C implanted within the chin area (4000). To implant the device (3800), an incision may be made either in the area (4010) inside the lower lip or along the line of a crease (4012) underneath the chin. A hole (4002) may then be drilled through the incision and into the mandibular bone preferably close to the mental protuberance (4004) of the jaw to avoid damage to underlying nerves. The device (3800) may then be advanced through the incision either by directly grasping the device (3800) or via a deployment tool. The device (3800) is guided such that post (3806) is inserted securely into bone hole (4002). Variations on the bone hole (4002) are described in greater detail above.

Once device (3800) has been desirably positioned within bone hole (4002), the deployment tool (if used) may be removed and the dermis (4006) may be approximated a desirable distance along the direction of arrow (4008) and affixed onto attachment points (3804). The incision may then be sutured and the device (3800) left implanted to eventually become absorbed by the body. An endoscope may be optionally used during this procedure but it may also be omitted.

Figure 40B:
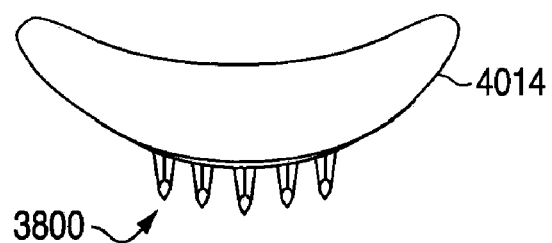
FIGS. 40B and 40C are side and front views, respectively, of the device of FIGS. 36A-36C which may be used in conjunction with a chin augmentation implant.
Figure 40C:
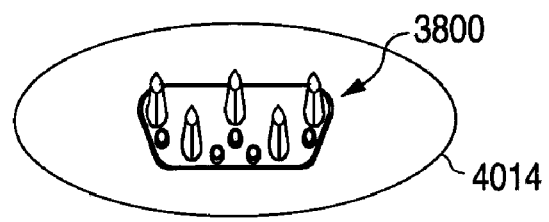

The chin lift device may also be used in conjunction with chin augmentation implants, as shown in FIGS. 40B and 40C, which show side and front views, respectively, of a chin lift and augmentation assembly. Device (3800) may be incorporated integrally or as a separate component of chin augmentation implant (4014). This assembly may then be implanted upon the mandibular bone of a patient to simultaneously augment and lift the jaw line, chin region, or both with a single assembly.

Placement Tools

Many of the variations on the brow lift device may be inserted and secured into a patient in a number of ways. One such method involves using an insertion tool of a type shown in FIG. 41A. This variation shows a top view of such a tool which may serve several functions. This tool comprises manipulation handle (3100), by which a doctor or surgeon manipulates, for example, the device of FIGS. 13A-13C. As shown further in FIG. 41B, cross-section 41B-41B from FIG. 41A, handle (3100) may be hinged by any conventional methods but shown here as bolt hinge (3104). At a distal end of handle (3100) are grasping members (3102). These grasping members (3102) may generally be designed to have opposing members which may be urged together or apart, i.e., to close or open, as handle (3100) is urged about hinge (3104).

To prevent uncontrolled rotation of handle (3100) and to provide a way of securely grasping the device, handle (3100) may also comprise a locking mechanism which may hold handle (3100) and grasping members (3102) in a desired position. Grasping members (3102) are preferably designed or configured to securely hold the supportive backing (1300) relatively planar with grasping members (3102) such that attachment points (1302) face away from the patient during insertion. It is further preferable that grasping members (3102) securely hold the MTDS device via anchoring post (1304) to allow easy handling and insertion. As seen in FIG. 41B, grasping members (3102) are preferably angled relative to a plane defined by handle (3100) at a predetermined angle, α, to further allow easy insertion of the device.

FIG. 41C shows a close-up cross-sectional view of the distal end of the insertion tool. As shown, also attached to hinge (3104) is support block (3106). Support block (3106) is preferably configured to attach to handle (3100) at hinge (3104) yet still allow rotational movement of the tool about hinge (3104). Support block (3106) also preferably defines channel (3110) through a top surface of support block (3106), as shown in FIGS. 41A-41C. Channel (3110) may run substantially parallel relative to a symmetrical axis defined by the insertion tool. Support block (3106) may be supported by support post (3108) which may help in preventing rotation of support block (3106) about hinge (3104) as well as maintaining a position of the block relative to handle (3100).

Further seen in FIG. 41C, channel (3110) in support block (3106) is preferably angled relative to the plane defined by handle (3100). While grasping members (3102) are angled at an angle, α, relative to handle (3100), channel (3110) may be angled relative to grasping members (3102) at a desired angle, β. This angle β is preferably similar to the angle formed by attachment points (1302) relative to supportive backing (1300). Angling channel (3110) may allow a mating block, described below in further detail, to run along channel (3110) and press against the tissue to be lifted against attachment points (1302). A block pressing against tissue to be set on attachment points (1302) allows for optimal piercing of the tissue if the force applied by the block is in the same or similar angle or direction as attachment points (1302).

Figure 41D:
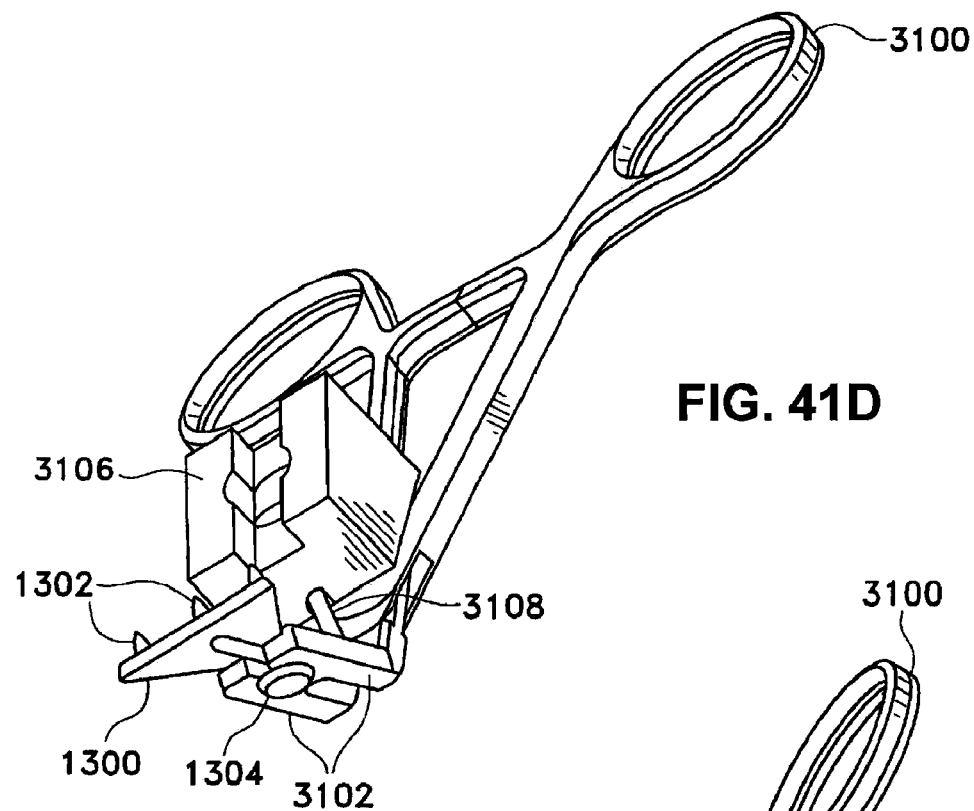
FIG. 41D is a perspective view from the bottom showing the insertion tool of FIG. 41A.
Figure 41E:
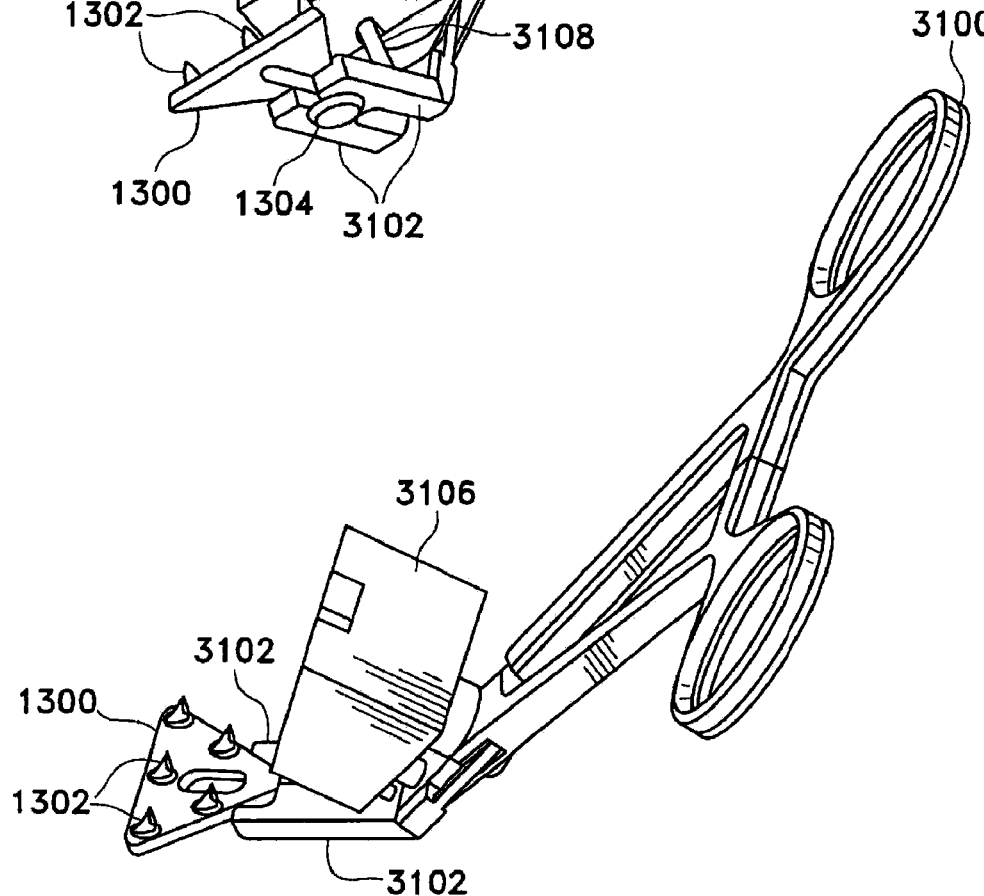
FIG. 41E is a perspective view from the top showing the insertion tool of FIG. 41A.

FIGS. 41D and 41E show a bottom and a top perspective view, respectively, of the insertion tool from FIG. 41A grasping an device. As seen in FIG. 42A, the same insertion tool from FIG. 41A is shown with the addition of depressible block (3200) mated with support block (3106). Depressible block (3200) may be mated with support block (3106) via channel (3110), into which mating slide (3204) may be inserted. Slide (3204) may be an integral extension of depressible block (3200) and is preferably configured to allow a degree of tolerance relative to channel (3110) so that depressible block (3200) may slide freely or when urged via channel (3110) and mating slide (3204), as shown by the arrow in FIG. 42B.

FIG. 42B also shows a cross-section 42B-42B from FIG. 42A. Depressible block (3200) further illustrates depression region (3202), which may be a slight indentation defined in the surface facing away from the patient during insertion. Depression region (3202) may serve as a locator for the optimal region the physician may depress to force depressible block (3200) and contact surface (3206) downward against the tissue and attachment points (1302) in order to set, or pierce, the tissue. FIG. 42C shows a close-up cross-sectional view of the distal end of the insertion tool with depression block (3200) inserted. Contact surface (3206) is the surface which ultimately presses the tissue against attachment points (1302) and is preferably relatively parallel with the plane defined by grasping members (3102) and supportive backing (1300) to present the greatest surface area pressing against the tissue. Depressible block (3200) is further preferably configured to slide or run along the same angle, β, at which support block (3106) is set to provide a planar contact surface (3206) to press against the tissue at an optimal angle, which may be at the same or similar angle as attachment points (1302), as discussed above.

Figure 42D:
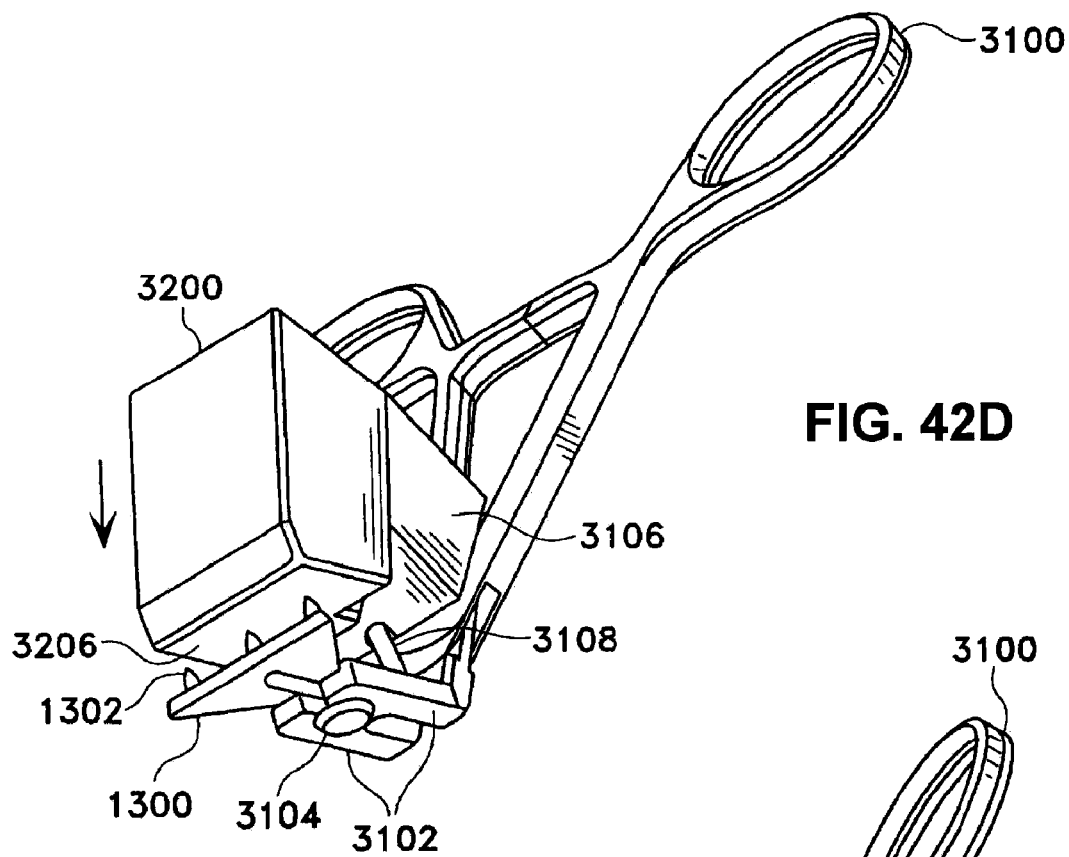
FIG. 42D is a perspective view from the bottom showing the insertion tool of FIG. 42A.
Figure 42E:
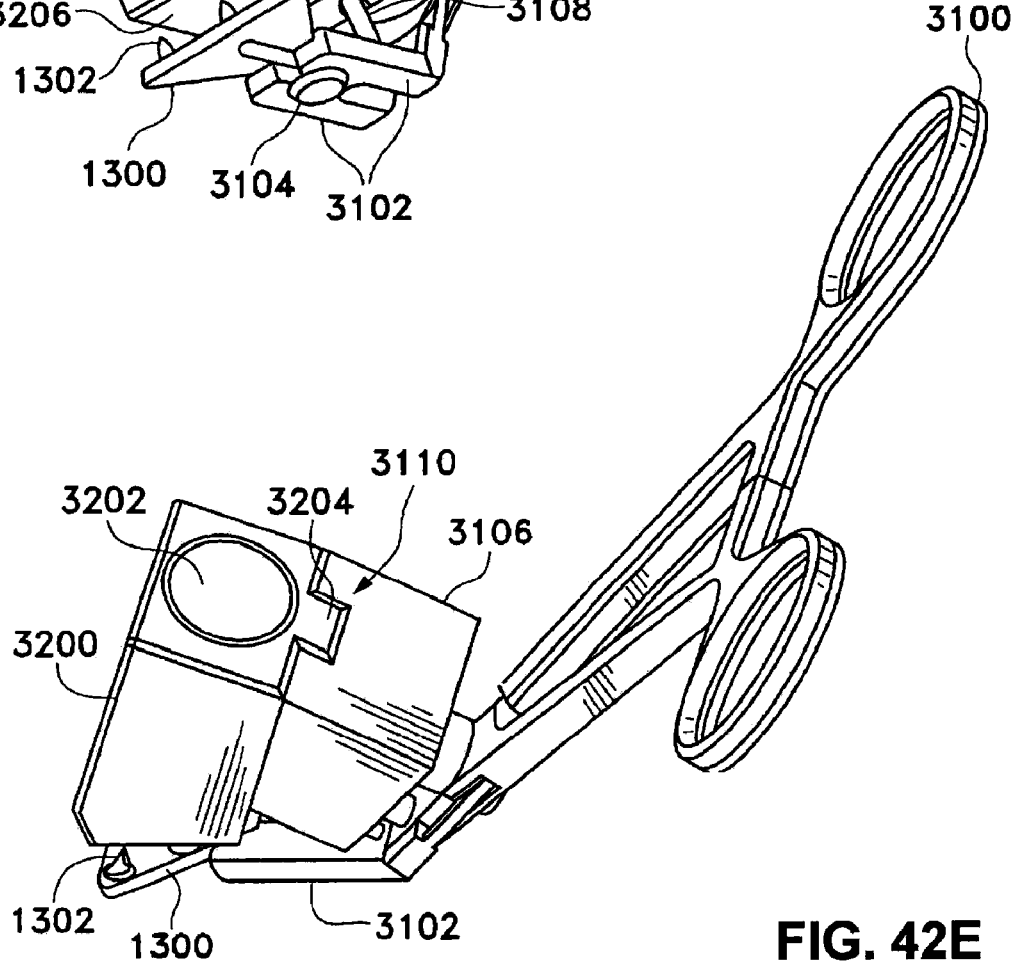
FIG. 42E is a perspective view from the top showing the insertion tool of FIG. 42A.

FIGS. 42D and 42E show a bottom and a top perspective view, respectively, of the insertion tool from FIG. 42A with depressible block (3200) set in channel (3110). Although the placement tool has been described with depressible block (3200), the tool may also be used without a block for depressing the tissue or scalp against the attachment points (1302). Rather, affixing or setting the tissue may also be done by hand, i.e., simply depressing the tissue with the hand and fingers against attachment points (1302).

Figure 43A:
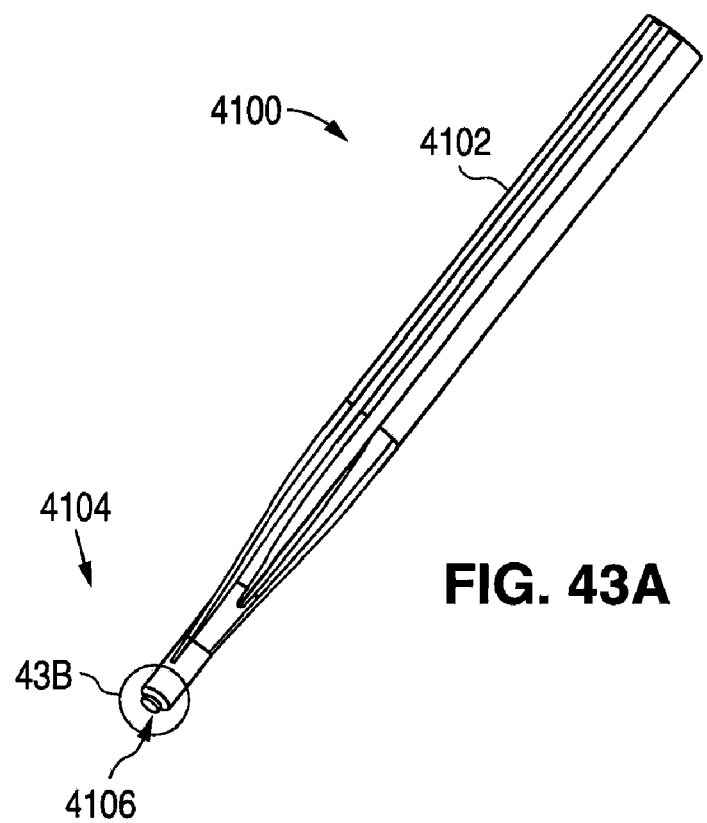
FIGS. 43A and 43B are perspective and detail views, respectively, of a tool variation which may be used to implant the device of FIGS. 36A to 36C.
Figure 43B:
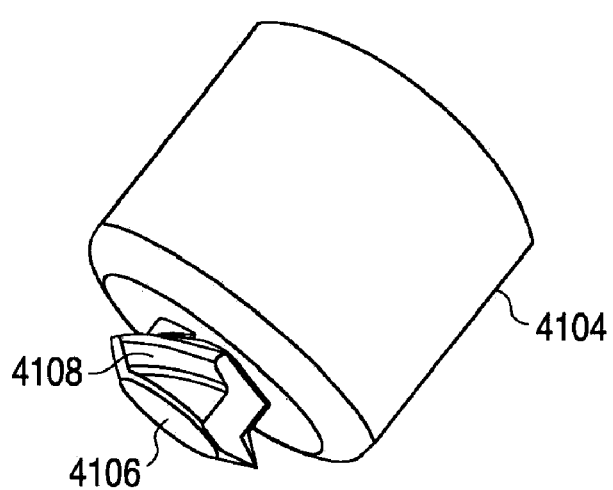

Another insertion or deployment tool variation is shown in FIGS. 43A and 43B which may be used with the device of FIGS. 36A to 36C. Tool (4100) generally has an elongate handle (4102) configured to allow the surgeon to comfortably grip the tool (4100). The distal end (4104) may have an attachment post (4106) extending at least partially therefrom. Detail (42B) of attachment post (4106) is shown in FIG. 43B. Attachment post (4106) may be configured to mechanically engage device (3800) via cavity (3814). One variation is to configure attachment post (4106) as a threaded or partially threaded member which may be screwed and unscrewed into cavity (3814) during insertion and deployment. Another variation may include an attachment post (4106) having radially adjustable protrusions for engagement with cavity (3814).

Figure 44:
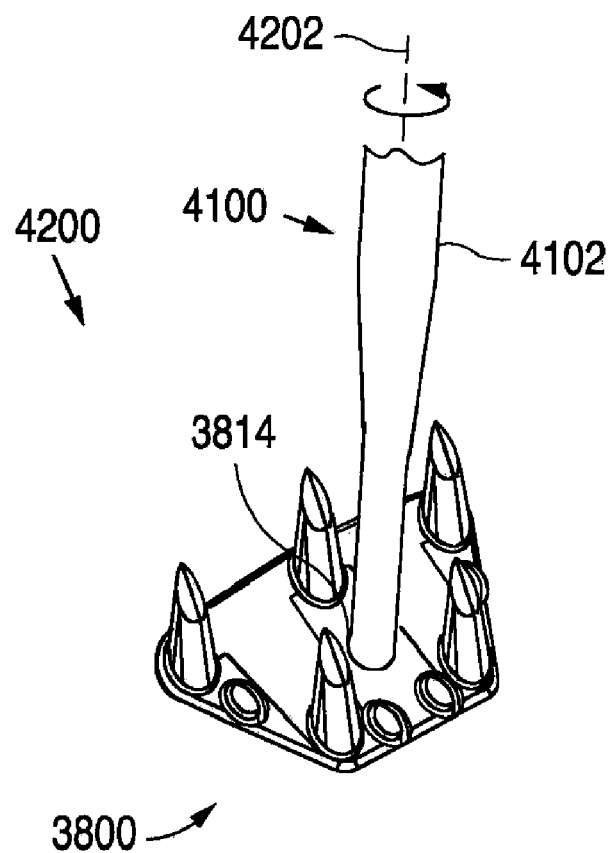
FIG. 44 is a perspective view of a tool and device assembly for implanting the device of FIGS. 36A to 36C.

FIG. 44 shows a perspective view of one variation of how deployment tool (4100) may be utilized with device (3800) as a deployment assembly (4200). As shown, attachment post (4106) may be securely engaged within cavity (3814) by rotating handle 4102) about longitudinal axis (4202) of handle (4102). Device (3800) may be anchored to the bone by urging the device (3800) with handle (4102). If repositioning of device (3800) is necessary, tool (4100) may be used. Once device (3800) is desirably positioned within the bone, tool (4100) may be released from cavity (3814) by rotating handle (4102) in the opposite direction.

We have described this invention by example and by description of the physical attributes and benefits of the structure. This manner of describing the invention should not, however, be taken as limiting the scope of the invention in any way.

What is claimed is:

1. An implantable tissue approximation system, comprising:
    a) a non-resilient and curved supportive backing;
    b) a plurality of attachment points extending from the backing in a canted manner, wherein the attachment points are adapted to distribute a load over the backing; and
    c) an anchoring region integral with the backing and comprising a bone engagement post.

2. The tissue approximation system of claim 1 wherein the backing comprises a shape selected from the group consisting of trapezoids, triangles, circles, and ovals.

3. The tissue approximation system of claim 1 wherein the backing comprises an isosceles trapezoidal shape.

4. The tissue approximation system of claim 1 wherein the backing defines at least one hole therethrough.

5. The tissue approximation system of claim 1 wherein the device comprises a material selected from the group consisting of biodegradable and biological materials.

6. The tissue approximation system of claim 5 wherein the biodegradable material comprises a polymer or copolymer.

7. The tissue approximation system of claim 6 wherein the polymer or copolymer comprises one or more materials selected from the group consisting of polyglycolide, polylactide, poly-.alpha.-caprolactone, polydiaxanone, polyglyconate, polylactide-co-glycolide, their mixtures, alloys, and random and block copolymers.

8. The tissue approximation system of claim 5 wherein the biological material comprises one or more materials selected from the group consisting of collagen, hydroxyapatite from natural sources, hydroxyapatite from synthetic sources, bone graft, and any polymerized versions thereof.

9. The tissue approximation system of claim 1 wherein the post defines a cavity at least partially therein.

10. The tissue approximation system of claim 1 further comprising a chin augmentation implant adjacent to the backing.

11. The tissue approximation system of claim 1 further comprising a tool adapted to deploy an implantable tissue approximation device.

12. The tissue approximation system of claim 11 wherein the tool comprises an elongate handle and an attachment post positioned at a distal end of the handle, the attachment post being at least partially threaded and adapted for engagement with the implantable tissue approximation device.

13. A method of tissue approximation in a chin-lift surgical procedure comprising:
   a) securing an implantable tissue approximation device to bone having a curved surface, the approximation device comprising a supportive, curved, and non-resilient backing; a plurality of attachment points extending from the backing in a canted manner, wherein the attachment points are adapted to distribute a load over the backing; and an anchoring region integral with the backing and having a bone engagement post used for the securing of the implantable tissue approximation device to bone;
   b) mobilizing tissue or layer of tissue to be approximated towards the approximation device; and
   c) setting the tissue or layer of tissue onto the approximation device.

14. The method of claim 13 wherein securing the implantable tissue approximation device in the step a) comprises deploying the device via an elongate tool temporarily attached to the device.

15. The method of claim 13 wherein the tissue or layer of tissue in the step c) is set on the approximation device via the plurality of attachment points.

16. The method of claim 13 farther comprising a preliminary step of cutting the tissue or layer of tissue by a predetermined length.

17. The method of claim 16 wherein the tissue or layer of tissue in the step b) is mobilized by the predetermined length.

* * * * *